(12) United States Patent
Thum et al.

(10) Patent No.: US 11,371,043 B2
(45) Date of Patent: Jun. 28, 2022

(54) LNCRNAS FOR THERAPY AND DIAGNOSIS OF CARDIAC HYPERTROPHY

(71) Applicant: Medizinische Hochschule Hannover, Hannover (DE)

(72) Inventors: Thomas Thum, Hannover (DE); Kumarswamy Regalla, Hannover (DE); Janika Viereck, Hannover (DE)

(73) Assignee: MEDIZINISCHE HOCHSCHULE HANNOVER, Hannover (DE)

(*) Notice: Subject to any disclaimer, the term of this patent is extended or adjusted under 35 U.S.C. 154(b) by 0 days.

(21) Appl. No.: 16/017,375

(22) Filed: Jun. 25, 2018

(65) Prior Publication Data
US 2020/0165604 A1    May 28, 2020

Related U.S. Application Data

(62) Division of application No. 15/305,976, filed as application No. PCT/EP2015/058684 on Apr. 22, 2015, now abandoned.

(30) Foreign Application Priority Data

Apr. 22, 2014 (EP) ..................................... 14165504

(51) Int. Cl.
*C12N 15/113* (2010.01)
*A61P 9/00* (2006.01)
*A61K 48/00* (2006.01)
*C12Q 1/6883* (2018.01)

(52) U.S. Cl.
CPC ........ *C12N 15/113* (2013.01); *A61K 48/0058* (2013.01); *A61P 9/00* (2018.01); *C12Q 1/6883* (2013.01); *C12N 2310/11* (2013.01); *C12N 2310/111* (2013.01); *C12N 2310/113* (2013.01); *C12N 2310/14* (2013.01); *C12N 2310/20* (2017.05); *C12N 2320/32* (2013.01); *C12Q 2600/158* (2013.01); *C12Q 2600/178* (2013.01)

(58) Field of Classification Search
CPC ..... C12N 15/113; C12N 2310/11; A61P 9/00; A61K 48/0058; C12Q 2600/178
See application file for complete search history.

(56) References Cited

U.S. PATENT DOCUMENTS

| 6,451,594 B1 | 9/2002 | Chien et al. |
| 2004/0244969 A1 | 12/2004 | Kotlar et al. |
| 2010/0093560 A1 | 4/2010 | Colbeck et al. |

FOREIGN PATENT DOCUMENTS

| WO | 2000015821 | 3/2000 |
| WO | 2004031359 | 4/2004 |
| WO | 2008104290 | 9/2008 |

OTHER PUBLICATIONS

Thum et al (Circ Res. 2015;116:751-762) (Year: 2015).*
Escobar (J. Human Hypertension 16 (Suppl 1): S61-S63, 2002) (Year: 2002).*
Schoen et al (Cellular Microbiology (2005) 7(5): 709-724) (Year: 2005).*
Xiang et al (Nature Biotech. 24(6): 697-702, 2006) (Year: 2006).*
Li et al (Cell Cycle 5:18, 2103-2109, 2006) (Year: 2006).*
Nguyen et al (In: Madame Curie Bioscience Database [Internet]. Austin (TX): Landes Bioscience; 2000-2013. Retrieved from: https://www.ncbi.nlm.nih.gov/books/NBK6085/) (Year: 2013).*
UCSC Genome Browser on Human Feb. 2009 (GRCh37/hg19) Assembly, 3 pages.
Bayley et al., 2009, Plos One, 4(11) e7987:1-7.
GenBank Accession No. BC053637.1, 2003, (retrieved from https://www.ncbi.nim.nih.gov/nuccore/BC053637 on Feb. 23, 2007).
Greco et al., 2013, EP Heart J, 34(1):P3250.
Luo et al., 2013, Febs Journal, 280(7):1709-1716.
Mathiyalagan et al., Circulation—Scientific Sessions and Resuscitation Science Symposium of the American Heart Association, (2013) 128(22):10907, XP-002729226 and Abstract (Epigenetics, 9(1):101-112, XP-008171866).
Wang et al., 2014, Cir Res, 114(9):1377-1388, XP-009179216, (Supplemental Material), XP-002729224 and Abstract XP-002729225.
Zhang et al., 1992, Genetics, 1:40-44.
Tirziu, et al., "Myocardial hypertrophy in the absence of external stimuli is induced by angiogenesis in mice," The Journal of Clinical Investigation, vol. 117, No. 11, Nov. 2007, pp. 3188-3197.
Walsh, et al., "Cardiac growth and angiogenesis coordinated by intertissue interactions," The Journal of Clinical Investigation, vol. 117, No. 11, Nov. 2007, pp. 3176-3179.

* cited by examiner

*Primary Examiner* — Richard A Schnizer
(74) *Attorney, Agent, or Firm* — Arentfox Schiff LLP

(57) ABSTRACT

The present invention relates to a pharmaceutical composition comprising (i) a compound promoting the expression and/or the activity of one or more long non-coding RNAs (lncRNAs) selected from SEQ ID NOs 12, 8 to 11 and 13; and/or (ii)a compound inhibiting the expression and/or the activity of one or more lncRNAs selected from SEQ ID NOs 1 to 7, 27 and 28. The present invention also relates to a compound (i) promoting the expression and/or the activity of one or more lncRNAs selected from SEQ ID NOs 12, 8 to 11 and 13; and/or (ii) inhibiting the expression and/or the activity of one or more lncRNAs selected from SEQ ID NOs 1 to 7, 27 and 28 for use in treating or preventing cardiac hypertrophy.

8 Claims, 52 Drawing Sheets

Specification includes a Sequence Listing.

FIG. 16A 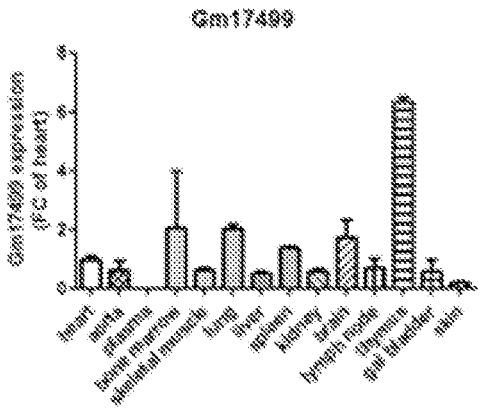 FIG. 16B
FIG. 16C 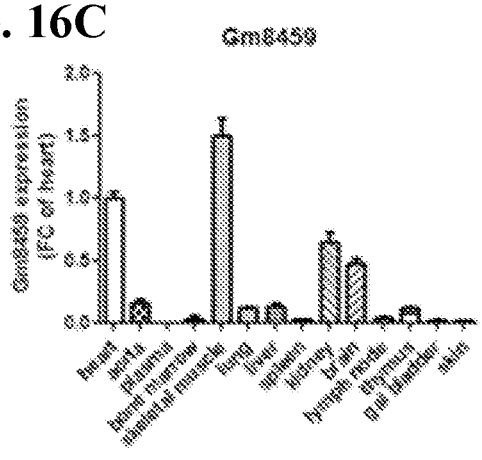 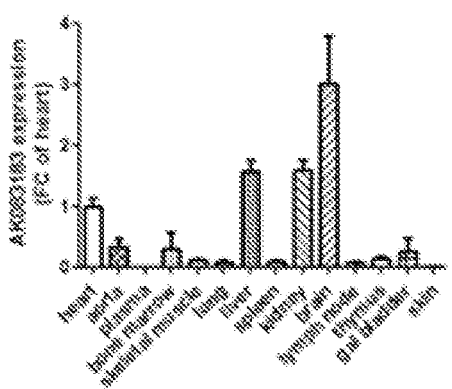 FIG. 16D
FIG. 16E 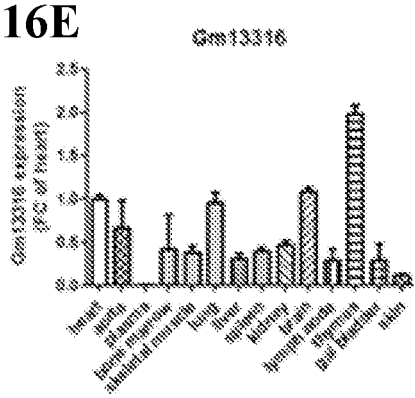 FIG. 16F

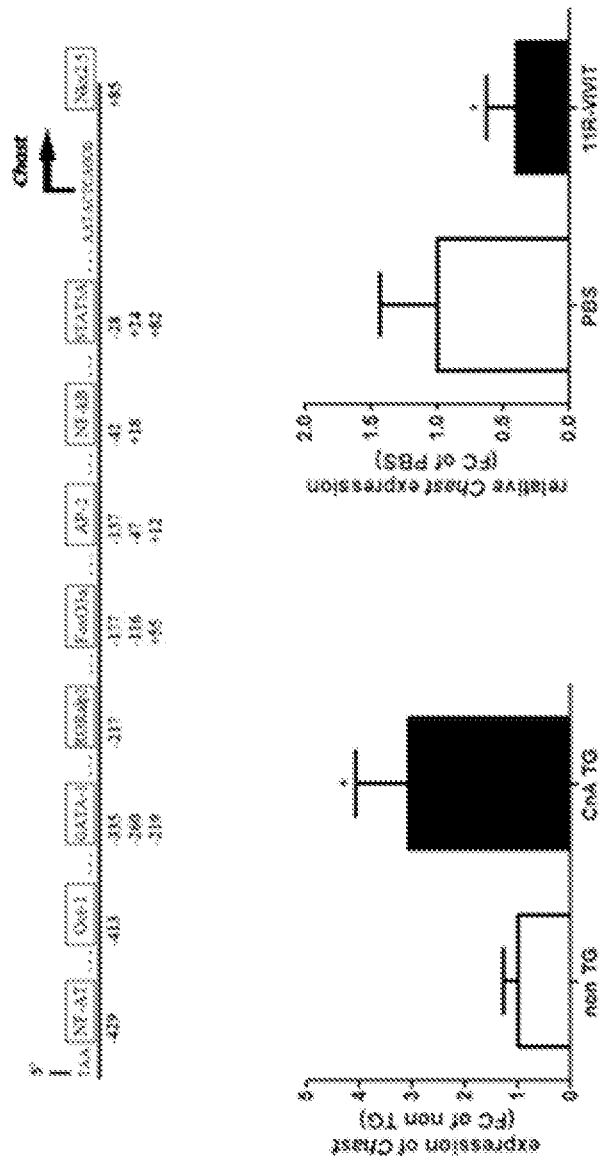

SEQUENCE LISTING

```
<160> NUMBER OF SEQ ID NOS: 65

<210> SEQ ID NO 1
<211> LENGTH: 293
<212> TYPE: DNA
<213> ORGANISM: Homo sapiens
<220> FEATURE:
<223> OTHER INFORMATION: chromosome 17, GRCh38.p2 Primary Assembly

<400> SEQUENCE: 1 aagggaaac aagtgccctc agaggcgctt ggctgaggat ggagaggggc tgagcccact      60
ggcagggcag aaccaggtca tgtgccatgg ccctccactg ggcctccctc ccccagtttc    120
tcttctcttc tctggcccta ccatctattg tccttggggg aagctgtggc acctagatgg    180
gcagagggtg ccaacttgta atctgaaagg ggccttcaag gacaggaaat cgcagatctg    240
aatgttgtct gtttccatcc cattttaccg caatctgatt tccctgagaa tta           293

<210> SEQ ID NO 2
<211> LENGTH: 267
```

```
<212> TYPE: DNA
<213> ORGANISM: Homo sapiens
<220> FEATURE:
<223> OTHER INFORMATION: AT2 receptor-interacting protein 1 mRNA,
      complete cds

<400> SEQUENCE: 2
tctgtggtgg aatgacattt gctgtgtagg catctttcct ctgactgtat ttcttggcct      60
tgaagagtac tgagtttaaa aagacagtat gtgacagtcc atggaaattg cctcttctgt    120
gaaatctcgc cacctgctcc gaagacatgt tgttgtctcc caaattctcc ttatccacca   180
ttcacatacg actgacggcc aaaggattgc ttcgaaacct tcgacttcct tcagggttta   240
ggagaagcac tgttgttttc cacacag                                        267

<210> SEQ ID NO 3
<211> LENGTH: 735
<212> TYPE: DNA
<213> ORGANISM: Homo sapiens
<220> FEATURE:
<223> OTHER INFORMATION: chromosome 5 clone CTC-222O22, complete
      sequence

<400> SEQUENCE: 3
agtcatttcc ctggatggtt tcttgcctgc actgctgaaa caacagcatc cgaactgcac      60
tgggaactgt ggaaccaccc agctccgccg ccagagaagc cggagccccg gccccccgc    120 cggcatctct gcgctgcgtt ggcctctggc tcgcaccggc tcccacctgg ctgggaacat   180
gggagtccgt ttgcccttgc cggcaggtgg ggtggctacc tgggacccta gcagggcaca   240
tctctccatc tttctgcttc tgggctttct gaaaagcttc taagtcctgg tacctcttgc   300
aactctcttc taaggatcct ttccaaagat ttcttttttcc attttttcttt tccccctgggg  360 aagctttggt tgaatatttt ctctgctttta cttcttcaac ccaacctcct ctcatcaggg   420
cttaactttt tttgcgactt gttttaactt aagatacgga atgaacacat atgtacctac   480
atacatacat aaatacaaat aggcatttat ataaatgcat atatataata gttatttttcc   540 aagagcacac ctctctggca cttttcattg atacctcggt cgtttacctg tttgggattt    600
gacaagatcc agactcagtt tggctgtgga ttttgattgc tttacaaatg gttattatta   660 ttttttttcac aagaactggg tctccagcac tcactaaggt aagctctaag acttattgct   720
tttcctgtcc agctg                                                      735

<210> SEQ ID NO 4
<211> LENGTH: 320
<212> TYPE: DNA
<213> ORGANISM: Homo sapiens
<220> FEATURE:
<223> OTHER INFORMATION: cDNA FLJ37793 fis, clone BRHIP3000473

<400> SEQUENCE: 4
aggctgaccg gttccctgat gtgttacctg cttctgctac tgatccaaac tgcagaactt      60
ctcattcatc cccaaggcct ccaggcagta tccaatgggg aatcagctct aaaaggaacc   120
agaccaacgt tttccagccc cttcattctg cttccctctg tgtgaggaaa ggatagaaat    180
gttcaggaca tcatcataca ggctcctcat ctacaaagtt ccagtagcag tgacgcctac   240
acggaagact tggaactgca aacaggctgg ggtcacctca gtgacatctg acgctgtcca   300
accagaagtt cgattttgt                                                  320

<210> SEQ ID NO 5
```

<211> LENGTH: 726
<212> TYPE: DNA
<213> ORGANISM: Homo sapiens
<220> FEATURE:
<223> OTHER INFORMATION: chromosome 1, GRCh38 Primary Assembly

<400> SEQUENCE: 5

```
taggacagaa aacctgagtt ctaattccag ctttgccagt cgtcccgtcc gtgatatatt      60
acctaactcc tccagaactc agttttctaa cctataaaat gaagacattg tgctagatga    120
tctttgtggt tccttcaagc tctggatctc taattccatg attagtaatg tatgtatgtg    180
tatataaata tgcttatctg tagaaatggg cccatttgaa aagtggagac aaggtctgcc    240
caggtgcatt tattgtgcca gaaacagtga attcctaaat aagttcataa aatcttgttt    300
tacaattcaa tggtagtgct taatgttact gtctgaaatc cactgtttaa ccagatggaa    360
gactggggcc attcaaaaca ttattagttc acaagtgttt gctgttaaaa tgcttcaata    420
aaactcattt gttaaagtca gaattcaac tcttctgtac ttgggcaggt cccagcagcc    480
ccttggcagg ctagttttgt gcatgggcct ttgcaagcta tataaacgtt aggtgttggc    540
ttgattatga taaatatgag caggctcect ggagaacagt ccagaaaaaa agagttatag    600
ttctcacaaa ctggtgacat gaatccatta agctgtgtgg cattttccag tgtaaagaca    660
ttgtttgctg gctacgatct ctgactttt gtggcatatg aggtgtaaaa tgttgtcaaa    720
aaagaa                                                                726
```

<210> SEQ ID NO 6
<211> LENGTH: 132
<212> TYPE: DNA
<213> ORGANISM: Homo sapiens
<220> FEATURE:
<223> OTHER INFORMATION: chromosome 5, GRCh38 Primary Assembly

<400> SEQUENCE: 6

```
atgacaatac ctggcaccct agagctgccc ggagaaatcc cagaactgtt ggtgatgctg     60
gggctgctcc agtaacaatc atccgcacac acccaccaag actggcctgt gggaagaaag    120
aagagctgcc aa                                                         132
```

<210> SEQ ID NO 7
<211> LENGTH: 156
<212> TYPE: DNA
<213> ORGANISM: Homo sapiens
<220> FEATURE:
<223> OTHER INFORMATION: chromosome 5, GRCh38 Primary Assembly

<400> SEQUENCE: 7

```
acacaatagc taagacccaa actgggatta gatacccac tatgcttagc cctaaactcc      60
aatagttaaa tcaacaaaac tattcaccag aacactacaa gcaatagctt aaaactcaaa    120
ggacttggcg gtgctttata tccctctaga ggagcc                               156
```

<210> SEQ ID NO 8
<211> LENGTH: 259
<212> TYPE: DNA
<213> ORGANISM: Homo sapiens
<220> FEATURE:
<223> OTHER INFORMATION: thymopoietin (TMPO), chromosome 12, GRCh38
      Primary Assembly

<400> SEQUENCE: 8

```
tttcactccc aacagtgcta gttgccgcag accaatcaaa ggggctgcag gccggccatt      60
```

| agaactcagt gatttcagga tggaggagtc tttttcatct aaatatgttc ctaagtatgt | 120 |
| tcccttggca gatgtcaagt cagaaaagac aaaaaaggga cgctccattc ccgtatggat | 180 |
| aaaaattttg ctgtttgttg ttgtggcagt ttttttgttt ttggtctatc aagctatgga | 240 |
| aaccaaccaa gtaaatccc | 259 |

<210> SEQ ID NO 9
<211> LENGTH: 805
<212> TYPE: DNA
<213> ORGANISM: Homo sapiens
<220> FEATURE:
<223> OTHER INFORMATION: voltage-dependent anion channel 1 pseudogene 2
      (VDAC1P2)

<400> SEQUENCE: 9

| cagggatgtc ttcaccaagg actatggatt tggcttaata aagcttgatt tgaaaacaaa | 60 |
| atctgagaat ggattggaat ttacaagctc aggctcagcc aacactgaga ccaccaaagt | 120 |
| gacaggcagt ctggaaacca gtacagatg gactgagtat ggcctgacgt ttacggagaa | 180 |
| atggaacacc gacaatacac taggcaccga gattacagtg gaagatcagc ttgcatgtgg | 240 |
| actgaagctg accttcgatt catccttctc acctaacact gggggggaaa aatgctaaaa | 300 |
| tcaagacagg gtacaagcag gagcacatta acttggactg cgacatagat tttgacattg | 360 |
| ctgggccttc catccggggt gctctggtgc tgggttacaa gggctggctg gccggctacc | 420 |
| agatgaattt tgagactgca aagtccagag tgacccagag caactttgca gttggctacg | 480 |
| agactgatga attctggctt cacactaatg tgaatgacgg gacagagttt ggcagcctca | 540 |
| tttaccagaa agtgaacaag aagttggaga ccgctgtcaa tcttgcctgg acagcaggaa | 600 |
| acagtaacac gcgctttgga atagcagcca agtatcagat tgaccctgac gcctgcttct | 660 |
| cagctaaagt gaacaactcc agcctgatag gtttaggata cactcagact ctaaagccag | 720 |
| gtatcaaact gacactgtca gctcttctgg atgggaagaa cgtcaatgct ggtggccaca | 780 |
| agcttggtct aggactggaa tttca | 805 |

<210> SEQ ID NO 10
<211> LENGTH: 765
<212> TYPE: DNA
<213> ORGANISM: Homo sapiens
<220> FEATURE:
<223> OTHER INFORMATION: chromosome 3, GRCh38 Primary Assembly

<400> SEQUENCE: 10

| ctgacagagt gaagtcagca gtggtaaact caacagttg aagaacaaga tggtaacaac | 60 |
| cattttaagt ggctgataac attttgtttg agatattttg atctaatttc aaagacagcc | 120 |
| ctatctcact ttgctcaatt ttaaagttag tcaattaagg gactgtatct atatctcttt | 180 |
| ttccaattag tgtctgtgtg cttggccagg catcatagcc atgcaaacta gtaaacacag | 240 |
| ttgagcagac aatggtctcc gcattctaat gccagtttga aaacttaatc ctgtcacctt | 300 |
| ggaccaacta taaagctttg aaatggagat aactcccacc atacctgtct cctattatag | 360 |
| ctttgtgcag attaactaat taaagttatg aagagattta agataaaaa ttcctgttta | 420 |
| ttattgctgt tagtcctcag agttggcacc aaatcaggaa aaaatgatat aaatcacctc | 480 |
| tgtcccaaaa ttttgcattc ttagaaatga ttcctatgaa gtatcactat aaattaggct | 540 |
| aaattgtttt ttgactgcaa gcacttacaa gctggattta tgaatggaaa catatgaagg | 600 |
| ccactctgtc cagctctgta gccccatact ttctccctgg gctatttata gaaagtgtat | 660 |

```
ggctagtgga aaagttcaca tttattttta caagccagtc atgacatgac cgaggaactc    720
atttcctctc tctgggaagg tcatcctctt cacctgagct gcaag                   765
```

<210> SEQ ID NO 11
<211> LENGTH: 689
<212> TYPE: DNA
<213> ORGANISM: Homo sapiens
<220> FEATURE:
<223> OTHER INFORMATION: TAF5-like RNA polymerase II

<400> SEQUENCE: 11

```
tcttgttctg aagacatgtc catcagatac tgggatctgg ggagtttcac caacactgtg     60
ttgtaccaag gacatgccta tcctgtgtgg gatctggaca tcagtccata tagcctgtac    120
ttcgccagcg gtcccacga ccgcaccgcc aggctgtggt catttgatcg gacgtacccg    180
ctgaggatat atgcaggaca cctggcagat gtggactgtc tcaaattcca ccctaattca    240
aactacttgg ccacgggctc aaccgacaag accgtccggc tgtggagcgc tcagcagggg    300
aactcggtga ggcttttcac aggccaccgt ggccccgtgc tttctctcgc cttttctccc    360
aacggtaagt acttggcgtc tgctggcgag gaccagcggt tgaagctgtg ggacttggcc    420
tctgggaccc tttataaaga gttgagaggc cacacagaca atatcaccag cctcaccttc    480
agtccagaca gcggcttgat tgcctctgcc tccatggaca actcggtgcg cgtctgggac    540
atcaggaaca cttactgcag tgcacctgcc gacggctcct ccagcgagct cgtgggcgtg    600
tacaccgggc agatgagcaa cgtcctgagc gtgcagttca tggcctgtaa ccttcttctg    660
gtgactggaa ttacacaaga aaatcagga                                      689
```

<210> SEQ ID NO 12
<211> LENGTH: 1598
<212> TYPE: DNA
<213> ORGANISM: Homo sapiens
<220> FEATURE:
<223> OTHER INFORMATION: H19

<400> SEQUENCE: 12

```
aggcctgggt cagacaggga catggcaggg gacacaggac agaggggtcc ccagctgcca     60
cctcacccac cgcaattcat ttagtagcag gcacaggggc agctccggca cggctttctc    120
aggcctatgc cggagcctcg agggctggag agcgggaaga caggcagtgc tcggggagtt    180
gcagcaggac gtcaccagga gggcgaagcg gccacgggag gggggccccg ggacattgcg    240
cagcaaggag gctgcagggg ctcggcctgc gggcgccggt cccacgaggc actgcggccc    300
agggtctggt gcggagaggg cccacagtgg acttggtgac gctgtatgcc ctcaccgctc    360 agccctgg gctggcttgg cagacagtac agcatccagg ggagtcaagg gcatggggcg    420
agaccagact aggcgaggcg ggcggggcgg agtgaatgag ctctcaggag ggaggatggt    480
gcaggcaggg gtgaggagcg cagcgggcgg cgagcgggag gcactggcct ccagagcccg    540
tggccaaggc gggcctcgcg ggcggcgacg gagccgggat cggtgcctca gcgttcgggc    600
tggagacgag gccaggtctc cagctggggt ggacgtgccc accagctgcc gaaggccaag    660
acgccaggtc cggtggacgt gacaagcagg acatgacatg gtccggtgtg acggcgagga    720
cagaggaggc gcgtccggcc ttcctgaaca ccttaggctg gtgggctgc ggcaagaagc    780 gggtctgttt cttttacttcc tccacggagt cggcacacta ggctgccct ctgggctccc    840 agaacccaca acatgaaaga aatggtgcta cccagctcaa gctgggcct ttgaatccgg    900 acacaaaacc ctctagcttg gaaatgaata tgctgcactt tacaaccact gcactacctg    960
```

```
actcaggaat cggctctgga aggtgaagct agaggaacca gacctcatca gcccaacatc    1020
aaagacacca tcggaacagc agcgcccgca gcacccaccc cgcaccggcg actccatctt    1080
catggccacc ccctgcggcg gacggttgac caccagccac cacatcatcc agagctgag    1140 ctcctccagc gggatgacgc cgtccccacc acctccctct tcttcttttt catccttctg    1200
tctctttgtt tctgagcttt cctgtctttc cttttttctg agagattcaa agcctccacg    1260
actctgtttc ccccgtccct tctgaattta atttgcacta agtcatttgc actggttgga    1320
gttgtggaga cggccttgag tctcagtacg agtgtgcgtg agtgtgagcc accttggcaa    1380
gtgcctgtgc agggcccggc cgccctccat ctgggcgggg tgactgggcg ccggctgtgt    1440
gcccgaggcc tcaccctgcc ctcgcctagt ctggaagctc cgaccgacat cacggagcag    1500
ccttcaagca ttccattacg ccccatctcg ctctgtgccc ctccccacca gggcttcagc    1560
aggagccctg gactcatcat caataaacac tgttacag                             1598

<210> SEQ ID NO 13
<211> LENGTH: 339
<212> TYPE: DNA
<213> ORGANISM: Homo sapiens
<220> FEATURE:
<223> OTHER INFORMATION: ARP3 actin-related protein 3 homolog (yeast),
      mRNA

<400> SEQUENCE: 13
atggcgggac ggctgccggc ctgtgtggtg gactgtggca cggggtatac aaaactagga     60
tatgctggaa atacagaacc acagtttatc atcccttcct gtattgctat taaggagtca    120
gcaaaagtgg gtgatcaagc tcaaaggagg gtgatgaaag gtgttgatga cctagacttc    180
ttcattggtg atgaagcaat agaaaaacct acatatgcaa caaagtggcc aatccgccat    240
ggtatagttg aagattggga cttaatggaa aggtttatgg agcaagtgat ctttaaatat    300
ttaagggcag aacctgaaga ccattatttt cttttgact                            339

<210> SEQ ID NO 14
<211> LENGTH: 923
<212> TYPE: DNA
<213> ORGANISM: Mus musculus
<220> FEATURE:
<223> OTHER INFORMATION: Gm11641

<400> SEQUENCE: 14
ctcagcgcca tcctcccaa cgccattccc ccctcagtcc agcccggccc gggcaccta      60 gaactttcgc ccgctggcct agcttccact tgtcccggca gacgcgcgtg gggtccgcgt    120
ccggagctgc ctgctccaca gccctgctcc ggcgatgccc tgtttcctgt tcaacaatat    180
aaccggcgga gagcgctcgg cagaacttcc tcccaagccg ggactgggct gtgcttgcaa    240
gagacaatcc ccggtgtcct ggcttcctgt cccctctggg ccgggccagc gctctaggag    300
cagagacgcc accctccccc ctcttcccca ggatcctggg ccacacctga ctgtctccgg    360
ggaggaggcg gtggcagggc ctggatggag atctgcgggg gaggcagttt ctctcagctt    420
ctgaccagat tagactccca ctgaccctca tccttgtcgg aggaagtcac cggccactct    480
gcaggcggcc gaagtgcagt tgcgggatcc tcccattttg gaaactacct gcctcttggg    540
aaagcagcct tagcactctg aggtgtgcct gtgaacactt ctgacaaagg aggcactttc    600
tggggatgag aactccagtt tgcccatccc cctctagaca ggggaaaggg gaaactgccc    660
tcagaggcac tgtgctgaag gtggaaagac aaccaaagac agcagcagca gcagcgcaag    720
```

```
tgccaggcgc ctcccccggg cctgccaccc ccaacctcca aatccagttc ctctcccttt      780
gctctgagcc ctgagaacct gcctcaaaga tggccaagga gcacccaccc actggctgag      840
ggcgctcaag gccaggaaac gaagccctgg atgttgtctt tttctgtccc attttctgc       900 aacctggttt ccctaggaat taa                                              923

<210> SEQ ID NO 15
<211> LENGTH: 937
<212> TYPE: DNA
<213> ORGANISM: Mus musculus
<220> FEATURE:
<223> OTHER INFORMATION: Gm16192

<400> SEQUENCE: 15
cagataccaa cctcccaagt cagtgtgagg ctatcaaaga cttccgtagg tttgcgtctg       60
gctaacctac catcggaaag atttggtggc agaggagagc gccagaaagt tccaaggcaa      120
ccatcctgca tcggtaaaca cagacaagcc tacagctgcc ggcacacaac taaagtaccc      180
tcctgcccaa cacaggagat taccgctcct tgtaaccagt caagcctctc cttaaagagg      240
gctttagtgc ccaattatgt ctccatagaa acctgagaag catgagcaag ttcatcagca      300
tatctccgac ctcccctccc cgcgcgcggt gctgagcaga cctgtgcagg accaacctgt      360
gtggaaaatg acagtgtttt tcctgagccc cgaaggaagc cggaggtttc gaagcagtcc      420
tttggcggtt aggcggacgt ggatggtgga taaggagaat ttgggagaca acagcatgtc      480
ttcgaagcca gtgggagaac ttcgcagggg aagcagcttt tccagggacc atcacatact      540
gtgtctcttg gcaactcggg gttcttccag gccaagagat acagccagag aaaaacaagc      600
ttacatgcta atgccaggcc acccagattg ggggtgcgt ggggggggg gtagctagag         660 ttagctatcc cagagctcca ggcttccgtt tgctcttcca gatgttgcta acaaacaatg      720
cccttcgtct gagcaagatc tgtgaggagc agctcaggaa gcaagcagcc tgaattacat      780
cacactgtgc atgccgcggg ttgttgtggt tcccgactgg gatggaaagg ggaggagaaa      840
gtgggtggtc tcgggagctt tatgtaacag ccaatgatgt cgcaggtcct gtcactattt      900
ggaacggggc gaaatgaaat aaaccacctc acatgcc                               937

<210> SEQ ID NO 16
<211> LENGTH: 725
<212> TYPE: DNA
<213> ORGANISM: Mus musculus
<220> FEATURE:
<223> OTHER INFORMATION: AK013700

<400> SEQUENCE: 16
gagtcatttc cctggatggt ttcttgcctg cactgctcac acaacagcat ccgaactgct       60
cctggcaccg tgggacctct cagcttcgga gcccaagccc cgcaggcatc tctcgccttc      120
ccggctgctt ttccttccca cctggcgggg acatgggcgt ccctttgccc ttgcctgcag      180
gtggggtggc tgctgcaacc ctgggggggcg catctatctg tcgccctgcc tctgggctct      240
ctgaatgcct ctaagtccag gtacctcttg caactcttcc aggtgcaaag gatttatctg      300
ttctataagg tttggatttc gtttttttctt ttttcctac ggaagctttg gttgaatata      360
tatatttttt tcctctgctc cacttcttcg actcagcatc ctctcggttc aacttttttc      420 cccccgatt cgtttagct agagattaga tgtgaatgca tacacccatt catcacacaca      480 tagaaacgta cacctactag agcttaagtg tggaatcatt gttttccgag agcaccaatc      540
```

| | |
|---|---|
| tcttgacact tttcatcgat acctctgtcc tttacctgtt tgggatttga caagacgtcc | 600 |
| aggctcagtg tgtggctgtg gtttctgatt gctctggaaa aggttatttc ttcgcaagaa | 660 |
| ctgagtctcc agcactcact cgctaaggta agcgcagaga ctcactgctt tctctgtcct | 720 |
| gctgc | 725 |

```
<210> SEQ ID NO 17
<211> LENGTH: 439
<212> TYPE: DNA
<213> ORGANISM: Mus musculus
<220> FEATURE:
<223> OTHER INFORMATION: Gm15892

<400> SEQUENCE: 17
```

| | |
|---|---|
| agaccttgaa gggaatcttc taaggcaggg aagaagcaga gacttgtatc cactgaacca | 60 |
| aaatacaagc acatactatg tccaaggctg accagttctc tggtggttcc tgctactgat | 120 |
| ccatccaaac tgctggactt gtccttcata cccaaggtct tcaggcagta tctaatggga | 180 |
| agtcaactct aaaaggaacc agactgtcat ttcctggccc ctttattctg tagctacctc | 240 |
| tatgtgagga aaggatagaa acattcaag acatcatatg gcttacgat ctacagattc | 300 |
| caaccagtag cagtggctga ctcctacaca gacgactggg aactgcaaac aggctggggt | 360 |
| cacctcagtg acatctgacg ctgtccaacc agaagtctga cttgtgtgtg cgtgtgctgc | 420 |
| aggaattgaa aaatgtact | 439 |

```
<210> SEQ ID NO 18
<211> LENGTH: 1726
<212> TYPE: DNA
<213> ORGANISM: Mus musculus
<220> FEATURE:
<223> OTHER INFORMATION: BC023483

<400> SEQUENCE: 18
```

| | |
|---|---|
| atttaggttc ctatgcctta cttgaattct gtccttcccc ccataactgc agctgttgat | 60 |
| agattttaca atcctaataa atctgtatgt ttttcttact ccagcgatgt ctattagcag | 120 |
| agacatgggc cagggaaggg tgatggatac agccaggggt gggatatcag cctcaaagtg | 180 |
| cagagctttg ctctgaatct cagcaggcag ccaaagggac tgagacaaag ctcttccttt | 240 |
| caagttggca tggcaatcaa cttggaaatc aggttccccg ggcctttgcc ttcctaacaa | 300 |
| aggatccagc ctcctccaac tgggtctcca ctcagcccct gtagaaaagt gctgacagta | 360 |
| ttaagttcta ctcttcccta agaccccagg aggtcctcac cgtgcataga tgtgccatct | 420 |
| gttcttgaga aaccaaagca ctttagtgag tcttacaacc cataatactt acagtatttg | 480 |
| ccctctgaaa ggtggaaggg gcttgggcta ggtctcattt gagaggcaac tagagctagg | 540 |
| aggaaaagcc tggagctaga cagcagggag ctaagccaca tctgcaccac cacaagctat | 600 |
| gaacctcggg taggttgctg aatttttgctg ccccccccc cctagacagt tgtggggagg | 660 |
| tcctaacagc taccctcctg ggatggcaga aaaggaaggg aataatataa ctggtgggac | 720 |
| acgctttgaa gaaatcagaa gctctctcca gaggggaggg aggatcatgt atagatgaag | 780 |
| aagttgacat ccgtactcac tgcctggcca ggttcacagt ctcacagcag aactgggaca | 840 |
| tgagccccgc cacctggagt gtccctgata gagcaccttt cacccagagt gtgtacatga | 900 |
| acacaggctg cttctctgtg ccagtgtgtg cacatatgtg ggtgtgtctg tatgggggt | 960 |
| gtgtgcagca cagatgaacg taggacagaa actccgagtc ctaattcctt tctaacagtc | 1020 |
| gacctgtctg tggcctggga cacacaacca actcttctgg acctcagatt ttctaagtca | 1080 |

```
taaaacaagg acattgtggc atgggatctt tgtggttctt ccaactttgg tgacgagagc    1140
ccctaacggg tgatgtatgt atgtatatat cgatatgctt atctgtagaa acgggcccat    1200
tgggaaattg gagacgaggc ctgcccgagt gcattgactt gtaacagaat cggcaacttc    1260
acaagtccgt aagccttcat tttaaaagtc gatgggatgg tgtcatttac tgtcattgtt    1320
tcaaattcac tgttgaactg ggtagaggat tggtgctgtt ttaaaaacta agttcttagc    1380
tcacaagtgt ttgctgttac ttttcaaaac acgagtcatt tgttcaaaag tcaaactttt    1440
aactctgcct tgggcaggtc cccaacagcc tgttttgcag gctgggtttt gtgtatgggc    1500
ttttacataa ctatataaaa gttagctgtt ggcttgatca tggtaaatat gaacagattg    1560
cctggagaac agtccagaaa agaattgaat tctatagttc tcatcaactg gtgacatgaa    1620
accattaagc tgtgtgcaat tccctggtgt gaagatattg ttcactggct acagtctctg    1680
actttgtggc atatgaggta taaatgttg taaaaaaaaa aaaaaa              1726

<210> SEQ ID NO 19
<211> LENGTH: 567
<212> TYPE: DNA
<213> ORGANISM: Mus musculus
<220> FEATURE:
<223> OTHER INFORMATION: Gm12224

<400> SEQUENCE: 19
gggctttgtt tctttctcct ttgcagaaag gccactgggc tgatagtgtc ctcttagcaa      60
gtaagcttgc ctgcagctgc taagacagca gtgcccataa aagtaaaaat aagcatcacc     120
atgtcatcca gaatggcttt cttcaattcc tgaattgaac catgtccagt agttgagttc     180
ctctgcatcg accagcttga tgtggttgca gggcagaggt gccctacat gcctaggac      240 accagaacaa gagtgaaagg cttgggcctc tggcatcttc ctctgtaccc ggctgcccag     300
cacacgtccc accacccca aggaaggcc gggatgatga tacctggcac cccagagctg      360
ctcgtaggaa tcccagaacc gttggtgacg cggggctgc tccagtgaca atcatcctca      420
catgcccacc aagactggcc tgtgggaaga aagaagctgc caatgatggt gacacacgag     480
atggtcttca tttatggtct gctttcaaca gctggaccct gggtgctaga agagagccac    540
gtgctgagga agtcgcttct cttttgt                                         567

<210> SEQ ID NO 20
<211> LENGTH: 292
<212> TYPE: DNA
<213> ORGANISM: Mus musculus
<220> FEATURE:
<223> OTHER INFORMATION: AJ409495

<400> SEQUENCE: 20
ggctcctcta gatggatata aagtaccgcc aagtcctttg agttttaagc tatggctagt      60
agttctctgg caaatagttt tgttaaattt aattatttag gttatggct aagcatagtg      120 gggtatctaa tcccagtttg ggtcttagct gtcgtgtatt ataaatgact agaattactt     180
tcgttattga gtttaggtcc taacaatgaa ttttcacata taagttggat tttaattcta    240
tttatttatt tatagttgac acgttttacg ccgaagataa ttagtttggg tt             292

<210> SEQ ID NO 21
<211> LENGTH: 692
<212> TYPE: DNA
<213> ORGANISM: Mus musculus
<220> FEATURE:
```

<223> OTHER INFORMATION: Gm17499

<400> SEQUENCE: 21

| | | | | | |
|---|---|---|---|---|---|
| gggatttcct | tggttggttt | ccatagcttg | atagaccaaa | acaaaaaaca | cggccacaag | 60 |
| ggcaaacagc | aacattttta | tccacatggg | aacggagcgt | ctcttctttg | tcttttctga | 120 |
| cttgacatct | gccaagggag | catacttcgg | gacgtactta | gatgagaacg | actcttccat | 180 |
| cctgaagtca | ctgagctcga | gcggccggcc | tgcagcacct | ttgattggtc | tgcggcagct | 240 |
| agcactgttc | aaagtgaaac | agaattccag | atgattcaag | tcaacaacca | aaccttagtg | 300 |
| tgatttctaa | gcacactgca | aaatgcagca | gcagaaaatc | gtcagataaa | agcaggggat | 360 |
| tgacgtatca | catgcttttc | tttgtttgtt | ttgttttttg | agacagggtt | tctgtgtacc | 420 |
| cttggctgtc | ctggaactca | ctctgtagac | cagggctgtt | atagagcaac | catgtttcga | 480 |
| atactccaaa | aagttagctg | tatcatatta | taaaatagta | tttaggataa | atactctcta | 540 |
| agcctgtctt | ggaggctgag | tagtgtactg | tgtgcctgta | atcgcagcac | ttgggaagtg | 600 |
| tgtcatgagt | ctaacatctg | ccttgcatat | agggtaaatc | caagatcagc | ctggtgactt | 660 |
| gagaacttgt | ctcaaaaaag | aaaataaaac | tt | | | 692 |

<210> SEQ ID NO 22
<211> LENGTH: 760
<212> TYPE: DNA
<213> ORGANISM: Mus musculus
<220> FEATURE:
<223> OTHER INFORMATION: Gm8459

<400> SEQUENCE: 22

| | | | | | |
|---|---|---|---|---|---|
| atccatcagg | gatgtcttca | ccaagggcta | ccgctttggc | ttaataaaac | ttgatttgaa | 60 |
| aacgaagtcc | aagaatagat | tggaatttac | cagctcaggc | tctgccaaca | cggagaccac | 120 |
| cagagtgaac | ggcagtctgg | aaaccaagga | cagatggact | gagtatgggc | aaacatttac | 180 |
| ggagaagtgg | aacacagaca | gcaccctggg | cactgagatc | accgtgggag | accagccttgc | 240 |
| ttgtggactg | aagctgacct | tcgattcatc | tttttcaccc | aaaacttggg | ggaaaatgct | 300 |
| aaaaatcatg | acagggtaca | agagggagca | catcaacttg | gctgtgtggcg | tggactttga | 360 |
| catcgctggg | ccctcaatcc | ggtgcttggc | tatgagggtt | ggctagctgg | ctaccagatg | 420 |
| aattttgaga | cctcgaagtc | ctgagtgacc | cagagcaaga | cagcttcata | cgacgggaca | 480 |
| gagtttggtg | gttccattta | ccagaaggcg | aacaagaagt | tggagactgc | tgtcaatctc | 540 |
| gcctggactg | cagaaaacag | taacactcgc | tttggaatag | cagccaaatt | tcagttccac | 600 |
| cctgatgcct | gcttttctgg | caaagtgaac | aactccagcc | tgattggctt | agggtacact | 660 |
| cagatcctaa | aaccaggtat | caaactgaca | ttgtcagccc | tactggacgc | aagaacatca | 720 |
| atgctggcag | acacaagctt | ggcttaggac | tagaatttca | | | 760 |

<210> SEQ ID NO 23
<211> LENGTH: 2759
<212> TYPE: DNA
<213> ORGANISM: Mus musculus
<220> FEATURE:
<223> OTHER INFORMATION: AK083183

<400> SEQUENCE: 23

| | | | | | |
|---|---|---|---|---|---|
| ggagacccct | tctcctttct | cagcttgcca | ctcaggtgaa | gaagatgacc | ttcccagaga | 60 |
| gaggaagtac | agactccttc | atgtcatgac | tggcttgtaa | aaataaacat | gatcttttc | 120 |
| cactggccat | acacgttcca | taaatagccc | agggagaaag | tacggggcta | cataactgtc | 180 |

```
cagagtggcc ttagactgct tccattcata aacccactg taagtgctca cagtcagaaa    240
accacgtagc ctaatctgat gggcaacttt atatatgggg gaactattgc taagaatatc    300
aaactggtaa gttttctga ttgagtgatg ggtctgaggg gctgacagca acaagccagg    360
ggttttaacc ttccactccc ccagctagta tatctgctca aagctatagt cgacaggtat    420
ggttgaagtt gcttttaag ggttttatca ttggctgaag gtgacagaat tcagtcttca    480
aactgatagt gaaagcaggg acagctgtgt gctcagctgt gtctattact ctgcaggact    540
atgttgcatg gtcaagtata cagatgctga ttggatatat tgtgtgtaat catggataag    600
atatccttta attgaataca tctattcagt tttaaaatag atcaaaataa gagacgggaa    660
cctttaaaat tagattatag gatcttaaaa tgtcaccagc caccgagatg atttctgtca    720
ccttgttctt tatccattaa gtttgccatt gctgattgac tccgttaggc tcctttggct    780
gatgcctacc tagtcttcaa tgtgatcttc ctagtgctta ctgaacattt actctacgta    840
aggcactaag caacgatcca tgtatccatc cacgtaattg ccttttggtc ttacagcaga    900
gcagagtaga agtttgagtt ttttctcctg ttggtataag atcagtctcg cacagtaata    960
gacccacagc gttttacttt tctccttagc ttaaagcttt ttttaaaatt taatttacaa   1020
ttcaggtata agaagagtgt gtctatgaac agagtttaat gttttatcat catggtaatg   1080
acagtagtaa cgatgaactg ctggaaggtt atggcgtcca catcatttcg aagagtggtt   1140
tgctcagagt gcctacaaca gacagtgtag tgaagtcaaa gcaagattcc actcaggcag   1200
gtgtttggag agtttagctt atgcttaact ctccaaaaat cttctggcct ttgcctgccc   1260
tcttcttaga tccttccatt ataacgagag agagagagaa ttggattcag acagccaacg   1320
tggaacagct gctcaactcc ggacagtgtt acctgatttt aagttctgtc cctagaaaag   1380
ctttcggact ctgagggtgt ccgtgctcaa acaggtggca agggattcta tttggcatcc   1440
taacaccacc ctgcagcttt tgacggcagc tctgcgtgcc gtgggatatt ttgagtagta   1500
catttatcct gtggcttaat ttgtttccat aaaattaggg cataggtcaa aaaggcatta   1560
gaggctaatt gtgaaggaca ttttaagtca ttttcttaaa ggattgtcag catttgttga   1620
catgtactgc cagacaaaag caaaggagcc tagacccctg ggaaaggaag ccccagatgg   1680
ctgaaaccgg cattgtagcc attcctttag gaggggccac aggccttcct actgaagtgt   1740
tgaggtcttt gatattgtca ataatttttt tcttaattac aaaatgacta tcagtactta   1800
gtaatcaaaa aaacctaaca taaattcctg ttacttctca gagaacaaat gtattgcatt   1860
tctagtttgt ggatttctca cgaatttgta gggttttttt ttttcttttc tttccttttc   1920
tctttctttc ctttccttt cttttctttt actttatttt atttttgtg gtagcttctt   1980 acacagtctg tgagcaagct tcagaactgg ctagttaagt tataggtggg acccccaagt   2040
gctcacttag ctagtcatag tggcagggtg ggacacacac ctgtatgcaa caacccgcag   2100
ttactatttg gtgcaggagg agagcagccc cttctttaag cttttagaag tacctgtccc   2160
ccaccctgtg ttaagcttcg gaatgtaaca gagacgcttt aatgcttttt gttccaaaca   2220
tgacatttcc caaggaaata tcttgagtgt acaattccat tctcgaatgt ggaaagtgg   2280 caggccacct tccccacgcc ttacagttcc accccaaata tgcagtaagc acgcgcagtg   2340
aaggccgggt cgggaggagc cttcggatgg ttatttagcc gtgcagtaaa gaccctgctt   2400
ctcctggctc accaccactc cgaggtgggc aggacaccac ggcagtgaac cctgcttctg   2460
ggtgaagtac agggacacac ttcgcttctt tcacttcttc ttttggttcc atctctattt   2520
```

| | |
|---|---|
| aaaaagtata gtcttttttt ttttaacttg ctggatgtgg aaaaaaatgc atggtaaaaa | 2580 |
| aaaaatttaa agacatattt taattttata tttcaaaggt ttgtaatagc agtttgtttg | 2640 |
| ttaaaaacag gccttagcac atggatgaga accagggctt tttcaaaagc ctcatctttg | 2700 |
| agctcttacc caaatgataa agacctcttg gatctttcaa actgtaaata ttgtgtagt | 2759 |

<210> SEQ ID NO 24
<211> LENGTH: 691
<212> TYPE: DNA
<213> ORGANISM: Mus musculus
<220> FEATURE:
<223> OTHER INFORMATION: Gm13316

<400> SEQUENCE: 24

| | |
|---|---|
| aatcatgttc tgaagatatg tccatcagat actgggacct ggggagcttc accaacactg | 60 |
| tgctgtatca gggacatgcc taccctgtgt gggacgtgga catcagcccc ttcagcctgt | 120 |
| actttgccag tggatcccat gaccgtaccg ccaggctgtg gtcttttgat cggacgtacc | 180 |
| cgctgaggat atatgcagga cacctggcag atgtggactg tgtcaaattc caccccaact | 240 |
| caaactactt agctacaggg tccactgaca aaactgttcg gctatggagt gcccagcagg | 300 |
| ggaactcggt gcggctcttc acaggtcacc gaggccccgt gctctccctc tccttttctc | 360 |
| ccaatggtaa gtacttggca tctgctggtg aggaccagcg gttaaagttg tgggacttgg | 420 |
| cctctgggac acttttttaaa gaactgagag gccacacgga cagcatcacc agtctggcct | 480 |
| ttagcccgga cagcggtctg attgcttctg cctccatgga caactccgtg cgtgtctggg | 540 |
| acatcagaag catgtgctgc aacacacctg ctgacggctc ttcaggtgag cttgtgggcg | 600 |
| tgtacactgg gcagatgagc aacgtcctga gtgtacagtt catggcttgc aaccttctcc | 660 |
| tggtgactgg aatcacacaa gagaatcaag a | 691 |

<210> SEQ ID NO 25
<211> LENGTH: 2615
<212> TYPE: DNA
<213> ORGANISM: Mus musculus
<220> FEATURE:
<223> OTHER INFORMATION: H19

<400> SEQUENCE: 25

| | |
|---|---|
| accgggtgtg ggaggggggt gggggtgggg ggtgggggggt atcggggaaa ctggggaaga | 60 |
| tgggagagct ggaggagagt cgtggggtcc gaggagcacc tcggcatctg gagtctggca | 120 |
| ggaatgttga aggactgagg ggctagctca ggcagagcaa aggcatcgca aaggctggaa | 180 |
| aacatcggag tgaagctgaa gggcctgagc tagggttgga gaggaatggg gagccagaca | 240 |
| ttcatcccgg ttacttttgg ttacaggacg tggcggctgg tcggataaag gggagctgct | 300 |
| gggaagggtt cgaccccaga cctgggcagt gaaggtatag ctggcagcag tgggcaggtg | 360 |
| aggaccgccg tctgctgggc aggtgagtct ccttcttctc tcttggcctc gctccactga | 420 |
| ccttctaaac gaaggtttag agaggggggcc tggtgagaag aagcggctgg cctcgcagca | 480 |
| gaatggcaca tagaaaggca ggatagttag caaaggagac atcgtctcgg ggggagccga | 540 |
| gacagaagga ggctggggga ccattggcga ccccaggtgg aaagagctct tagagagaag | 600 |
| aaagaagagg tgcagggttg ccagtaaaga ctgaggccgc tgcctccagg gaggtgatag | 660 |
| gagtccttgg agacagtggc agagaccatg ggatccagca agaacagaag cattctaggc | 720 |
| tggggtcaaa cagggcaaga tggggtcaca agacacagat gggtccccag ccgccacaac | 780 |
| atcccaccca ccgtaattca cttagaagaa ggttcaagag tggctctggc aaagtcccaa | 840 |

```
gtttgccaga gcctcaataa ctggagaatg gaaaagaagg gcagtgcagg gtgtcaccag      900
aaggggagtg ggggctgcag gtatcggact ccagagggat tttacagcaa ggaggctgca      960
gtgggtccag cctgcagaca caccattccc atgaggcact gcggcccagg gactggtgcg     1020
gaaagggccc acagtggact tggtacactg tatgccctaa ccgctcagtc cctgggtctg     1080
gcatgacaga cagaacattt ccaggggagt caagggcaca ggatgaagcc agacgaggcg     1140
aggcaggcgg ggcagaatga atgagtttct agggagggag gttgggtgca ggtagagcga     1200
gtagctgggg tggtgagcca gggaggcact ggcctccaga gtccgtggcc aaggagggcc     1260
ttgcgggcgg cgacggagca gtgatcggtg tctcgaagag ctcggactgg agactagggt     1320
aagtgtctgt cccgctcgtg gtcacccagt ctcctcccac gcaagttcaa ttaactcatg     1380
tcttcatttc tccctatagc caggtctcca gcagaggtgg atgtgcctgc agtcactga     1440 aggcgaggat gacaggtgtg gtcaatgtga cagaaagaca tgacatggtc cggtgtgatg     1500
gagaggacaa aagggcagtc atccagcctt cttggtgagc atactccctg ccacagggct     1560
agtccgctca accacctaat tgtccaccca ctcactcagg attctgtcct tgcagaaca      1620 ccatgggctg cgcgccttgtc gtagaagccg tctgttcttt cacttttccc aaagagctaa    1680
cacttctctg ctgctctctg gatcctcctc ccctaccttt gaaccctcaa gatgaaaggt     1740
gagttctctt ctgccccatg tgggtgggag agggtgggat gccaaggaca ggggtctcat     1800
tctctcccac ccatagaaat ggtgctaccc agctcatgtc tgggcctttg aatccgggga     1860
cttctttaag tccgtctcgt tctgaatcaa gaagatgctg caatcagaac cactacacta    1920
cctgcctcag gaatctgctc caaggtgagc tggggcaccc tttggaagct tgccaagccc     1980
actccccacc ccacccccg ccccacctca tttgtctta ttctctttgc aggtgaagct       2040
gaaagaacag atggtgtcaa catttgaaa gagcagactc atagcaccca cccaccctg       2100 agaatccatc ttcatggcca actctgcctg acccgggaga ccaccaccca catcatcctg     2160
gagccaagcc tctaccccgg gatgacttca tcatctccct cctgtctttt cttcttcct      2220 cctttcctgt aattctgttt ctttcctttt gttccttcct tgcttgagag actcaaagca     2280
cccgtgactc tgtttcccca tttaccccct tttgaatttg cactaagtcg attgcactgg     2340
tttggagtcc cggagatagc tttgagtctc tccgtatgaa tgtatacagc gagtgtgtaa     2400 acctcttttgg caatgctgcc ccagtaccca cctgtcgtcc atctccgtct gagggcaact    2460
gggtgtggcc gtgtgcttga ggcctcgcct tcccctcgcc tagtctggaa gcagttccat     2520
cataaagtgt tcaacatgcc ctacttcatc ctttgcccct cctcaccagg gcctcaccag     2580
aggtcctggg tccatcaata aatacagtta cagtc                                2615
```

<210> SEQ ID NO 26
<211> LENGTH: 339
<212> TYPE: DNA
<213> ORGANISM: Mus musculus
<220> FEATURE:
<223> OTHER INFORMATION: Gm8822

<400> SEQUENCE: 26

```
atggcgggac ggctgccggc ctgtgtggtg gactgtggca cgggatatac aaaactagga      60
tatgctggaa atacagagcc acagtttatc atcccatcat gtattgccat taaagagtct     120
gcaaaagtgg gtgaccaagc ccagaggagg gtgatgaaag gcgtggatga cctagacttc     180
ttcattggtg atgaaacaat agaaaagccc acatatgcaa caaagtggcc aattcgccat     240
```

```
ggtatagttg aagactggga cttaatggaa aggtttatgg agcaagtgat ttttaaatat    300
ttaagggcag aacctgaaga tcattacttt cttttgact                          339
```

```
<210> SEQ ID NO 27
<211> LENGTH: 366
<212> TYPE: DNA
<213> ORGANISM: Homo sapiens
<220> FEATURE:
<223> OTHER INFORMATION: chromosome 17, GRCh38.p2 Primary Assembly

<400> SEQUENCE: 27
cctgcccggg cacctcgggg cgtccgctcg ccggcctcgt ctccacttgt cccggcaggc    60
gcgcgtgggc tcggcgtccc gcgctccctc ctcgaccgcg cggctccggc gctgccaggt   120
ttcctgtata gcactataac cagtgaggca ccggcggaga gcgcccggca gaacttcctc   180
ccggactggg gctgggctgc ggttgcgaga gacaatcccc ggcgtcctgg cttcctgtcg   240
cctctgggcc aggcccgcgc ctgaagagga aagatgccac cccctcccct gcatttcccg   300
ggatcctggg ccactcccgg gatcctggct gtctccaggg aggaagaggc cgcggggctg   360
agatgg                                                              366
```

```
<210> SEQ ID NO 28
<211> LENGTH: 358
<212> TYPE: DNA
<213> ORGANISM: Homo sapiens
<220> FEATURE:
<223> OTHER INFORMATION: chromosome 17, GRCh38.p2 Primary Assembly

<400> SEQUENCE: 28
cctgcccggg cacctcgggg cgtccgctcg ccggcttcgc ctccacttgc cccggcaggc    60
gcgcgtgggc tcggcgtccc gcgctccctc ctcgactgtg cggctcccgc gctgccgggt   120
ttcctgttca acaatataac cagggaggca ccggcggaga gcgccgggca gaacttcctc   180
ccggactggg gctgggctgc ggttgcgaga gacaatcccc ggtgtcctgg cttcctgtcc   240
cctctgggcc gggccagcgc ctgaggagcg aagacgccac cccctcccct gcctttcccg   300
ggatcctggg ccgcacctgg ctgtctccag ggagaaagag gctgcgggc tgagatgg     358
```

```
<210> SEQ ID NO 29
<211> LENGTH: 20
<212> TYPE: DNA
<213> ORGANISM: Artificial Sequence
<220> FEATURE:
<223> OTHER INFORMATION: H19 human forward primer

<400> SEQUENCE: 29
agacagtaca gcatccaggg                                               20
```

```
<210> SEQ ID NO 30
<211> LENGTH: 18
<212> TYPE: DNA
<213> ORGANISM: Artificial Sequence
<220> FEATURE:
<223> OTHER INFORMATION: H19 human reverse primer

<400> SEQUENCE: 30
gagacctggc ctcgtctc                                                 18
```

```
<210> SEQ ID NO 31
<211> LENGTH: 20
<212> TYPE: DNA
<213> ORGANISM: Artificial Sequence
```

```
<220> FEATURE:
<223> OTHER INFORMATION: H19 mouse forward primer

<400> SEQUENCE: 31
gaacatttcc aggggagtca                                                  20

<210> SEQ ID NO 32
<211> LENGTH: 23
<212> TYPE: DNA
<213> ORGANISM: Artificial Sequence
<220> FEATURE:
<223> OTHER INFORMATION: H19 mouse reverse primer

<400> SEQUENCE: 32
acacttaccc tagtctccag tcc                                              23

<210> SEQ ID NO 33
<211> LENGTH: 20
<212> TYPE: DNA
<213> ORGANISM: Artificial Sequence
<220> FEATURE:
<223> OTHER INFORMATION: CHAST (L302) human forward primer

<400> SEQUENCE: 33
gcagagggtg ccaacttgta                                                  20

<210> SEQ ID NO 34
<211> LENGTH: 22
<212> TYPE: DNA
<213> ORGANISM: Artificial Sequence
<220> FEATURE:
<223> OTHER INFORMATION: CHAST (L302) human reverse primer

<400> SEQUENCE: 34
tctcagggaa atcagattgc gg                                               22

<210> SEQ ID NO 35
<211> LENGTH: 20
<212> TYPE: DNA
<213> ORGANISM: Artificial Sequence
<220> FEATURE:
<223> OTHER INFORMATION: CHAST (L300) human forward primer

<400> SEQUENCE: 35
cggttgcgag agacaatccc                                                  20

<210> SEQ ID NO 36
<211> LENGTH: 19
<212> TYPE: DNA
<213> ORGANISM: Artificial Sequence
<220> FEATURE:
<223> OTHER INFORMATION: CHAST (L300) human reverse primer

<400> SEQUENCE: 36
aggatcccgg gaaatgcag                                                   19

<210> SEQ ID NO 37
<211> LENGTH: 20
<212> TYPE: DNA
<213> ORGANISM: Artificial Sequence
<220> FEATURE:
<223> OTHER INFORMATION: CHAST (L299) human forward primer

<400> SEQUENCE: 37
ggttgcgaga gacaatcccc                                                  20
```

```
<210> SEQ ID NO 38
<211> LENGTH: 19
<212> TYPE: DNA
<213> ORGANISM: Artificial Sequence
<220> FEATURE:
<223> OTHER INFORMATION: CHAST (L299) human reverse primer

<400> SEQUENCE: 38
gcagcctctt tctccctgg                                                   19

<210> SEQ ID NO 39
<211> LENGTH: 20
<212> TYPE: DNA
<213> ORGANISM: Artificial Sequence
<220> FEATURE:
<223> OTHER INFORMATION: Gm11641 mouse forward primer

<400> SEQUENCE: 39
ccactgaccc tcatccttgt                                                  20

<210> SEQ ID NO 40
<211> LENGTH: 21
<212> TYPE: DNA
<213> ORGANISM: Artificial Sequence
<220> FEATURE:
<223> OTHER INFORMATION: Gm11641 mouse reverse primer

<400> SEQUENCE: 40
cccagaaagt gcctcctttg t                                                21

<210> SEQ ID NO 41
<211> LENGTH: 22
<212> TYPE: DNA
<213> ORGANISM: Artificial Sequence
<220> FEATURE:
<223> OTHER INFORMATION: Gm17499 mouse forward primer

<400> SEQUENCE: 41
actctgtaga ccagggctgt ta                                               22

<210> SEQ ID NO 42
<211> LENGTH: 20
<212> TYPE: DNA
<213> ORGANISM: Artificial Sequence
<220> FEATURE:
<223> OTHER INFORMATION: Gm17499 mouse reverse primer

<400> SEQUENCE: 42
caccaggctg atcttggatt                                                  20

<210> SEQ ID NO 43
<211> LENGTH: 19
<212> TYPE: DNA
<213> ORGANISM: Artificial Sequence
<220> FEATURE:
<223> OTHER INFORMATION: Gm16192 mouse forward primer

<400> SEQUENCE: 43
ccatcggaaa gatttggtg                                                   19

<210> SEQ ID NO 44
<211> LENGTH: 20
<212> TYPE: DNA
<213> ORGANISM: Artificial Sequence
<220> FEATURE:
<223> OTHER INFORMATION: Gm16192 mouse reverse primer
```

<400> SEQUENCE: 44
ggaggtcgga gatatgctga                                              20

<210> SEQ ID NO 45
<211> LENGTH: 20
<212> TYPE: DNA
<213> ORGANISM: Artificial Sequence
<220> FEATURE:
<223> OTHER INFORMATION: Gm8459 mouse forward primer

<400> SEQUENCE: 45
cctcgaagtc ctgagtgacc                                              20

<210> SEQ ID NO 46
<211> LENGTH: 20
<212> TYPE: DNA
<213> ORGANISM: Artificial Sequence
<220> FEATURE:
<223> OTHER INFORMATION: Gm8459 mouse reverse primer

<400> SEQUENCE: 46
ccaatcaggc tggagttgtt                                              20

<210> SEQ ID NO 47
<211> LENGTH: 20
<212> TYPE: DNA
<213> ORGANISM: Artificial Sequence
<220> FEATURE:
<223> OTHER INFORMATION: AK083183 mouse forward primer

<400> SEQUENCE: 47
ccagagtggc cttagactgc                                              20

<210> SEQ ID NO 48
<211> LENGTH: 20
<212> TYPE: DNA
<213> ORGANISM: Artificial Sequence
<220> FEATURE:
<223> OTHER INFORMATION: AK083183 mouse reverse primer

<400> SEQUENCE: 48
ttaaaacccc tggcttgttg                                              20

<210> SEQ ID NO 49
<211> LENGTH: 20
<212> TYPE: DNA
<213> ORGANISM: Artificial Sequence
<220> FEATURE:
<223> OTHER INFORMATION: Gm13316 mouse forward primer

<400> SEQUENCE: 49
gtgtcaaatt ccaccccaac                                              20

<210> SEQ ID NO 50
<211> LENGTH: 20
<212> TYPE: DNA
<213> ORGANISM: Artificial Sequence
<220> FEATURE:
<223> OTHER INFORMATION: Gm13316 mouse reverse primer

<400> SEQUENCE: 50
ggccaagtcc cacaacttta                                              20

<210> SEQ ID NO 51

```
<211> LENGTH: 20
<212> TYPE: DNA
<213> ORGANISM: Artificial Sequence
<220> FEATURE:
<223> OTHER INFORMATION: AK013700 mouse forward primer

<400> SEQUENCE: 51
tccgagagca ccaatctctt                                              20

<210> SEQ ID NO 52
<211> LENGTH: 20
<212> TYPE: DNA
<213> ORGANISM: Artificial Sequence
<220> FEATURE:
<223> OTHER INFORMATION: AK013700 mouse reverse primer

<400> SEQUENCE: 52
tagcgagtga gtgctggaga                                              20

<210> SEQ ID NO 53
<211> LENGTH: 20
<212> TYPE: DNA
<213> ORGANISM: Artificial Sequence
<220> FEATURE:
<223> OTHER INFORMATION: Gm15892-002 mouse forward primer

<400> SEQUENCE: 53
tccaaggctg accagttctc                                              20

<210> SEQ ID NO 54
<211> LENGTH: 20
<212> TYPE: DNA
<213> ORGANISM: Artificial Sequence
<220> FEATURE:
<223> OTHER INFORMATION: Gm15892-002 mouse reverse primer

<400> SEQUENCE: 54
actgcctgaa gaccttgggt                                              20

<210> SEQ ID NO 55
<211> LENGTH: 20
<212> TYPE: DNA
<213> ORGANISM: Artificial Sequence
<220> FEATURE:
<223> OTHER INFORMATION: BC023483 mouse forward primer

<400> SEQUENCE: 55
cagttgtggg gaggtcctaa                                              20

<210> SEQ ID NO 56
<211> LENGTH: 20
<212> TYPE: DNA
<213> ORGANISM: Artificial Sequence
<220> FEATURE:
<223> OTHER INFORMATION: BC023483 mouse reverse primer

<400> SEQUENCE: 56
tgtcccagtt ctgctgtgag                                              20

<210> SEQ ID NO 57
<211> LENGTH: 20
<212> TYPE: DNA
<213> ORGANISM: Artificial Sequence
<220> FEATURE:
<223> OTHER INFORMATION: Gm12224-001 mouse forward primer

<400> SEQUENCE: 57
```

```
aagcatcacc atgtcatcca                                               20

<210> SEQ ID NO 58
<211> LENGTH: 20
<212> TYPE: DNA
<213> ORGANISM: Artificial Sequence
<220> FEATURE:
<223> OTHER INFORMATION: Gm12224-001 mouse reverse primer

<400> SEQUENCE: 58
agccgggtac agaggaagat                                               20

<210> SEQ ID NO 59
<211> LENGTH: 20
<212> TYPE: DNA
<213> ORGANISM: Artificial Sequence
<220> FEATURE:
<223> OTHER INFORMATION: AJ409495 mouse forward primer

<400> SEQUENCE: 59
ttgggtctta gctgtcgtgt                                               20

<210> SEQ ID NO 60
<211> LENGTH: 20
<212> TYPE: DNA
<213> ORGANISM: Artificial Sequence
<220> FEATURE:
<223> OTHER INFORMATION: AJ409495 mouse reverse primer

<400> SEQUENCE: 60
tcggcgtaaa acgtgtcaac                                               20

<210> SEQ ID NO 61
<211> LENGTH: 20
<212> TYPE: DNA
<213> ORGANISM: Artificial Sequence
<220> FEATURE:
<223> OTHER INFORMATION: Gm8822-202 mouse forward primer

<400> SEQUENCE: 61
gcaaaagtgg gtgaccaagc                                               20

<210> SEQ ID NO 62
<211> LENGTH: 22
<212> TYPE: DNA
<213> ORGANISM: Artificial Sequence
<220> FEATURE:
<223> OTHER INFORMATION: Gm8822-202 mouse reverse primer

<400> SEQUENCE: 62
tgttgcatat gtgggctttt ct                                            22

<210> SEQ ID NO 63
<211> LENGTH: 293
<212> TYPE: DNA
<213> ORGANISM: Homo sapiens

<400> SEQUENCE: 63
aaggggaaac aagtgccctc agaggcgctt ggctgaggat ggagaggggc tgagcccact    60
ggcagggcag aaccaggtca tgtgccatgg ccctccactg ggcctccctc cccagtttc    120 tcttctcttc tctggcccta ccatctattg tccttggggg aagctgtggc acctagatgg   180
gcagagggtg ccaacttgta atctgaaagg ggccttcaag gacaggaaat cgcagatctg   240
```

```
aatgttgtct gtttccatcc cattttaccg caatctgatt tccctgagaa tta            293

<210> SEQ ID NO 64
<211> LENGTH: 334
<212> TYPE: DNA
<213> ORGANISM: Mus musculus

<400> SEQUENCE: 64
gaggcacttt ctggggatga gaactccagt ttgcccatcc ccctctagac aggggaaagg      60
ggaaactgcc ctcagaggca ctgtgctgaa ggtggaaaga caaccaaaga cagcagcagc     120
accagcgcaa gtgccaggcg cctcccccgg gcctgccacc cccaacctcc aaatccagtt     180 cctctcccctt tgctctgagc cctgagaacc tgcctcaaag atggccaagg agcacccacc   240
cactggctga gggcgctcaa ggccaggaaa cgaagccctg gatgttgtct ttttctgtcc     300 cattttctg caacctggtt tccctaggaa ttaa                                  334

<210> SEQ ID NO 65
<211> LENGTH: 347
<212> TYPE: DNA
<213> ORGANISM: Rattus norvegicus

<400> SEQUENCE: 65
aggaggcact ttctggggat gagaactcca gttttcccat cccccctcta gacagaaggg     60
agaaagggga aactgccctc agaggcactg tgcagaaggt ggaaagactg aaccaaagac    120
agcagcatca gcgcaagtgt cagacgcctc tcctgggcct gccaccccca acctccaaat   180
ccagttcctc ttcttttttct ctgagcctac gcccctggag aacctggctc aaagatggcc  240
aaggagtacc ccactcagtg gctgaaggtc ctcaaggtca ggaaatgaag tcctggatgt   300
tgtctttttc tgtcccattt tcctgcaacc tggtttccct aggaatt                  347
```

LNCRNAS FOR THERAPY AND DIAGNOSIS OF CARDIAC HYPERTROPHY

FIELD OF INVENTION

The present invention relates to a pharmaceutical composition comprising (i) a compound promoting the expression and/or the activity of one or more long non-coding RNAs (lncRNAs) selected from SEQ ID NOs 12, 8 to 11 and 13; and/or (ii) a compound inhibiting the expression and/or the activity of one or more lncRNAs selected from SEQ ID NOs 1 to 7, 27 and 28. The present invention also relates to a compound (i) promoting the expression and/or the activity of one or more lncRNAs selected from SEQ ID NOs 12, 8 to 11 and 13; and/or (ii) inhibiting the expression and/or the activity of one or more lncRNAs selected from SEQ ID NOs 1 to 7, 27 and 28 for use in treating or preventing cardiac hypertrophy.

BACKGROUND

Large-scale analysis of mammalian transcriptomes uncovered that transcription of genomes leads to a complex proportion of RNA molecules of which only a small fraction serves as templates for protein synthesis. Several studies indicate that these non-coding RNAs (ncRNAs) have important biological functions as their protein coding counterparts and suggest that altered expression or function of ncRNAs effects cardiovascular diseases, including cardiac hypertrophy and fibrosis, coronary artery disorders, as well as myocardial infarction.

The most reflected ncRNAs in cardiovascular research are microRNAs (miRNAs, miRs). These are endogenous, single-stranded RNAs composed of approximately 20-22 nucleotides that bind other transcripts reducing the stability and/or translation of their targets. For example, it was shown that miR-21 and miR-132 induce cardiac fibrosis or hypertrophy, respectively, and that in vivo repression of these miRNAs by specific antagomiRs (being chemically engineered oligonucleotides silencing miRNAs) rescues fibrosis or hypertrophy in cardiac disease model of pressure-overload (Thum et al. Nature. 2008 456(7224):980-4.; Ucar and Gupta et al. Nat Commun. 2012 3:1078). In another study it was found that miR-24 acts as a critical regulator of angiogenesis in ischemic heart disease (Fiedler et al. Circulation. 2011 124(6):720-30).

More recent studies indicate that similar to miRNAs, long ncRNAs (lncRNAs) may also play an important role in various biological processes. LncRNAs are mRNA-like transcripts ranging from 200 nucleotides up to 100 kilobases and are classified based on their genomic distribution relative to protein-coding genes (sense to exons and/or introns, antisense, bidirectional, or intergenic). Several lncRNA transcripts are exclusively restricted to the nucleus, while others are also found in the cytoplasm. Here they interact with proteins as well as other RNA or DNA molecules enabling lncRNAs to influence a variety of gene regulatory mechanisms including chromatin modification, genomic imprinting, nuclear compartmentalization and architecture, as well as transcriptional and post-transcriptional regulation (Schonrock et al. Circ Res. 2012 Oct. 26; 111(10):1349-62.; Caley et al. ScientificWorldJournal. 2010 10:90-102). Not surprisingly, lncRNAs are involved in human disease, such as cancer, metabolic and neuronal disorders.

However, little is known about their role in cardiovascular biology. Recent studies indicated that the two lncRNAs Braveheart (Bvht) and FOXF1 adjacent non-coding developmental regulatory RNA (Fendrr) are required for the differentiation of cardiomyocytes and the development of lateral mesoderm tissue in the heart and body wall, respectively (Klattenhoff et al. Cell. 2013 152(3):570-83.; Grote et al. Dev Cell. 2013 24(2):206-14). Both lncRNAs modulate the epigenetic profile of cells via an interaction with chromatin modifying complexes. Recent reports have also started to explore the role of lncRNAs in cardiovascular disease. Genome-wide association study (GWAS) identified single-nucleotide polymorphisms (SNPs) in loci encoding for the lncRNAs MIAT (myocardial infarction-associated transcript) or ANRIL (antisense noncoding RNA in the INK4 locus) that seem to be related to risk of myocardial infarction or coronary artery disease (Ishii et al. J Hum Genet. 2006 51(12):1087-99.; McPherson et al. Science. 2007 316(5830):1488-91). The lncRNA Kcnq1ot1 controls the expression of its antisense gene Kcnq1 that encodes for a potassium channel. Since the potassium channel activity is essential for a normal cardiac performance, an altered regulation related by lncRNAs might lead to an abnormal heart function (Korostowski et al. PLoS Genet. 2012 8(9): e1002956).

SUMMARY OF INVENTION

One of the main challenges in cardiac disease research is to identify novel and effective approaches to modulate gene networks or specific intracellular signaling pathways that may prove as effective therapeutic options themselves or have the potential to expand the efficiency of existing therapeutic strategies. It was surprisingly found that specific lncRNAs play a role in the development of cardiac hypertrophy thereby providing novel therapeutic strategies.

Thus, the present invention relates in a first aspect to a pharmaceutical composition comprising (i) a compound promoting the expression and/or the activity of one or more long non-coding RNAs (lncRNAs) selected from SEQ ID NOs 12, 8 to 11 and 13; and/or (ii) a compound inhibiting the expression and/or the activity of one or more lncRNAs selected from SEQ ID NOs 1 to 7, 27 and 28.

BRIEF DESCRIPTION OF THE DRAWINGS

FIG. 11A FC of pLV+empty PBS. FIG. 11B FC of GapmeR-control PBS.

FIG. 12A FC of GapmeR-control PBS FIG. 12B FC of pLV+empty PBS.

FIG. 13A Representation of potential homologs of the lncRNA Gm11641 (ENS-MUST00000130556) in different species applying the UCSC genome browser. FIG. 13B LncRNA Gm11641 homolog in humans. FIG. 13C Detailed sequence and structure alignment of the murine Gm11641 and its homologs in rat and humans. FIG. 13D Validation of the human transcript by gene-specific PCR (lower left; n=at least 3 independent experiments). FIG. 13E Expression of the human Gm11641 homolg of SEQ ID NO: 1 in healthy donor heart tissues (n=23) or in patients with aortic stenosis (n=21). *p<0.05. FC=fold change.

FIG. 14A GM16192 expression 6 weeks after TAC. FIG. 14B whole heart expression 6 weeks after TAC. FIG. 14C GM8459 expression 6 weeks after TAC. FIG. 14D AK083183 expression 6 weeks after TAC. FIG. 14E GM13316 Expression 6 weeks after TAC. H19 expression 4 weeks after TAC.

FIG. 15A AKO13700 expression, FIG. 15B GM15892-2 expression, FIG. 15C BC0233483 expression, FIG. 15D Gm12224-1 expression, FIG. 15E AJ409459 expression, FIG. 15F Gm16192 expression, FIG. 15G Gm8822-2 expression, and FIG. 15H H19 expression. Microarray validation of H19 repression due to cardiac hypertrophy in whole heart samples after several time points post TAC (n=4–8). *p<0.05; **p<0.01. FC=fold change. FIG. 15I Expression levels of H19 in mouse hearts 2 weeks after continuous angiotensin II (ATII) infusion. (n=4×5). *p<0.05. FC=fold change. FIG. 15J Relative H19 expression (FC off vehicle).

FIG. 16A-L: Organ expression of candidate lncRNAs. FC—fold change. FIG. 16A Gm17499, FIG. 16B Gm11641, FIG. 16C Gm8549, FIG. 16D AK083183, FIG. 16E GM13316, FIG. 16F H19, FIG. 16G AK013700, FIG. 16H Gm15892-2, FIG. 16I BC023483, FIG. 16J Gm12224-1, FIG. 16K Gm16192, FIG. 16L Gm8822-2.

FIG. 17A Gm17499, FIG. 17B Gm11641, FIG. 17C GM8549, FIG. 17D GM13316, FIG. 17E H19, FIG. 17F AK013700, FIG. 17G Gm15892-2, FIG. 17H BC023483, FIG. 17I Gm12224-1, FIG. 17J Gm16192; FIG. 17K Gm8222-2.

FIG. 18A Gm17499, FIG. 18B H19, FIG. 18C GM8822-2. β-Actin, GAPDH, Xist and Neat1 were analysed as controls.

FIG. 21A siRNA Test, FIG. 21B esiRNA Test (10, 50, 100 ng), FIG. 21C esiRNA Test (3.6 and 36 ng), FIG. 21D GampeR test (Gm17499 expression), FIG. 21E GapmeR test (MALAT1 expression).

FIG. 22A Cardiomyocyte size (si-Scr and si_Gm17499), FIG. 22B immunofluorescence (si-Scr and si_Gm17499), FIG. 22C cardiomyocyte size (pLV+empty and pLV+Gm17499), FIG. 22D (C) immunofluorescence (pLV+empty and pLV+Gm17499)

FIG. 23A ANP expression (si-Scr and si_Gm17499), FIG. 23B ANP expression (pLV+empty and pLV+Gm17499), FIG. 23C BNP expression (si-Scr and si_Gm17499), FIG. 23D BNP expression (pLV+empty and pLV+Gm17499), FIG. 23E Mcip1.4 expression (si-Scr and si_Gm17499), FIG. 23F Mcip1.4 expression (pLV+empty and pLV+Gm17499).

FIG. 24A Sham vs TAC at 4 weeks and FIG. 24B Sham vs TAC at 6 weeks.

FIG. 26A Repression of lncRNAs H19 in the cardiomyocyte cell lines HL-1 (mouse) and FIG. 26B H9C2 (rat) applying esiRNA (48 h after treatment). RLUC—esiRNA against renilla luciferase (negative control), H19—esiRNA against H19. *p<0.05. FIG. 26C Repression of H19 in HL-1 cardiomyocytes by esiRNAs compared to a non-targeting control (renilla luciferase, RLUC) FIG. 26D Overexpression of H19 applying lentiviral transduction (pLV). n=at least 3 independent experiments. p<0.01; *p<0.001. FC=fold change.

FIG. 27A Cell size of murine cardiomyocyte cell line HL-1 repressing H19 (by esiRNA) treated with the hypertrophic stimuli phenylephrine (PE) and isoproterenol (ISO) or Angiotensin II (ATII) for 48 h. RLUC—esiRNA against renilla luciferase (negative control), H19—esiRNA against H19. *p<0.05. n.s.—not significant. FIG. 27B HL-1 cardiomyocyte response upon lentiviral overexpression (pLV+) of H19. Expression levels of atrial FIG. 27C and brain FIG. 27D natriuretic peptide (ANP, BNP) as well as β-myosin heavy chain (β-MHC) FIG. 27E have been determined. n=at least 3 independent experiments. p<0.01, *p<0.001. FC=fold change.

FIG. 33A Rat H19 (nt), FIG. 33B Human H19 (nt), FIG. 33C Pig H19 (nt).

FIG. 35A relative H19 expression, FIG. 35B relative a-MHC expression, FIG. 35C relative b-expression.

FIG. 36A-C: Potential transcriptional regulators of Gm11641 expression. FIG. 36A Bioinformatic prediction of transcription factors binding sites in the Gm11641 promoter (C). This includes also the pro-hypertrophic transcription factor NFAT (nuclear factor of activated T-cells). In calcineurin transgenic mice (CnA TG), which have a constitutively activated NFAT pathway (n=4), Gm11641 expression is induced, while the NFAT inhibitor 11R-VIVIT represses the expression of Gm11641 in HL-1 cardiomyocytes (n=at least 3 independent experiments). *p<0.05; FC=fold change, Gm11641 is referred to in FIG. 36 as "Chast" (cardiac hypertrophy associated transcript) FIG. 36B expression of Chast, FIG. 36C relative Chast expression.

FIG. 38C immunofluorescence, FIG. 38D cell size.

DETAILED DESCRIPTION OF THE INVENTION

Figure 1:
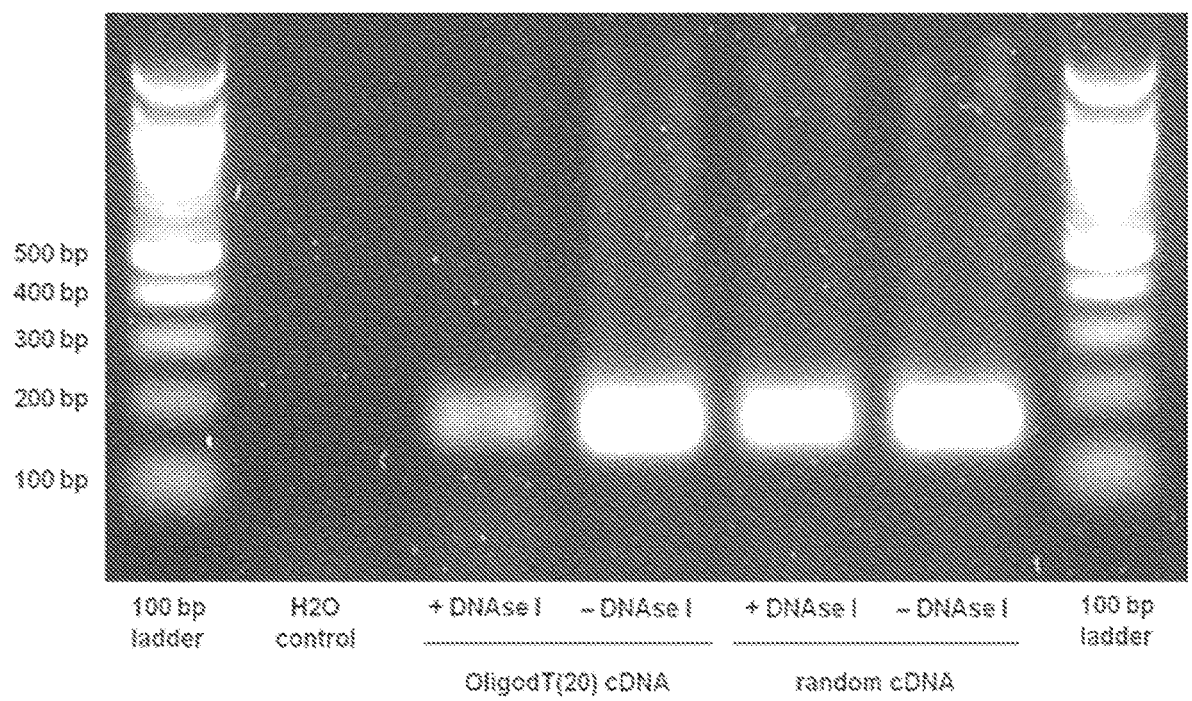
FIG. 1: Verification of lncRNA Gm11641 expression in heart samples. Mouse heart RNA was treated with DNAse I prior reverse transcription. cDNA synthesis was performed either with OligodT (20) or random primer sets.

In accordance with the present invention, the term "pharmaceutical composition" relates to a composition for administration to a patient, preferably a human patient. The pharmaceutical composition of the invention comprises the compounds recited above. It may, optionally, comprise further molecules capable of altering the characteristics of the compounds of the invention thereby, for example, stabilizing, modulating and/or activating their function. The composition may be in solid, liquid or gaseous form and may be, inter alia, in the form of (a) powder(s), (a) tablet(s), (a) solution(s) or (an) aerosol(s). The pharmaceutical composition of the present invention may, optionally and additionally, comprise a pharmaceutically acceptable carrier or excipient. Examples of suitable pharmaceutical carriers and excipients are well known in the art and include phosphate buffered saline solutions, water, emulsions, such as oil/water emulsions, various types of wetting agents, sterile solutions, organic solvents including DMSO etc. Compositions comprising such carriers or excipients can be formulated by well known conventional methods. These pharmaceutical compositions can be administered to the subject at a suitable dose. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. The therapeutically effective amount for a given situation will readily be determined by routine experimentation and is within the skills and judgement of the ordinary clinician or physician. Generally, the regimen as a regular administration of the pharmaceutical composition should be in the range of 1 μg to 5 g units per day. However, a more preferred dosage might be in the range of 0.01 mg to 100 mg, even more preferably 0.01 mg to 50 mg and most preferably 0.01 mg to 10 mg per day.

Furthermore, if for example said compound is an nucleic acid sequence, such as an siRNA, the total pharmaceutically effective amount of pharmaceutical composition administered will typically be less than about 75 mg per kg of body weight, such as for example less than about 70, 60, 50, 40, 30, 20, 10, 5, 2, 1, 0.5, 0.1, 0.05, 0.01, 0.005, 0.001, or 0.0005 mg per kg of body weight. More preferably, the amount will be less than 2000 nmol of nucleic acid sequence (e.g., about 4.4×10^16 copies) per kg of body weight, such as for example less than 1500, 750, 300, 150, 75, 15, 7.5, 1.5, 0.75, 0.15, 0.075, 0.015, 0.0075, 0.0015, 0.00075 or 0.00015 nmol of siRNA agent per kg of body weight.

The length of treatment needed to observe changes and the interval following treatment for responses to occur vary depending on the desired effect. The particular amounts may be determined by conventional tests which are well known to the person skilled in the art.

Pharmaceutical compositions of the invention preferably comprise a pharmaceutically acceptable carrier or excipient. By "pharmaceutically acceptable carrier or excipient" is meant a non-toxic solid, semisolid or liquid filler, diluent, encapsulating material or formulation auxiliary of any type (see also Handbook of Pharmaceutical Excipients 6 ed. 2010, Published by the Pharmaceutical Press). The pharmaceutical composition may be administered, for example, orally, parenterally, such as subcutaneously, intravenously, intramuscularly, intraperitoneally, intrathecally, transdermally, transmucosally, subdurally, locally or topically via iontophoresis, sublingually, by inhalation spray, aerosol or rectally and the like in dosage unit formulations optionally comprising conventional pharmaceutically acceptable carriers or excipients.

The term "ncRNA" or "non-coding RNA" as used herein designates a functional RNA molecule that is not translated into a protein. The DNA sequence from which a non-coding RNA is transcribed is often called in the art an RNA gene. The term "lncRNA" or "long non-coding RNA" is commonly used in the art and designates an ncRNA comprising more than 200 nucleotides. SEQ ID NOs 12, 1 to 11, 13, 27 and 28 comprise sequences ranging from 132 to 1598 nucleotides.

The compounds of the invention may be formulated as vesicles, such as liposomes. Liposomes have attracted great interest because of their specificity and the duration of action they offer from the standpoint of drug delivery. Liposomal delivery systems have been used to effectively deliver nucleic acids, such as siRNA in vivo into cells (Zimmermann et al. (2006) Nature, 441:111-114). Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are phagocytosed by macrophages and other cells in vivoA compound inhibiting the expression of one or more lncRNAs selected from SEQ ID NOs 1 to 7, 27 and 28—as defined herein in item (ii)—is in accordance with the present invention a compound lowering or preventing the transcription of one or more of the genes encoding the lncRNAs selected of SEQ ID NOs 1 to 7, 27 and 28. Such compounds include compounds interfering with the transcriptional machinery and/or its interaction with the promoter of said genes and/or with expression control elements remote from the promoter such as enhancers. The compound inhibiting the expression of an lncRNA selected from SEQ ID NOs 1 to 7, 27 and 28 specifically inhibits the expression of said lncRNA, for example, by specifically interfering with the promoter region controlling the expression of the lncRNA. Preferably, the transcription of an lncRNAs selected from SEQ ID NOs 1 to 7, 27 and 28 is reduced by at least 50%, more preferred at least 75% such as at least 90% or 95%, even more preferred at least 98% and most preferred by about 100%. A compound inhibiting the activity of an lncRNAs selected from SEQ ID NOs 1 to 7, 27 and 28—as defined herein in item (ii)—in accordance with the present invention causes said lncRNA to perform its function with lowered efficiency. The compound inhibiting the activity of an lncRNA selected from SEQ ID NOs 1 to 7, 27 and 28 specifically inhibits the activity of said lncRNA. Preferably, the activity of an lncRNA selected from SEQ ID NOs 1 to 7, 27 and 28 is reduced by at least 50%, more preferred at least 75% such as at least 90% or 95%, even more preferred at least 98%, and most preferably about 100%. Means and methods for determining the reduction of activity of an RNA are established in the art and are described, for example, in Esau et al. (2004), JBC, 279:52361-52365 or Gribbings et al. (2009), Nature Cell Biology 11, 1143-1149. Compounds as defined herein in item (ii) may be an antisense molecule, siRNA, shRNA, antibody, ribozyme, aptamer, or small molecule. These and other compounds will be further detailed herein below.

The efficiency of an inhibiting compound can be quantified by methods comparing the level of activity in the presence of the inhibitor to that in the absence of the inhibitor. For example, as an activity measure may be used: the change in amount of lncRNA formed. Such method may be effected in high-throughput format in order to test the efficiency of several inhibiting compound simultaneously. High-throughput assays, independently of being biochemical, cellular or other assays, generally may be performed in wells of microtiter plates, wherein each plate may contain 96, 384 or 1536 wells. Handling of the plates, including incubation at temperatures other than ambient temperature, and bringing into contact of test compounds with the assay mixture is preferably affected by one or more computer-controlled robotic systems including pipetting devices. In case large libraries of test compounds are to be screened and/or screening is to be effected within short time, mixtures of, for example 10, 20, 30, 40, 50 or 100 test compounds may be added to each well. In case a well exhibits the expected activity, said mixture of test compounds may be de-convoluted to identify the one or more test compounds in said mixture giving rise to said activity.

A compound promoting the expression of one or more lncRNAs selected from SEQ ID NOs 12, 8 to 11 and 13—as defined herein in item (i)—may be any compound enhancing or upregulating the transcription of an lncRNA selected from SEQ ID NOs 12, 8 to 11 and 13. Non-limiting examples of such compounds are transcription factors enhancing the transcription of the genes encoding the lncRNAs selected from SEQ ID NOs 12, 8 to 11 and 13 or a small molecule enhancing the expression of one or more lncRNAs selected from SEQ ID NOs 12, 8 to 11 and 13. A transcription factor is a protein binding to specific DNA sequences, thereby controlling the transcription of genetic information from DNA to RNA. A small molecule is a low molecular weight compound which is by definition not a polymer. A compound promoting the activity of one or more lncRNAs selected from SEQ ID NOs 12, 8 to 11 and 13—as defined herein in item (i)—may be any compound which causes that said lncRNA effectively performs its function in a cell. Hence, in the simplest form such a compound may be a recombinantly produced or isolated lncRNAs selected from SEQ ID NOs 12, 8 to 11 and 13 or any precursor or fragment thereof. In this embodiment the administration of a recombinantly produced or isolated lncRNA increases the concentration of lncRNA in the subject to be treated. This higher concentration promotes the overall activity of the respective lncRNA in the subject. The fragments have to retain or essentially retain the function of the full-length lncRNA. Such a compound may also be a vector or host being capable of producing such an lncRNAs. Hence, the fragments have to be functional fragments. Also orthologous or homologous sequences of the lncRNA selected from SEQ ID NOs 12, 8 to 11 and 13 from different species including precursors or functional fragments thereof may be used. In this regard, preferred homologous sequences of the human lncRNA of SEQ ID NOs 12, 8 to 11 and 13 are the respective mouse homologs of SEQ ID NO: 25, 21 to 24 and 26, respectively. The most preferred homologous sequence is SEQ NO: 12. Alternatively, such a compound may be a compound maintaining or even enhancing the activity of an lncRNA selected from SEQ ID NOs 12, 8 to 11 and 13 by either directly or indirectly interacting with the lncRNA. For instance, such a compound may prevent an lncRNA selected from SEQ ID NOs 12, 8 to 11 and 13 from degeneration by RNases or may be an interaction partner, such as another lncRNA, which binds to and promotes the activity of an lncRNA selected from SEQ ID NOs 12, 8 to 11 and 13. Compounds as defined herein in item (i) will be further detailed herein below.

The efficiency of a compound as defined herein in item (i) can also be quantified by methods comparing the level of expression and/or activity of an lncRNA selected from SEQ ID NOs 12, 8 to 11 and 13 in the presence of a expression and/or activity promoting compound of the lncRNA, such as a transcription factor, to that in the absence of said compound. For example, as an activity measure the change in amount of lncRNA formed may be used. The method is preferably effected in high-throughput format as further detailed herein above.

The present invention relates in a second aspect to a compound (i) promoting the expression and/or the activity of one or more lncRNAs selected from SEQ ID NOs 12, 8 to 11 and 13; and/or (ii) inhibiting the expression and/or the activity of one or more lncRNAs selected from SEQ ID NOs 1 to 7, 27 and 28 for use in treating or preventing cardiac hypertrophy.

Compounds as defined herein in items (i) and (ii) have been detailed herein above in connection with the first aspect of the invention. The same compounds can be used in connection with the second aspect of the invention.

Cardiac hypertrophy is defined as an increase in size of the heart without any increase in myocyte number. This results in a thickening of the heart walls. Pathological cardiac hypertrophy occurs in response to haemodynamic overload due to different forms of stress, such as hypertension, valve disease, and myocardial infarction (MI). Prolonged hypertrophic growth of the heart results in cardiac arrhythmias, heart failure and may lead to sudden death (Frey N, Olson EN. Cardiac hypertrophy: the good, the bad, and the ugly. *Annu Rev Physiol.* 2003; 65: 45-79). Thus, cardiac hypertrophy is in accordance with the invention unhealthy cardiac hypertrophy (or pathological hypertrophy), such as cardiac hypertrophy in response to stress or disease, e.g., hypertension, heart muscle injury (myocardial infarction), heart failure or neurohormones. Unhealthy cardiac hypertrophy is to be held distinct from healthy cardiac hypertrophy (physiologic hypertrophy or "athlete's heart") which is a normal response of the heart, for example, in response to healthy exercise or pregnancy. Among healthy subjects, rowers or cyclists tend to have the largest hearts, with an average left ventricular wall thickness of 1.3 centimeters, compared to 1.1 centimeters in average adults.

In order to identify lncRNAs playing a role in the development of cardiac hypertrophy the transverse aortic constriction (TAC) mouse model was used (see deAlmeida et al. (2010), J Vis Exp. 2010 April, (38)). The TAC mouse model was established in 1991. Since then the model has been extensively used as a valuable tool to mimic human cardiac hypertrophy and to elucidate fundamental signaling processes involved in the cardiac hypertrophic response. The isolated RNA from TAC mice was used for global lncRNA profiling in whole heart as well as cardiomyocyte-specific samples applying the platforms NCode and Arraystar. It was surprisingly found that specific lncRNAs are significantly deregulation in TAC mice as compared to negative control mice. These lncRNAs were selected from the profiling data (see Table 5). The presence of transcripts in mouse heart tissue was verified by PCR and the deregulation was validated by real-time PCR.

As it is evident from the examples herein below, the present invention unexpectedly found that the mouse homologs (i.e. the lncRNAs of SEQ ID NOs 14 to 20) of the human lncRNAs of SEQ ID NOs 1 to 7, 27 and 28 are significantly upregulated in the TAC mouse model as compared to negative control mice. In this respect it is of note that the human sequences SEQ ID NOs 1, 27 and 28 are all homologs of the mouse sequence of SEQ ID NO: 14. Due to a genomic duplication event distinguishing human and mouse more than one human homolog exists. All three human homolgs were found to be expressed in human heart tissues, and most strikingly were found to be upregulated in hypertrophic hearts from patients with aortic stenosis (see FIG. 13B). The upregulation of these mouse and human homologous lncRNAs is evidently associated with the development of cardiac hypertrophy. Consequently, the mouse lncRNAs of SEQ ID NOs 14 to 20 as well as the homologous human lncRNAs of SEQ ID NOs 1 to 7, 27 and 28 are pro-hypertrophic lncRNAs. It can be expected that the homologous human lncRNAs have the same function as the mouse lncRNAs. It follows that the inhibition of the expression and/or activity of the lncRNAs of SEQ ID NOs 1 to 7, 27 and 28 in humans will be beneficial for the treatment or prevention of cardiac hypertrophy.

As it is furthermore evident from the examples herein below, the present invention reveals that the mouse homologs (i.e. the lncRNAs of SEQ ID NOs 25, 21 to 24 and 26) of the human lncRNAs of SEQ ID NOs 12, 8 to 11 and 13 are significantly downregulated in the TAC mouse model as compared to negative control mice. The downregulation of these mouse lncRNAs is evidently associated with the development of cardiac hypertrophy. Consequently, the mouse lncRNAs of SEQ ID NOs 25, 21 to 24 and 26 as well as the homologous human lncRNAs of SEQ ID NOs 12, 8 to 11 and 13 are anti-hypertrophic lncRNAs. It follows that the promotion of the expression and/or activity of the lncRNAs of SEQ ID NOs 12, 8 to 11 and 13 in humans will be beneficial for the treatment or prevention of cardiac hypertrophy.

Figure 11A:
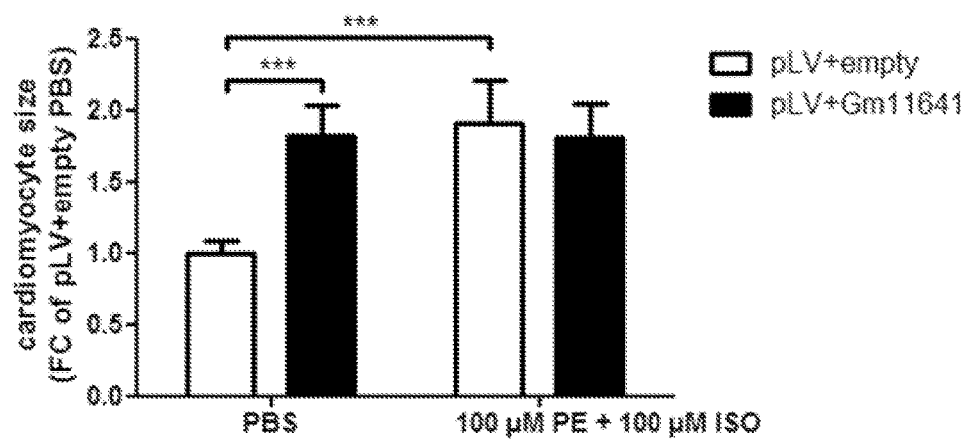
FIG. 11A-B: Lentivirus-mediated overexpression and GapmeR-based silencing and of lncRNA Gm11641 in HL-1 cells stimulated with phenlyephrine (PE) and isoproterenol (ISO). ***p<0.001, *p<0.05.
Figure 11B:
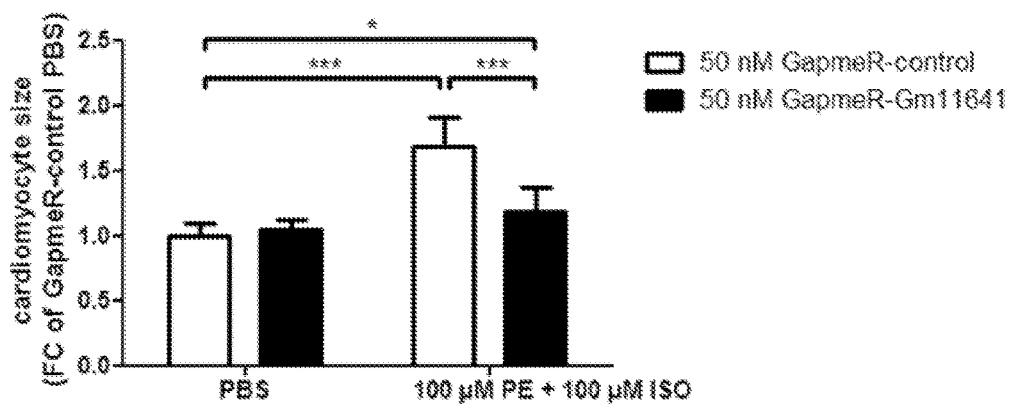

The conclusion that the mouse lncRNAs of SEQ ID NOs 14 to 20 are pro-hypertrophic lncRNAs while the mouse lncRNAs of SEQ ID NOs 25, 21 to 24 and 26 are anti-hypertrophic lncRNAs has been further experimentally proven for the pro-hypertrophic RNA lncRNA Gm11641 (SEQ ID NO: 14; human homologs SEQ ID NOs 1, 27 and 28), anti-hypertrophic lncRNA Gm17499 (SEQ ID NO: 21, human homolog SEQ ID NO: 8) and anti-hypertrophic lncRNA H19 (SEQ ID NO: 25; human homolog SEQ ID NO:12) by an independent in vitro model. Gm11641 is also referred to herein as Chast (cardiac hypertrophy associated transcript). The hallmark of hypertrophied cardiomyocytes is an increase in cell size, relative to non-hypertrophic cells. In vitro hypertrophic growth and increase in cell size of HL-1 mouse cardiac muscle cells can be induced by phenylephrine (PE) and isoproterenol (ISO). Therefore, in a first experimental setup the cell size of HL-1 mouse cardiac muscle cells after stimulation with PE and ISO was investigated under conditions, wherein (a) the expression of lncRNA Gm11641 is repressed as well as (b) under conditions, wherein the expression of lncRNA Gm11641 is elevated (see FIG. 11). In line with the results in the TAC mouse model, it was found that the overexpression of lncRNA Gm11641 leads to an increase of cell size as compared to a negative control, while repression of lncRNA Gm11641 reduced cardiomyocyte size and further attenuated the PE/ISO-induced increase of cell size. Moreover, Gm11641 overexpression increases the muscle mass of the left ventricle and induces cardiomyocyte growth (FIG. 38). These results show the pro-hypertrophic function of lncRNA Gm11641. Corresponding experiments were performed in a second and a third experimental setup with the lncRNAs Gm17499 and H19, respectively. Also in line with the results in the TAC mouse model, enhanced expression of the lncRNA Gm17499 prevents HL-1 cell size increase due to pro-hypertrophic stimuli, while silencing of the lncRNA Gm17499 results in an enlargement of HL-1 cardiomyocytes, indicating an anti-hypertrophic function of this transcript (see FIG. 22). These results show the anti-hypertrophic function of the lncRNA Gm17499. Similar results were observed in experiments with the suppression of the lncRNA H19 (see FIG. 28 to 30). Importantly, when expression of H19 was examined in human healthy and hypertrophic heart (due to aortic stenosis) tissue, it was found that H19 is strongly downregulated in hypertrophied hearts (see FIG. 31). In addition, in vivo results on H19 knock-down mice indicate that H19 has a beneficial effect on the hypertrophic gene program and is useful in an anti-hypertrophic therapy (see FIGS. 34 and 35).

In accordance with a preferred embodiment of the second aspect of the invention the cardiac hypertrophy is a ventricular hypertrophy.

Most cases of cardiac hypertrophy affect the heart ventricles. Although left ventricular hypertrophy is more common, cardiac hypertrophy can also occur in the right ventricle or both ventricles. The ventricles are the chambers in the heart responsible for pumping blood either to the lungs (right ventricle) or to the rest of the body (left ventricle).

In accordance with a preferred embodiment of the first and second aspect of the invention the compound as defined in (ii) is (a) a nucleic acid sequence which comprises or consists of a nucleotide sequence being complementary to at least 12 continuous nucleotides of a lncRNAs selected from SEQ ID NOs 1 to 7, 27 and 28, (b) a nucleic acid sequence which comprises or consists of a nucleotide sequence which is at least 69% identical to the complementary strand of one or more lncRNAs selected from SEQ ID NOs 1 to 7, 27 and 28, (c) a nucleic acid sequence which comprises or consists of a nucleotide sequence according to (a) or (b), wherein U is replaced by T, (d) an expression vector expressing the nucleic acid sequence as defined in any one of (a) to (c), preferably under the control of a heart-specific promoter, or (e) a host comprising the expression vector of (d).

The term "nucleic acid sequence" or "nucleotide sequence", in accordance with the present invention, includes DNA, such as cDNA or, in a preferred embodiment genomic DNA, and RNA. It is understood that the term "RNA" as used herein comprises all forms of RNA including, in a preferred embodiment, mRNA or miRNA. The term "nucleic acid sequence" is interchangeably used in accordance with the invention with the term "polynucleotide".

The nucleic acid sequences as defined in items (a) to (c) of this preferred embodiment comprise or consist of sequences that comprise or are complementary to nucleotides of an lncRNA selected from SEQ ID NOs 1 to 7, 27 and 28. Hence, these nucleic acid sequences comprise or are antisense nucleic acid sequences. The antisense technology for silencing the expression of a target gene is well-established and widely used in the art to treat various diseases.

The molecule according to item (a) of this preferred embodiment of the invention comprises or consists of a sequence which is with increasing preference complementary to at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides, at least 22 nucleotides, or all 23 nucleotides of SEQ ID NOs 1 to 7, 27 and 28. These at least 13 nucleotides, at least 14 nucleotides, at least 15 nucleotides, at least 16 nucleotides, at least 17 nucleotides, at least 18 nucleotides, at least 19 nucleotides, at least 20 nucleotides, or at least 21 nucleotides are preferably a contiguous part of SEQ ID NOs 1 to 7, 27 and 28, i.e. the nucleotides are consecutive in the respective SEQ ID NO.

The molecule according to item (a) is preferably a "siRNA". The term "siRNA" in accordance with the present invention refers to small interfering RNA, also known as short interfering RNA or silencing RNA. siRNAs are a class of 18 to 30, preferably 20 to 25, most preferred 21 to 23 or 21 nucleotide-long double-stranded RNA molecules that play a variety of roles in biology. Most notably, siRNA is involved in the RNA interference (RNAi) pathway where the siRNA interferes with the expression of a specific gene. In addition to their role in the RNAi pathway, siRNAs also act in RNAi-related pathways, e.g. as an antiviral mechanism or in shaping the chromatin structure of a genome. siRNAs have a well defined structure: a short double-strand of RNA (dsRNA), advantageously with at least one RNA strand having an overhang. Each strand typically has a 5' phosphate group and a 3' hydroxyl (—OH) group. This structure is the result of processing by dicer, an enzyme that converts either long dsRNAs or small hairpin RNAs into siRNAs. siRNAs can also be exogenously (artificially) introduced into cells to bring about the specific knockdown of a gene of interest. Thus, any gene of which the sequence is known can in principle be targeted based on sequence complementarity with an appropriately tailored siRNA. The double-stranded RNA molecule or a metabolic processing product thereof is capable of mediating target-specific nucleic acid modifications, particularly RNA interference and/or DNA methylation. Also preferably at least one RNA strand has a 5'- and/or 3'-overhang. Preferably, one or both ends of the double-strand have a 3'-overhang from 1-5 nucleotides, more preferably from 1-3 nucleotides and most preferably 2 nucleotides. In general, any RNA molecule suitable to act as siRNA is envisioned in the present invention. The most efficient silencing was so far obtained with siRNA duplexes composed of 21-nt sense and 21-nt antisense strands, paired in a manner to have 2-nt 3'- overhangs. The sequence of the 2-nt 3' overhang makes a small contribution to the specificity of target recognition restricted to the unpaired nucleotide adjacent to the first base pair (Elbashir et al. Nature. 2001 May 24; 411(6836):494-8). 2'-deoxynucleotides in the 3' overhangs are as efficient as ribonucleotides, but are often cheaper to synthesize and probably more nuclease resistant. The siRNA according to the invention comprises an antisense strand which comprises or consists of a sequence which is with increasing preference complementary to at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides, at least 22 nucleotides, or all 23 nucleotides of SEQ ID NOs 1 to 7, 27 and 28. These at least 13 nucleotides, at least 14 nucleotides, at least 15 nucleotides, at least 16 nucleotides, at least 17 nucleotides, at least 18 nucleotides, at least 19 nucleotides, at least 20 nucleotides, or at least 21 nucleotides are preferably a contiguous part of SEQ ID NOs 1 to 7, 27 and 28, i.e. the nucleotides are consecutive in the respective SEQ ID NO.

The molecule according to item (a) is also preferably a "shRNA". A "shRNA" in accordance with the present invention is a short hairpin RNA, which is a sequence of RNA that makes a (tight) hairpin turn that can also be used to silence gene expression via RNA interference. shRNA preferably utilizes the U6 promoter for its expression. The shRNA hairpin structure is cleaved by the cellular machinery into siRNA, which is then bound to the RNA-induced silencing complex (RISC). This complex binds to and cleaves mRNAs which match the shRNA that is bound to it. The shRNA according to the invention comprises or consists a sequence which is with increasing preference complementary to at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides, at least 22 nucleotides, or all 23 nucleotides of SEQ ID NOs 1 to 7, 27 and 28. These at least 13 nucleotides, at least 14 nucleotides, at least 15 nucleotides, at least 16 nucleotides, at least 17 nucleotides, at least 18 nucleotides, at least 19 nucleotides, at least 20 nucleotides, or at least 21 nucleotides are preferably a contiguous part of SEQ ID NOs 1 to 7, 27 and 28, i.e. the nucleotides are consecutive in the respective SEQ ID NO.

A molecule according to item (b) of the above preferred embodiment of the invention is capable of interacting with, more specifically hybridizing with the target lncRNA. By formation of the hybrid the function of the lncRNA is reduced or blocked. Standard methods relating to such antisense technology have been described (see, e.g., Melani et al., Cancer Res. (1991) 51:2897-2901). The term "antisense molecule" in accordance with the present invention thus relates to a nucleic acid molecule, preferably an RNA molecule that has a base sequence complementary to a given lncRNA, i.e. the "sense" sequence.

A particularly preferred example of the molecule according to item (b) is an Endoribonuclease-prepared siRNA (esiRNA). An esiRNA is a mixture of siRNA oligos resulting from cleavage of a long double-stranded RNA (dsRNA) according to item (b) with an endoribonuclease such as *Escherichia coli* RNase III or dicer. esiRNAs are an alternative concept to the usage of chemically synthesized siRNA for RNA Interference (RNAi). An esiRNAs is the enzymatic digestion of a long double stranded RNA in vitro. For the generation of esiRNAs a cDNA of an lncRNA template may be amplified by PCR and tagged with two bacteriophage-promotor sequences. RNA polymerase is then used to generate long double stranded RNA that is complentary to the target-gene cDNA. This complentary RNA may be subsequently digested with RNase III from *Escherichia coli* to generate short overlapping fragments of siRNAs with a length between 18-25 base pairs. This complex mixture of short double stranded RNAs is similar to the mixture generated by Dicer cleavage in vivo and is therefore called endoribonuclease-prepared siRNA or short esiRNA. Hence, esiRNA are a heterogeneous mixture of siRNAs that all target the same mRNA sequence. esiRNAs lead to highly specific and effective gene silencing.

The sequence identity of the molecule according to item (b) to an lncRNA selected from SEQ ID NOs 1 to 7, 27 and 28 is with increasing preference least 70%, at least 75%, at least 80%, at least 85%, at least 90%, at least 95%, at least 98%, at least 99% and 100%. Means and methods for determining sequence identity are known in the art. Preferably, the BLAST (Basic Local Alignment Search Tool) program is used for determining the sequence identity with regard to one or more lncRNAs selected from SEQ ID NOs 1 to 7, 27 and 28. Preferred examples of nucleic acid sequences which comprise a nucleotide sequence which is at least 69% identical to the complementary strand of one or more lncRNAs selected from SEQ ID NOs 1 to 7, 27 and 28 are the complementary strand of one or more lncRNAs selected from SEQ ID NOs 14 to 20.

Antisense molecules, siRNAs and shRNAs of the present invention are preferably chemically synthesized using appropriately protected ribonucleoside phosphoramidites and a conventional RNA synthesizer. Suppliers of RNA synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK).

The ability of antisense molecules, siRNA, and shRNA to potently, but reversibly, silence lncRNA and genes in vivo makes these molecules particularly well suited for use in the pharmaceutical composition of the invention. Ways of administering siRNA to humans are described in De Fougerolles et al., Current Opinion in Pharmacology, 2008, 8:280-285. Such ways are also suitable for administering other small RNA molecules like shRNA. Accordingly, such pharmaceutical compositions may be administered directly formulated as a saline, via liposome based and polymer-based nanoparticle approaches, as conjugated or complexation pharmaceutical compositions, or via viral delivery systems. Direct administration comprises injection into tissue, intranasal and intratracheal administration. Liposome based and polymer-based nanoparticle approaches comprise the cationic lipid Genzyme Lipid (GL) 67, cationic liposomes, chitosan nanoparticles and cationic cell penetrating peptides (CPPs). Conjugated or complexation pharmaceutical compositions comprise PEI-complexed antisense molecules, siRNA, shRNA or miRNA. Further, viral delivery systems comprise influenza virus envelopes and virosomes.

Figure 9:
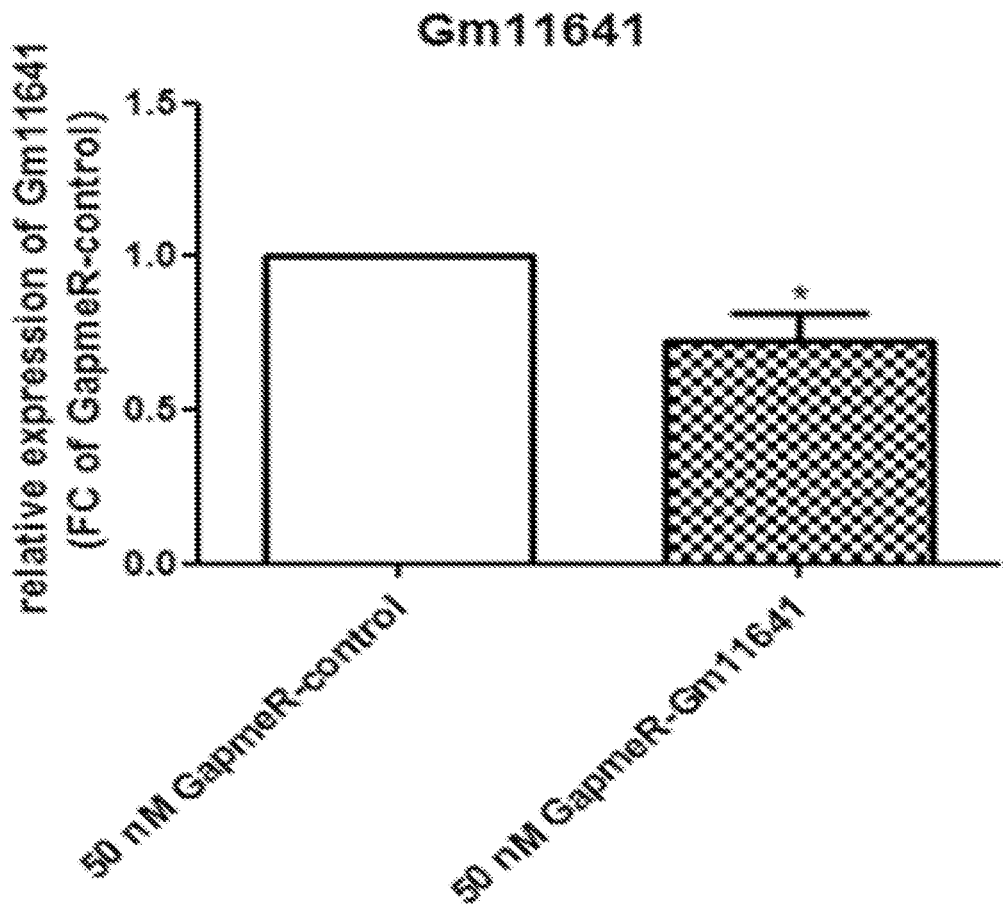
FIG. 9: Repression of lncRNA Gm11641 in HL-1 cells. Expression levels have been evaluated after 48 h of incubation time. FC—fold change. *p<0.05, p<0.01, *p<0.001, n.s.=not significant.

The antisense molecules, siRNAs, shRNAs may comprise modified nucleotides such as locked nucleic acids (LNAs). The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. Such oligomers are synthesized chemically and are commercially available. The locked ribose conformation enhances base stacking and backbone pre-organization. This significantly increases the hybridization properties (melting temperature) of oligonucleotides. Particularly preferred example of siRNAs are GapmeRs (LNA™ GapmeRs (Exigon)). GapmeRs are potent antisense oligonucleotides used for highly efficient inhibition of mRNA and lncRNA function. GapmeRs contain a central stretch of DNA monomers flanked by blocks of LNAs. The GapmeRs are preferably 14-16 nucleotides in length and are optionally fully phosphorothioated. The DNA gap activates the RNAse H-mediated degradation of targeted RNAs and is also suitable to target transcripts directly in the nucleus. GapmeRs are used in the examples, e.g., to downregulate the lncRNA Gm11641 (SEQ ID NO: 14) in the cardiomyocyte cell line HL-1 (FIG. 9).

Examples of suitable expression vectors which may be used in connection with item (d) of the above-preferred embodiment will detailed herein below.

In accordance with a further preferred embodiment of the first and second aspect of the invention the compound as defined in (ii) is an aptamer, a ribozyme, an antibody, a protein drug, or a small molecule inhibitor.

The aptamer, ribozyme, antibody, protein drug, or small molecule inhibitor of this embodiment specifically bind to one or more lncRNA selected from SEQ ID NOs 1 to 7, 27 and 28, thereby inhibiting the activity of one or more lncRNA selected from SEQ ID NOs 1 to 7, 27 and 28.

The term "aptamer" in accordance with the present invention refers to DNA or RNA molecules being either in the natural D-conformation or in the L-conformation ("spiegelmer") that have been selected from random pools based on their ability to bind other molecules. Aptamers have been selected which bind nucleic acid, proteins, small organic compounds, and even entire organisms. A database of aptamers is maintained at aptamer.icmb.utexas.edu.

More specifically, aptamers can be classified as DNA or RNA aptamers or peptide aptamers. Whereas the former consist of (usually short) strands of oligonucleotides, the latter consist of a short variable peptide domain, attached at both ends to a protein scaffold. Nucleic acid aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. The molecular target envisaged by the present invention is a nucleic acid, namely an lncRNA selected from 1 to 7, 27 and 28. Hence, aptamers can be produced against the target molecule of the invention. Peptide aptamers are peptides that are designed to interfere with other protein interactions inside cells. They consist of a variable peptide loop attached at both ends to a protein scaffold. This double structural constraint greatly increases the binding affinity of the peptide aptamer to levels comparable to an antibody's (nanomolar range). The variable loop length is typically comprised of 10 to 20 amino acids, and the scaffold may be any protein which has good solubility properties. Currently, the bacterial protein Thioredoxin-A is the most used scaffold protein, the variable loop being inserted within the reducing active site, which is a -Cys-Gly-Pro-Cys- loop in the wild protein, the two cysteins lateral chains being able to form a disulfide bridge. Peptide aptamer selection can be made using different systems, but the most used is currently the yeast two-hybrid system.

Aptamers offer the utility for biotechnological and therapeutic applications as they offer molecular recognition properties that rival those of the commonly used biomolecules, in particular antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications. Non-modified aptamers are cleared rapidly from the bloodstream, with a half-life of minutes to hours, mainly due to nuclease degradation and clearance from the body by the kidneys, a result of the aptamer's inherently low molecular weight. The rapid clearance of aptamers can be an advantage in applications such as in vivo diagnostic imaging. Several modifications, such as 2'-fluorine-substituted pyrimidines, polyethylene glycol (PEG) linkage, etc. are available to scientists with which the half-life of aptamers easily can be increased to the day or even week time scale.

The term "ribozymes" refers to RNA molecules that act as enzymes in the absence of proteins. These RNA molecules act catalytic or autocatalytic and are capable of cleaving e.g. other RNAs at specific target sites but they have also been found to catalyze the aminotransferase activity of the ribosome. Selection of appropriate target sites and corresponding ribozymes can be done as described for example in Zaher and Unrau (2007), RNA 13 (7): 1017-1026.

Examples of well-characterized small self-cleaving RNAs are the hammerhead, hairpin, hepatitis delta virus, and in vitro-selected lead-dependent ribozymes. The organization of these small catalysts is in contrast to that of larger ribozymes, such as the group I intron.

The principle of catalytic self-cleavage has become well established in the last 10 years. The hammerhead ribozymes are characterized best among the RNA molecules with ribozyme activity. Since it was shown that hammerhead structures can be integrated into heterologous RNA sequences and that ribozyme activity can thereby be transferred to these molecules, it appears that catalytic sequences for almost any target sequence can be created, provided the target sequence contains a potential matching cleavage site.

The basic principle of constructing hammerhead ribozymes is as follows: An interesting region of the RNA, which contains the GUC (or CUC) triplet, is selected. Two oligonucleotide strands, each with 6 to 8 nucleotides, are taken and the catalytic hammerhead sequence is inserted between them. Molecules of this type were synthesized for numerous target sequences. They showed catalytic activity in vitro and in some cases also in vivo. The best results are usually obtained with short ribozymes and target sequences. Since the target sequence is a short RNA sequence, namely an lncRNA selected from SEQ ID NOs 1 to 7, 27 and 28. lncRNAs selected from SEQ ID NOs 1 to 7, 27 and 28 are bona fide targets sequences for the generation of ribozymes being capable to specifically cleave an lncRNA selected from SEQ ID NOS 1 to 7, 27 and 28.

Also the aptamers and ribozymes may comprise modified nucleotides, such as locked nucleic acids (LNAs).

The term "antibody" as used in accordance with the present invention comprises, for example, polyclonal or monoclonal antibodies. Furthermore, also derivatives or fragments thereof, which still retain the binding specificity, are comprised in the term "antibody". Antibody fragments or derivatives comprise, inter alia, Fab or Fab' fragments, Fd, F(ab')$_2$, Fv or scFv fragments, single domain $V_H$ or V-like domains, such as VhH or V-NAR-domains, as well as multimeric formats such as minibodies, diabodies, tribodies, tetrabodies or chemically conjugated Fab'-multimers (see, for example, Altshuler et al., 2010., Holliger and Hudson, 2005). The term "antibody" also includes embodiments such as chimeric (human constant domain, non-human variable domain), single chain and humanized (human antibody with the exception of non-human CDRs) antibodies.

Various techniques for the production of antibodies and fragments thereof are well known in the art and described, e.g. in Altshuler et al., 2010. Thus, polyclonal antibodies can be obtained from the blood of an animal following immunisation with an antigen in mixture with additives and adjuvans and monoclonal antibodies can be produced by any technique which provides antibodies produced by continuous cell line cultures. Examples for such techniques are described, e.g. Harlow and Lane (1988) and (1999) and include the hybridoma technique originally described by Köhler and Milstein, 1975, the trioma technique, the human B-cell hybridoma technique (see e.g. Kozbor, 1983; Li et al., 2006) and the EBV-hybridoma technique to produce human monoclonal antibodies (Cole et al., 1985). Furthermore, recombinant antibodies may be obtained from monoclonal antibodies or can be prepared de novo using various display methods such as phage, ribosomal, mRNA, or cell display. A suitable system for the expression of the recombinant (humanized) antibodies or fragments thereof may be selected from, for example, bacteria, yeast, insects, mammalian cell lines or transgenic animals or plants (see, e.g., U.S. Pat. No. 6,080,560; Holliger and Hudson, 2005). Further, techniques described for the production of single chain antibodies (see, inter alia, U.S. Pat. No. 4,946,778) can be adapted to produce single chain antibodies specific for the target of this invention. Surface plasmon resonance as employed in the BIAcore system can be used to increase the efficiency of phage antibodies.

The term "protein drug" designates designer drugs that are derivatives of human proteins. These proteins are used as scaffold to create a protein drug by well-established screening procedures (see Tomlinson et al (2004), NATURE BIOTECHNOLOGY, 22(5): 521-522). Non-limiting examples of human proteins which serve as a scaffold for designing protein drugs are transferrin, C-type lectins, trinectins, domain antibodies, kunitz domains, lipocalins and the Fyn SH3 domain.

A small molecule inhibitor is a low molecular weight organic compound which is by definition not a polymer. The small molecule of the invention is preferably a molecule that binds with high affinity to an lncRNA of SEQ ID NOs 1 to 7, 27 and 28 and in addition inhibits the activity of an lncRNA of SEQ ID NOs 1 to 7, 27 and 28. The upper molecular weight limit for a small molecule is preferably 1500 Da, more preferably 1000 Da and most preferably 800 Da which allows for the possibility to rapidly diffuse across cell membranes so that they can reach intracellular sites of action. Libraries of small organic molecules and high-throughput techniques for screening such libraries with a specific target molecule, in the present case an lncRNA selected from SEQ ID NOs 1 to 7, 27 and 28, are established in the art.

Antisense molecule, siRNA, shRNA, antibody, enzyme, ribozyme, aptamer, protein drug, or small molecule inhibitor may be fused to a lipid, such as a cholesterol. Means and methods to introduce lipid modifications and in particular a cholesterol modification to a nucleic acid molecule are described in Krützfeldt et al. 2005 (Nature 438, 685-689). For example, a cholesterol may be linked through a hydroxylprolinol linkage to a nucleic acid molecule. Such modifications increase the efficiency of the uptake of a nucleic acid molecule and in particular of small RNAs into the cell.

In accordance with another preferred embodiment of the first and second aspect of the invention the compound as defined in (i) is (a) a nucleic acid sequence which comprises or consists of the nucleic acid sequence of one or more lncRNAs selected from SEQ ID NOs 12, 8 to 11 and 13 or an nucleic acid sequence which is at least 69% identical thereto, (b) an expression vector expressing the nucleic acid sequence as defined in (a), preferably under the control of a heart-specific promoter, or (c) a host comprising the expression vector of (b).

The nucleic acid sequence according to item (a) of this preferred embodiment may be a recombinantly produced or isolated lncRNAs selected from SEQ ID NOs 12, 8 to 11 and 13, any precursor thereof or any fragment thereof as long as a sequence identity of at least 69% over the entire length of an lncRNA selected from SEQ ID NOs 12, and 8 to 11 and 13 is maintained. Also orthologous or homologous sequences of the lncRNA selected from SEQ ID NOs 12, 8 to 11 and 13 from different species including precursor or a functional fragment thereof may be used. Preferably the respective mouse homologs of SEQ ID NO: 21 to 26 are used. The fragments have to retain or essentially retain the function of the full-length lncRNA. Hence, the fragments have to be functional fragments. Particularly preferred examples of sequences comprising a nucleic acid sequence which is at least 69% identical to lncRNAs of SEQ ID NOs 8 to 13 are the mouse homologous lncRNAs of SEQ ID NOs 21 to 26, respectively. The most preferred mouse homologous lncRNA is SEQ ID NO: 25.

The sequence identity of the nucleic acid sequence according to item (a) to an lncRNA selected from SEQ ID NOs 12, 8 to 11 and 13 is with increasing preference at least 70%, at least 75%, at least 80%, at least 85%, at least 90%, at least 95%, at least 98%, at least 99% and 100%. Means and methods for determining sequence identity are known in the art. Preferably, the BLAST (Basic Local Alignment Search Tool) program is used for determining the sequence identity with regard to one or more lncRNAs selected from SEQ ID NOs 12, 8 to 11 and 13.

In accordance with items (b) and (c) of the above preferred embodiment such a compound may also be an expression vector or host being capable of producing an nucleic acid sequence as defined in item (a).

An expression vector may be a plasmid that is used to introduce a specific transcript into a target cell. Once the expression vector is inside the cell, the protein that is encoded by the gene is produced by the cellular-transcription and translation machinery ribosomal complexes. The plasmid is in general engineered to contain regulatory sequences that act as enhancer and/or promoter regions and lead to efficient transcription of the transcript. In accordance with the present invention the expression vector preferably contains a heart-specific promoter. Heart-specific promoters are known in the art, for example, from Boecker at al. (2004), Mol Imagin.; 3(2):69-75. This ensures that the nucleic acid sequence is only expressed in the heart and may avoid potential unwanted side effects by expression in other organs.

Non-limiting examples of expression vectors include prokaryotic plasmid vectors, such as the pUC-series, pBluescript (Stratagene), the pET-series of expression vectors (Novagen) or pCRTOPO (Invitrogen) and vectors compatible with an expression in mammalian cells like pREP (Invitrogen), pcDNA3 (Invitrogen), pCEP4 (Invitrogen), pMC1neo (Stratagene), pXT1 (Stratagene), pSG5 (Stratagene), EBO-pSV2neo, pBPV-1, pdBPVMMTneo, pRSVgpt, pRSVneo, pSV2-dhfr, pIZD35, pLXIN, pSIR (Clontech), pIRES-EGFP (Clontech), pEAK-10 (Edge Biosystems) pTriEx-Hygro (Novagen) and pCINeo (Promega). Examples for plasmid vectors suitable for Pichia pastoris comprise e.g. the plasmids pAO815, pPIC9K and pPIC3.5K (all Intvitrogen). For the formulation of a pharmaceutical composition a suitable vector is selected in accordance with good manufacturing practice. Such vectors are known in the art, for example, from Ausubel et al, Hum Gene Ther. 2011 April; 22(4):489-97 or Allay et al., Hum Gene Ther. May 2011; 22(5): 595-604.

A typical mammalian expression vector contains the promoter element, which mediates the initiation of transcription of mRNA, the protein coding sequence, and signals required for the termination of transcription and polyadenylation of the transcript. Moreover, elements such as origin of replication, drug resistance gene, regulators (as part of an inducible promoter) may also be included. The lac promoter is a typical inducible promoter, useful for prokaryotic cells, which can be induced using the lactose analogue isopropylthiol-b-D-galactoside. ("IPTG"). For recombinant expression and secretion, the polynucleotide of interest may be ligated between e.g. the PelB leader signal, which directs the recombinant protein in the periplasm and the gene III in a phagemid called pHEN4 (described in Ghahroudi et al, 1997, FEBS Letters 414:521-526). Additional elements might include enhancers, Kozak sequences and intervening sequences flanked by donor and acceptor sites for RNA splicing. Highly efficient transcription can be achieved with the early and late promoters from SV40, the long terminal repeats (LTRs) from retroviruses, e.g., RSV, HTLVI, HIVI, and the early promoter of the cytomegalovirus (CMV). However, cellular elements can also be used (e.g., the human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Alternatively, the recombinant (poly)peptide can be expressed in stable cell lines that contain the gene construct integrated into a chromosome. The co-transfection with a selectable marker such as dhfr, gpt, neomycin, hygromycin allows the identification and isolation of the transfected cells. The transfected nucleic acid can also be amplified to express large amounts of the encoded (poly)peptide. The DHFR (dihydrofolate reductase) marker is useful to develop cell lines that carry several hundred or even several thousand copies of the gene of interest. Another useful selection marker is the enzyme glutamine synthase (GS) (Murphy et al. 1991, *Biochem J.* 227:277-279; Bebbington et al. 1992, *Bio/Technology* 10:169-175). Using these markers, the mammalian cells are grown in selective medium and the cells with the highest resistance are selected. As indicated above, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. For vector modification techniques, see Sambrook and Russel (2001), Molecular Cloning: A Laboratory Manual, 3 Vol. Generally, vectors can contain one or more origins of replication (ori) and inheritance systems for cloning or expression, one or more markers for selection in the host, e.g., antibiotic resistance, and one or more expression cassettes. Suitable origins of replication (ori) include, for example, the Col E1, the SV40 viral and the M 13 origins of replication.

The coding sequences inserted in the vector can e.g. be synthesized by standard methods, or isolated from natural sources. Ligation of the coding sequences to transcriptional regulatory elements and/or to other amino acid encoding sequences can be carried out using established methods. Transcriptional regulatory elements (parts of an expression cassette) ensuring expression in prokaryotes or eukaryotic cells are well known to those skilled in the art. These elements comprise regulatory sequences ensuring the initiation of the transcription (e.g., translation initiation codon, promoters, enhancers, and/or insulators), internal ribosomal entry sites (IRES) (Owens, Proc. Natl. Acad. Sci. USA 98 (2001), 1471-1476) and optionally poly-A signals ensuring termination of transcription and stabilization of the transcript. Additional regulatory elements may include transcriptional as well as translational enhancers, and/or naturally-associated or heterologous promoter regions.

Preferably, the nucleotide sequence as defined in item (a) of the above preferred embodiment of the invention is operatively linked to such expression control sequences allowing expression in prokaryotic or eukaryotic cells.

The host may be a prokaryotic or eukaryotic cell. A suitable eukaryotic host may be a mammalian cell, an amphibian cell, a fish cell, an insect cell, a fungal cell or a plant cell. Representative examples of bacterial cells are *E. coli, Streptomyces* and *Salmonella typhimurium* cells; of fungal cells are yeast cells; and of insect cells are Drosophila S2 and Spodoptera Sf9 cells. It is preferred that the cell is a mammalian cell such as a human cell. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells. The cell may be a part of a cell line, preferably a human cell line. Appropriate culture mediums and conditions for the above-described host cells are known in the art. The host is preferably a host cell and more preferably an isolated host cell. The host is also preferably a non-human host.

In accordance with another preferred embodiment of the first and second aspect of the invention the compound as defined in (i) is (a) a transcription factor promoting the expression of one or more lncRNAs selected from SEQ ID NOs 12, 8 to 11 and 13, and/or (b) a small molecule enhancing the expression of one or more lncRNAs selected from SEQ ID NOs 12, 8 to 11 and 13.

The term "transcription factor" as used herein defines a protein or peptide that binds to specific DNA sequences, thereby controlling the transcription of the genes encoding of one or more lncRNAs selected from SEQ ID NOs 12, 8 to 11 and 13. The efficiency of a transcription factor in activating the expression of an lncRNAs selected from SEQ ID NOs 12, 8 to 11 and 13 can be quantified by methods comparing the level of the lncRNA in the presence of the transcription factor to that in the absence of the transcription factor. For example, as an activity measure the change in amount of lncRNA formed may be used. Such a method may be effected in high-throughput format in order to test the efficiency of several inhibiting compound simultaneously. High-throughput formats have been further detailed herein above.

The small molecule enhancing the expression of one or more lncRNAs selected from SEQ ID NOs 12, 8 to 11 and 13 is a low molecular weight organic compound which is by definition not a polymer. The small molecule of the invention is preferably a molecule that binds with high affinity to an lncRNA of SEQ ID NOs 12, 8 to 11 and 13 and in addition enhances the activity of an lncRNA of SEQ ID NOs 11, 8 to 11 and 13. The upper molecular weight limit for a small molecule is preferably 1500 Da, more preferably 1000 Da and most preferably 800 Da which allows for the possibility to rapidly diffuse across cell membranes so that they can reach intracellular sites of action. Libraries of small organic molecules and high-throughput techniques for screening such libraries with a specific target molecule, in the present case an lncRNA selected from SEQ ID NOs 12, 8 to 11 and 13, are established in the art.

In a third aspect the present invention relates to a method for diagnosing cardiac hypertrophy in a patient, comprising (a) detecting the expression level of one or more lncRNAs selected from SEQ ID NOs 12, 1 to 11, 13, 27 and 28 in a sample obtained from said patient, and (b) comparing said expression level of the one or more lncRNAs with the expression level of these one or more lncRNAs in a sample obtained from healthy subjects, wherein a greater than 2-fold downregulation of one or more lncRNAs selected from SEQ ID NOs 1 to 7, 27 and 28; and/or a greater than 2-fold upregulation of one or more lncRNAs selected from SEQ ID NOs 12, 8 to 11 and 13 is indicative for a cardiac hypertrophy in the patient.

The method according to the third aspect of the invention may also encompass detecting and comparing the expression level of one or more lncRNAs being with increased preference at least 90%, at least 92%, at least 94%, at least 96%, at least 98%, at least 99%, and at least 99.5% identical to any one of SEQ ID NOs 12, 1 to 11, 13, 27 and 28. Means and methods for determining sequence identity are known in the art. Preferably, the BLAST (Basic Local Alignment Search Tool) program is used for determining the sequence identity with regard to one or more lncRNAs selected from SEQ ID NOs 1 to 7, 27 and 28 and/or 12, 8 to 11 and 13. The method according to the third aspect of the invention may furthermore encompass detecting and comparing the expression level of one or more lncRNAs differing with increasing preference by no more than 10, such as 5, 4, 3, 2 or 1 nucleotide(s) from any one of SEQ ID NOs 1 to 7, 27 and 28 and/or 12, 8 to 11 and 13. The nucleotide differences may be the addition, deletion and/or substitution of nucleotide(s). The sequences the expression of which is compared, while being homologous, may also differ from each other with increasing preference by no more than 10, such as 5, 4, 3, 2 or 1 nucleotide(s).

The term "sample" designates a tissue sample or a body fluid sample. The body fluid sample is preferably selected from blood, serum, plasma, urine, salvia, amniotic fluid, cerebrospinal fluid and lymph. The tissue sample is preferably an organ sample, such as a heart, liver or kidney sample. As far as the method is applied to a body fluid sample it is to be understood that the expression level of an lncRNA corresponds to the concentration of the lncRNA, because lncRNAs are not directly expressed in the body fluid but secreted from the cells, said cells expressing the lncRNAs, into the body fluids.

The "patient" or "subject" referred to herein is human.

The term "detecting the expression level of lncRNA" means determining the amount or yield of the lncRNA. The lncRNAs are initially expressed within a cell. It was found in accordance with the present invention that the lncRNAs of SEQ ID NOs 1 to 7, 27 and 28 and/or 12, 8 to 11 and 13 can be detected in the sample of a patient, in particular a heart tissue sample. An lncRNA being "expressed in a sample" is therefore a lncRNA whose expression level can be detected in the sample by means and methods being further detailed herein below. An ncRNA is upregulated in a test sample if the amount or yield of the ncRNA is significantly greater as compared to the amount or yield of the corresponding ncRNA in a control sample. Likewise, an ncRNA is downregulated in a test sample if the amount or yield of the ncRNA is significantly less as compared to the amount or yield of the corresponding ncRNA in a control sample. In this context the term "corresponding ncRNA" means, for example, that the expression level of the lncRNA of SEQ ID NO: 1 in the test sample is compared to the expression level of the lncRNA of SEQ ID NO: 1 in the control sample, or likewise that the expression level of the lncRNA of SEQ ID NO: 2 in the test sample is compared to the expression level of the lncRNA of SEQ ID NO: 2 in the control sample. This applies mutatis mutandis for scenarios where the expression of more than one lncRNA selected from SEQ ID NOs 12, 1 to 11, 13, 27 and 28 is determined. For instance, if the expression level of all lncRNAs of SEQ ID NOs 12, 1 to 11, 13, 27 and 28 is determined in the test sample it is compared to the expression level of all lncRNAs of SEQ ID NOs 12, 1 to 11, 13, 27 and 28 in the control sample.

The expression level in the samples can be quantified by any suitable means and methods available from the art. In general relative and absolute quantification means and methods can be used. In absolute quantification no known standards or controls are needed. The expression level can be directly quantified. As well-known in the art, absolute quantification may rely on a predetermined standard curve. In relative quantification the expression level is quantified relative to a reference (such as known control expressions levels). Also in the absence of controls, one can relatively quantify the expression level when comparing e.g. fluorescence intensities.

Methods to assess RNA concentration may, for example, comprise measuring the fluorescence intensity of dyes that bind to nucleic acids and selectively fluoresce when bound. Such methods comprise a reverse transcription reaction and the production of cDNA, wherein the amount of the cDNA is determined thereby indirectly determining the amount of the RNA. The fluorescent-based method is particularly useful for cases where the RNA concentration is too low to accurately assess some with spectrophotometry and/or in cases where contaminants absorbing at 260 nm make accurate quantification by spectrophotometry difficult or impossible.

When comparing the expression level of the one or more lncRNAs between different samples reliability of the comparison is preferably improved by including an invariant endogenous control (expression of a reference gene) to correct for potential sample to sample variations. Such normalization with respect to an invariant endogenous control is routinely performed in the art. For example, means and methods for expression level normalization, e.g. in real-time RT-PCR (see, for example, Bustin, Journal of Molecular Endocrinology, (2002) 29, 23-39) or micro-array expression analysis (see, for example, Calza and Balwitan, Methods Mol Biol. 2010; 673:37-52) are well-established. Also methods for normalization of the expression levels of small RNA sequences are established (see, for example, Mestdagh et al. (2009) Genome Biol.; 10(6):R64). In case RT-PCR or a micro-array is used to determine the expression levels in accordance with the present invention, the expression levels are preferably normalized to a spiked-in RNA (see, for example, McCormick et al. (2011), Silence, 2:2). Known amounts of a spiked-in RNA are mixed with the sample during preparation. More preferably the RNA is externally spiked-in to plasma and/or serum before the RNA isolation process is carried out, in which case the samples are plasma and/or serum. The spiked-in RNA technology is well-known and commercial kits are available from a number of manufacturers. The spiked-in RNA is preferably a spiked-in *C. elegans* RNA.

As evident from the examples herein below, the deregulation of the levels of one or more mouse lncRNAs selected from 14 to 20 and 15 to 26 are indicative for cardiac hypertrophy as evidenced in the TAC mouse model. Thus, determining the expression levels of one or more of the respective human homologous lncRNAs selected from 12, 1 to 11, 13, 27 and 28 can be expected to be of prognostic value for diagnosing a cardiac hypertrophy in a patient. The lncRNAs selected from 12, 1 to 11, 13, 27 and 28 may be combined with further diagnostic markers for cardiac hypertrophy in order to enhance the confidentially of the diagnostic method. High-expression level of the lncRNAs selected from 1 to 7, 27 and 28 and low expression level of the lncRNAs selected from 12, 8 to 11 and 13 is indicative for cardiac hypertrophy.

In the examples herein below the primer sequences of SEQ ID NOs 29 to 62 were employed in order to detect the expression level of lncRNA, wherein the uneven numbers are forward primers and the even number are reverse primers. Consecutive numbers, such as SEQ ID NOs 29 and 30, SEQ ID NOs 31 and 32, SEQ ID NOs 33 and 34 etc. are a primer pair. The primer pair of SEQ ID NOs 29/30 is for the detection of the expression level of the mouse lncRNA H19 (SEQ ID NO: 25) while the primer pair of SEQ ID NOs 31/32 is for the detection of the expression level of the human lncRNA H19 (SEQ ID NO: 12). The primer pair of SEQ ID NOs 39/40 is for the detection of the expression level of the mouse lncRNA Gm11641 (SEQ ID NO: 14), while the expression levels of the three human homologous lncRNAs SEQ ID NOs 1, 27 and 28 can be detected by the primer pairs of SEQ ID NOs 33/34, SEQ ID NOs 35/36 and SEQ ID NOs 37/38, respectively.

One or more of these primer pairs are preferably used in the diagnostic method according to the third aspect of the invention. One or more of these primer pairs are likewise preferably incorporated into the kit of the invention being described herein below.

The greater than 2-fold downregulation is with increasing preference greater than 3-fold downregulation, greater than 4-fold downregulation, greater than 5-fold downregulation, greater than 6-fold downregulation, greater than 7-fold downregulation and greater than 8-fold downregulation. Likewise the greater than 2-fold upregulation is with increasing preference greater than 3-fold upregulation, greater than 4-fold upregulation, greater than 5-fold upregulation, greater than 6-fold upregulation, greater than 7-fold upregulation and greater than 8-fold upregulation. The higher thresholds for the up- and downregulation may increase the reliability of the method of the third aspect of the invention.

In accordance with a preferred embodiment of the third aspect of the invention the sample is a blood sample or blood-derived sample.

The blood-derived sample is preferably plasma or serum.

In accordance with another preferred embodiment of the third aspect of the invention the sample is a heart tissue sample.

The heart tissue sample comprises preferably muscle cells of the heart wall and most preferably muscle cells of the ventricular wall.

In accordance with a further preferred embodiment of the third aspect of the invention the detection of the expression level of the one or more lncRNAs comprises (a) quantitative PCR, preferably quantitative real time PCR, or (b) a template/RNA amplification method followed by determining the expression level of the one or more lncRNAs using a fluorescence- or luminescence-based quantification method.

In quantitative PCR (qPCR), the amount of amplified product is linked to fluorescence intensity using a fluorescent reporter molecule. The point at which the fluorescent signal is measured in order to calculate the initial template quantity can either be at the end of the reaction (endpoint semi-quantitative PCR) or while the amplification is still progressing (real-time qPCR).

In endpoint semi-quantitative PCR, fluorescence data are collected after the amplification reaction has been completed, usually after 30-40 cycles, and this final fluorescence is used to back-calculate the amount of template present prior to PCR.

The more sensitive and reproducible method of real-time qPCR measures the fluorescence at each cycle as the amplification progresses. This allows quantification of the template to be based on the fluorescence signal during the exponential phase of amplification, before limiting reagents, accumulation of inhibitors, or inactivation of the polymerase have started to have an effect on the efficiency of amplification. Fluorescence readings at these earlier cycles of the reaction will measure the amplified template quantity where the reaction is much more reproducible from sample to sample than at the endpoint.

A non-limiting example of a template/RNA amplification method followed by determining the expression level of the one or more lncRNAs using a fluorescence- or luminescence-based quantification method is a method combining transcription mediated amplification (TMA) and a hybridization protection assay (HPA). In more detail, such a method may comprise hybridizing one or more oligonucleotides ("capture oligonucleotides") that are complementary to any of SEQ ID NOs 12, 1 to 11, 13, 27 and 28. In case two or more of SEQ ID NOs 12, 1 to 11, 13, 27 and 28 are targeted, a separate capture oligonucleotides is used for each sequence selected from 12, 1 to 11, 13, 27 and 28. The hybridized target sequences are then captured onto magnetic microparticles that are separated from the sample in a magnetic field. Wash steps may be utilized to remove extraneous components. Target amplification typically occurs via TMA, which is a transcription-based nucleic acid amplification method that utilizes two enzymes, Moloney murine leukemia virus (MMLV) reverse transcriptase and T7 RNA polymerase. A unique set of primers is used for each target sequence selected from 12, 1 to 11, 13, 27 and 28. The reverse transcriptase is used to generate a DNA copy (containing a promoter sequence for T7 RNA polymerase) of the target sequence. T7 RNA polymerase produces multiple copies of RNA amplicon from the DNA copy. Detection of lncRNA expression level is achieved by HPA using single-stranded, chemiluminescent-labeled nucleic acid probes that are complementary to the one or more amplicon. Preferably, distinguishably labelled probes are used for each target amplicon. The labeled nucleic acid probes hybridize specifically to the amplicon. A "selection reagent" then differentiates between hybridized and unhybridized probes by inactivating the label on unhybridized probes. During the detection step, the chemiluminescent signal produced by the hybridized probe is measured in a luminometer and is reported as "Relative Light Units" (RLU), thereby quantifying the lncRNA expression level.

In accordance with a still further preferred embodiment of the third aspect of the invention the method comprises prior to the detection of the expression level of the long non-coding RNA a pre-amplification step of the RNA within the test patient's sample and/or the control patient's sample.

Performing a pre-amplification step is of particular advantage in case only a low amount of (test and/or control) sample is available. The pre-amplification step allows increasing the amount of RNA within the sample before proceeding to the analysis of the expression level. Means and methods for the pre-amplification of RNA are well known in the art (see, e.g., Vermeulen et al (2009) BMC Res Notes., 2:235). In case both the RNA in the test and control sample is pre-amplified preferably the same method for the pre-amplification step is used such that the relative amount of RNA of the test sample as compared to the control sample is maintained. In case only the RNA of the test or control sample is pre-amplified or the two RNA samples are pre-amplified by different methods, the expression level data may have to be normalized for pre-amplification step; see, e.g. Mestdagh et al. (2009), *Genome Biology* 2009, 10:R64.

In a fourth aspect the present invention relates to a kit for diagnosing cardiac hypertrophy in a patient, said kit comprising means for the detection of the expression level of one or more lncRNAs selected from SEQ ID NOs 12, 1 to 11, 13, 27 and 28, and instructions how to use the kit.

The instructions how to use the kit preferably inform inter alia that high-expression level of the lncRNAs selected from 1 to 7, 27 and 28 and low expression level of the lncRNAs selected from 12, 8 to 11 and 13 is indicative for cardiac hypertrophy.

The means for the detection of the expression level of one or more lncRNAs selected from SEQ ID NOs 12, 1 to 11, 13, 27 and 28 are preferably the means required for (i) a quantitative PCR, preferably quantitative real time PCR, or (ii) a template/RNA amplification method followed by determining the expression level of the one or more lncRNAs using a fluorescence- or luminescence-based quantification method. These means have been further detailed herein above in connection with the third aspect of the invention, and may be comprised in the kit. Hence, the means preferably comprise oligonucleotides, such as fluorescent hybridization probes or primers, which specifically hybridize to one or more lncRNAs selected from SEQ ID NOs 12, 1 to 11, 13, 27 and 28. Additional ingredients of the kits may be florescent or luminescent dyes, preferably coupled to said oligonucleotides. Also, additional ingredients of the kits may be enzymes, such as a reverse transcriptase and/or a polymerase.

In accordance with the kit of the invention the means for the detection of the expression level of one or more lncR-NAs selected from SEQ ID NOs 12, 1 to 11, 13, 27 and 28 preferably comprise means for the detection of the lncRNA of SEQ ID NO: 12.

The various components of the kit may be packaged in one or more containers such as one or more vials. The vials may, in addition to the components, comprise preservatives or buffers for storage.

In accordance with a preferred embodiment of the fourth aspect of the invention, the means are primer pairs used for the specific detection of the expression level of one or more lncRNAs selected from SEQ ID NOs 12, 1 to 11, 13, 27 and 28.

In accordance with a preferred embodiment of all four aspects of the invention the one or more lncRNAs are at least 3 lncRNAs, and preferably at least 5 lncRNAs.

Employing at least 3 lncRNAs, preferably at least 5 lncRNAs, more preferably at least 10 lncRNAs, even more preferably at least 20 lncRNAs and most preferably all lncRNAs of SEQ ID NOs 12, 1 to 11, 13, 27 and 28 will additionally increase the effectiveness of the pharmaceutical compositions, medical uses, methods and kits of the invention. Employing these numbers of lncRNAs may balance potential differences associated with particular compounds, probes or methods used in connection with the methods and kits of the invention. In the pharmaceutical compositions and medical uses of the invention these numbers of lncR-NAs may increase the beneficial effect for the subject to be treated.

In accordance with a preferred embodiment of all four aspects of the invention the one or more lncRNAs is or comprises the lncRNA of SEQ ID NO: 12.

SEQ ID NO: 12 is the human lncRNA H19. The homologous mouse lncRNA H19 is represented by SEQ ID NO: 25. The anti-hypertrophic nature of lncRNA H19 is demonstrated in example 3 herein below. The gene of the H19 lncRNA is found in humans and other mammals. The regulation of the H19 gene has been well described as a paradigm of genomic imprinting and further has been implicated in human genetic disorders and cancer. After birth, H19 is predominantly expressed in muscle tissue where it promotes differentiation and regeneration. The lncRNA's biological function in the heart remained unclear. To the best knowledge of the inventors a role or function of H19 in cardiac hypertrophy is unknown from the prior art and surprisingly found in connection with the present invention. H19 is evolutionary conserved across various mammalian species including mouse and human (see FIGS. 32 and 33).

In accordance with a further preferred embodiment of all four aspects of the invention the one or more lncRNAs is or comprises the lncRNA of SEQ ID NO: 1, 27 or 28, wherein SEQ ID NO: 1 is most preferred.

As discussed herein above SEQ ID NOs 1, 27 and 28 are the human homologous lncRNAs of the mouse lncRNA Gm11641 (SEQ ID NO: 14), noting that a genomic duplication event distinguishes human and mouse and gives rise to more than one homologous human lncRNA of the respective mouse lncRNA (see FIGS. 13A and B). The pro-hypertrophic nature of lncRNA Gm11641 is demonstrated in the example herein below by two independent cardiac hypertrophy test systems, being the TAC mouse model and phenylephrine (PE) and isoproterenol (ISO) treated HL-1 mouse cardiac muscle cells.

In accordance with a still further preferred embodiment of all four aspects of the invention the one or more lncRNAs is or comprises the lncRNA of SEQ ID NO: 8.

As discussed herein above SEQ ID NO: 8 is the human homologous lncRNA of the mouse lncRNA Gm17499 (SEQ ID NO: 21). The anti-hypertrophic nature of lncRNA Gm17499 is demonstrated in the example herein below by independent test systems.

EXAMPLES

The examples illustrate the invention:

Example 1—the Pro-Hypertrophic lncRNA Gm11641

1.1 lncRNA Profiling and Validation

To identify lncRNA candidates deregulated in whole heart samples 6 weeks after TAC (transverse aortic constriction) a general lncRNA profiling provided by Arraystar was performed (Arraystar Mouse LncRNA microarray V2.0). From this platform the lncRNA Gm11641 (ENS-MUST00000130556) was identified as a candidate (Tab. 1).

TABLE 1

LncRNA Gm11641 derived from the Ncode ™ Mouse Non-coding RNA Microarray comparing whole heart samples of 6 week sham and 6 week TAC mice.

| Name | Identifier | Source | Size | relationship | FC | regulation |
|---|---|---|---|---|---|---|
| Gm11641 | ENSMUST00000130556 | Ensembl | 923 bp | antisense | 3, 85 | up |

The expression of this lncRNA in heart was verified via polymerase chain reaction (PCR) in cDNA derived from heart RNA that was treated with DNAse I prior reverse transcription with OligodT (20) or random primer sets (FIG. 1). For further validation of the transcript, the resulting PCR band was excised and sequenced.

Figure 2A:
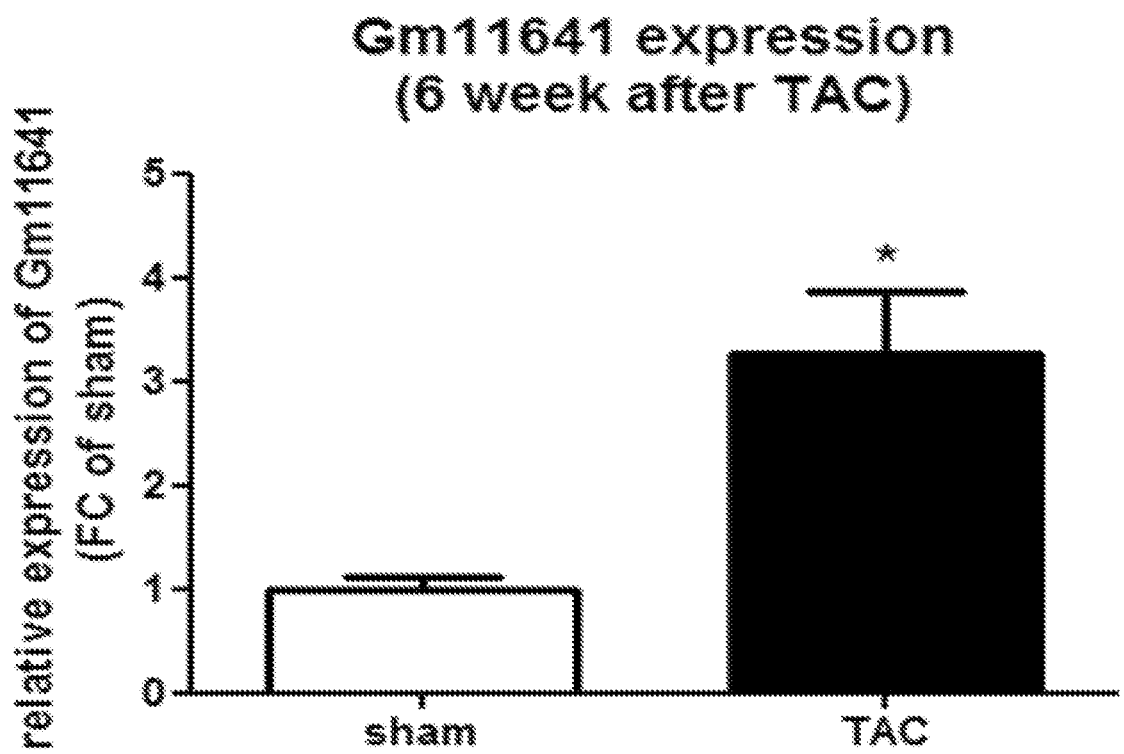
FIG. 2: (A) Validation of candidate lncRNA Gm11641 (alias Chast) in whole heart samples of sham and TAC mice 6 weeks post surgery by RT-PCR. FC—fold change. *p<0.05. n=5. (B) Validation of the transcript of Gm11641 (alias Chast) by rapid amplification of cDNA ends (RACE). This graph shows the results from 3' and 5'RACE in RNA from mouse hearts including the primer sets used for each approach.
Figure 2B:
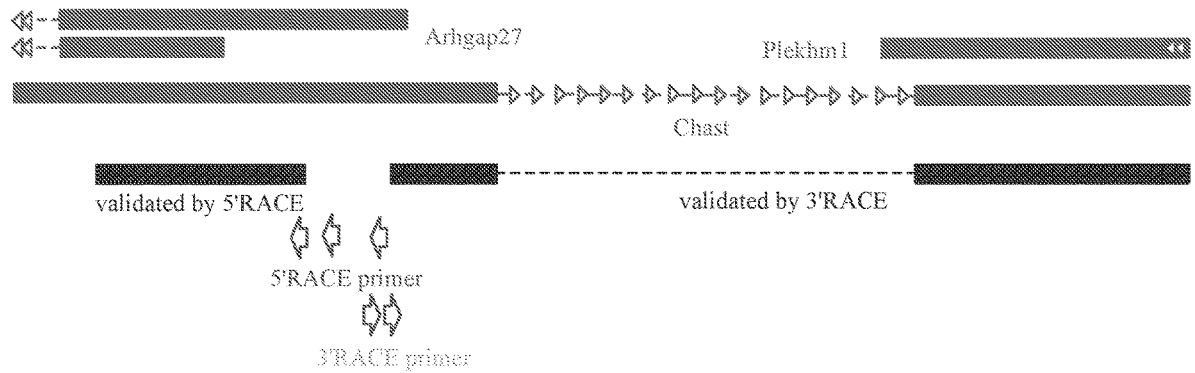

The upregulation of candidate lncRNA Gm11641 after TAC surgery was validated by real-time PCR (RT-PCR) (FIG. 2A). For further validation of the transcript, the resulting PCR band was excised and sequenced. In a second step, the transcript sequence was analysed by rapid amplification of cDNA ends (RACE) with RNA of mouse hearts as starting material. This led to a validation of both exons (FIG. 2B).

Gm11641 was overexpressed in HL-1 cells and assessed small peptides by mass spectrometry. No peptide that overlaps to a potential short open reading frames were found, showing that Gm11641 is a non-coding RNA.

1.2 Organ Expression of Candidate lncRNA Gm11641

Figure 3:
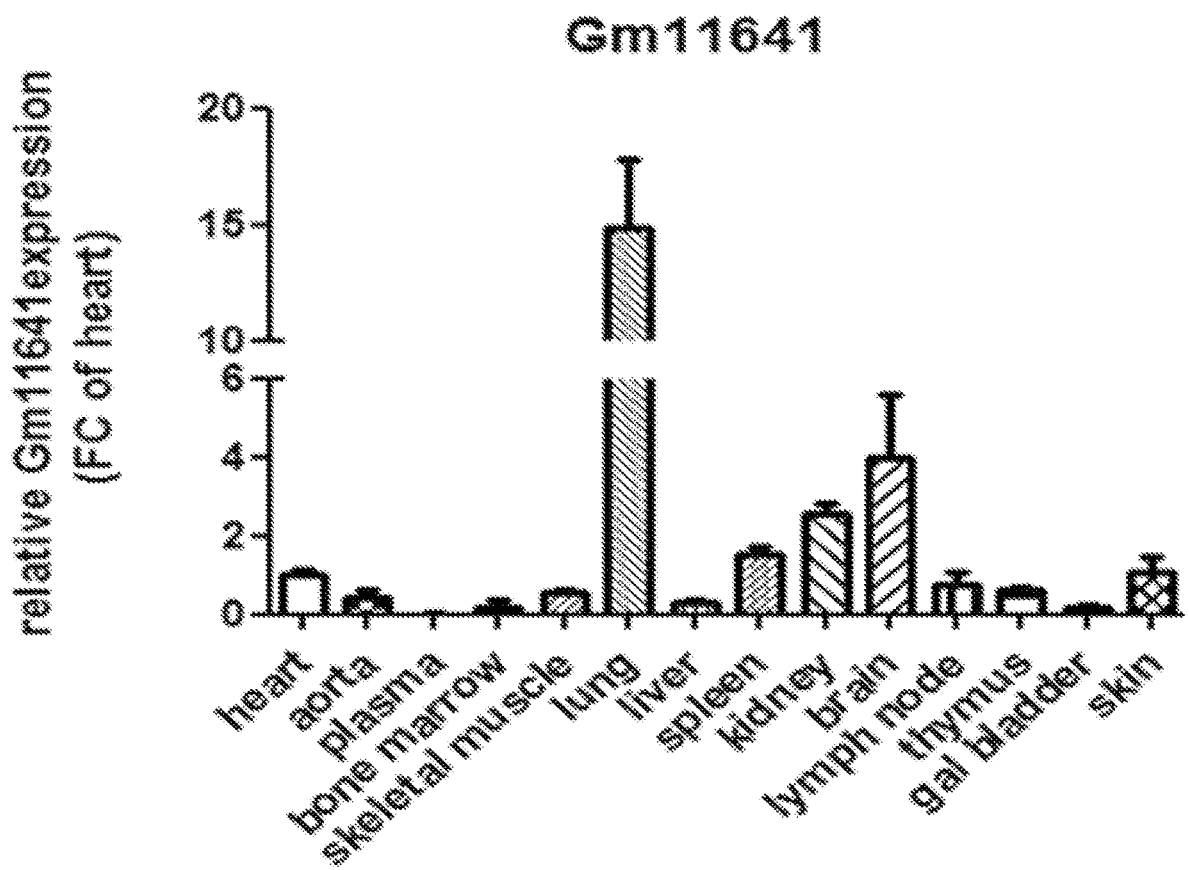
FIG. 3: Organ expression of candidate lncRNA Gm11641. FC—fold change.

To determine the abundance and tissue specific expression of lncRNA Gm11641 in different organs (FIG. 3), its expression was measured in 14 different tissue samples including heart, aorta, plasma, bone marrow, skeletal muscle, lung, liver, spleen, kidney, brain, lymph node, thymus, gall bladder, and skin.

LncRNA Gm11641 is expressed in nearly all organs tested. This includes heart and plasma suggesting this transcript as a potential therapeutic target and diagnostic biomarker.

Figure 4:
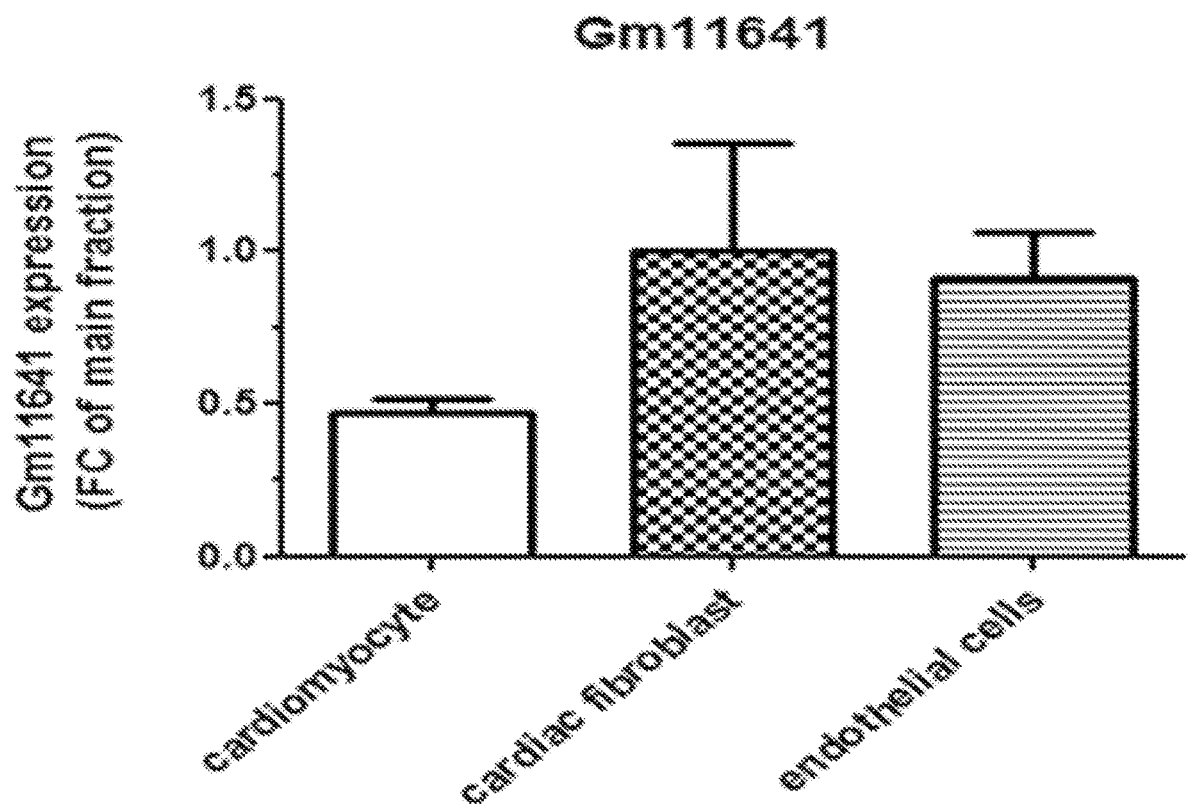
FIG. 4: Expression of candidate lncRNAs in cardiomyocytes, cardiac fibroblasts and endothelial cells derived from mouse hearts. FC—fold change.

1.3 Expression of Candidate lncRNA Gm11641 in Cellular Fractions of the Heart The expression profile of the lncRNA Gm11641 was examined in the three main cell types of the heart: cardiomyocytes, cardiac fibroblasts and endothelial cells (FIG. 4). Therefore, adult mouse heart cells were isolated from several individual hearts applying retrograde perfusion and enzymatic dissociation protocols and determined the levels of lncRNA candidates in each fraction.

LncRNA Gm11641 is expressed in all cardiac cell types.

1.4 LncRNA Gm11641 in Cellular Heart Fractions after TAC

Figure 5A:
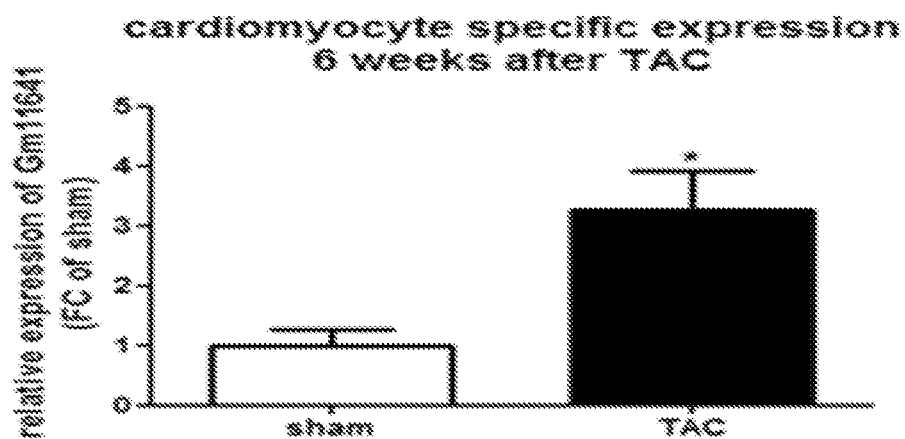
FIG. 5A-C: Expression of lncRNA Gm11641 in cardiomyocytes FIG. 5A, cardiac fibroblasts FIG. 5B, or endothelial cells FIG. 5C 6 weeks after TAC operation. FC—fold change. *p<0.05.
Figure 5B:
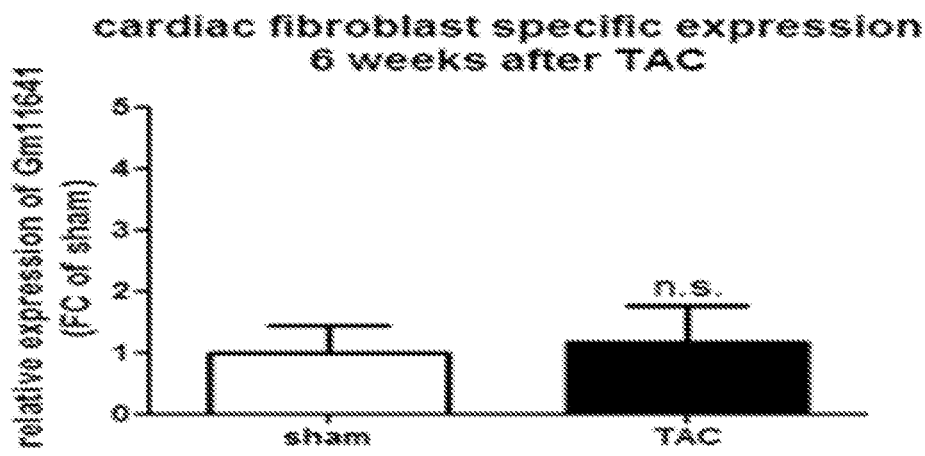
Figure 5C:
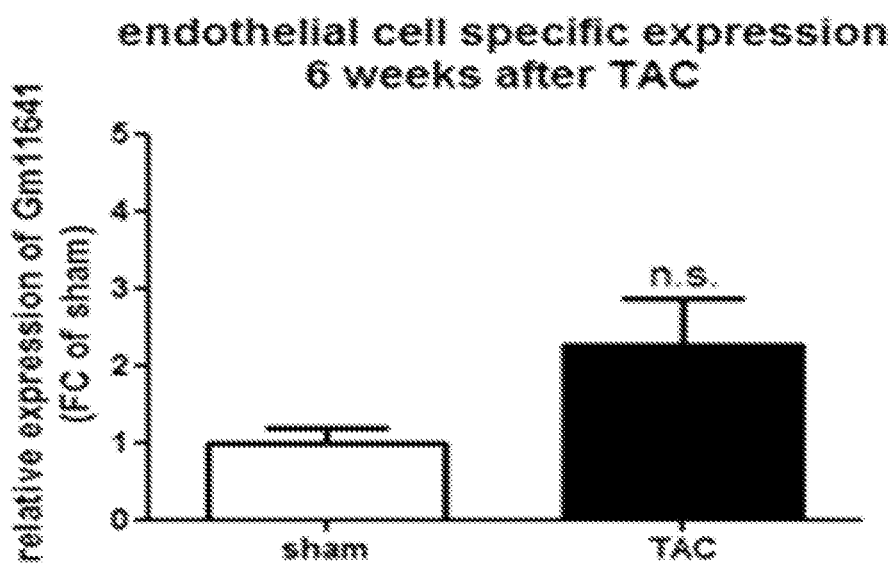

Since lncRNA Gm11641 is expressed in all cardiac cells, it was aimed to identify the specific cell type that contributes to the hypertrophy-induced upregulation of lncRNA Gm11641 observed in whole heart samples (FIG. 2). Cell fractionation experiments using hearts after sham and TAC surgery (6 weeks post operation) showed that this upregulation of lncRNA Gm11641 is specifically observed in cardiomyocytes, but not in cardiac fibroblasts or endothelial cells (FIG. 5), indicating a potential role of lncRNA Gm11641 in cardiomyocyte hypertrophy.

1.5 Subcellular Localization of Candidate lncRNA Gm11641

Figure 6:
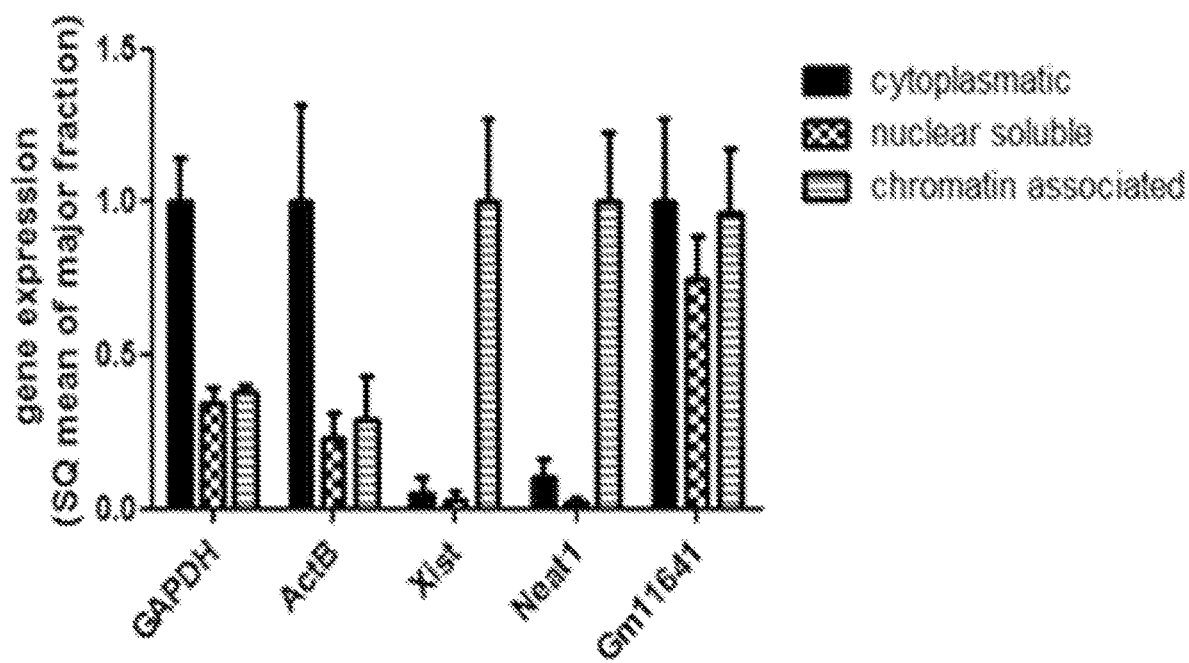
FIG. 6: Subcellular localization of candidate lncRNAs. β-Actin (ActB), GAPDH, Xist and Neat1 were analyzed as controls.

The biological function of lncRNAs is strongly determined by their subcellular localization. Therefore, a biochemical separation of the total RNA derived from HL-1 cells (a cardiomyocyte cell line) into cytoplasmatic, nuclear-soluble and chromatin-associated fraction was performed (according to: Cabianca et al Cell. 11; 149(4):819-31.). The relative abundance of lncRNA Gm11641 in the different fractions was measured by RT-PCR. The known housekeeping genes GAPDH and β-Actin as well as the lncRNAs Xist and Neat1 were used as controls for cytoplasmatic localization or chromatin-bound enrichment, respectively (FIG. 6).

As expected the housekeeping mRNAs Gapdh and β-actin (ActB) were predominantly found in cytosol, while known epigenetic modulators such as Xist and Neat1 lncRNAs were predominantly found associated with chromatin. Compared to cytoplasmatic or chromatin-associated transcripts, lncRNA Gm11641 seems to be present in all subcellular fractions (cytosol, nuclear soluble and chromatin associated), suggesting a potential role in all cellular compartments. This furthermore indicates that lncRNA Gm11641 may modulate both transcriptional and post-transcriptional processes.

1.6 Overexpression of Candidate lncRNA Gm11641

Figure 7:
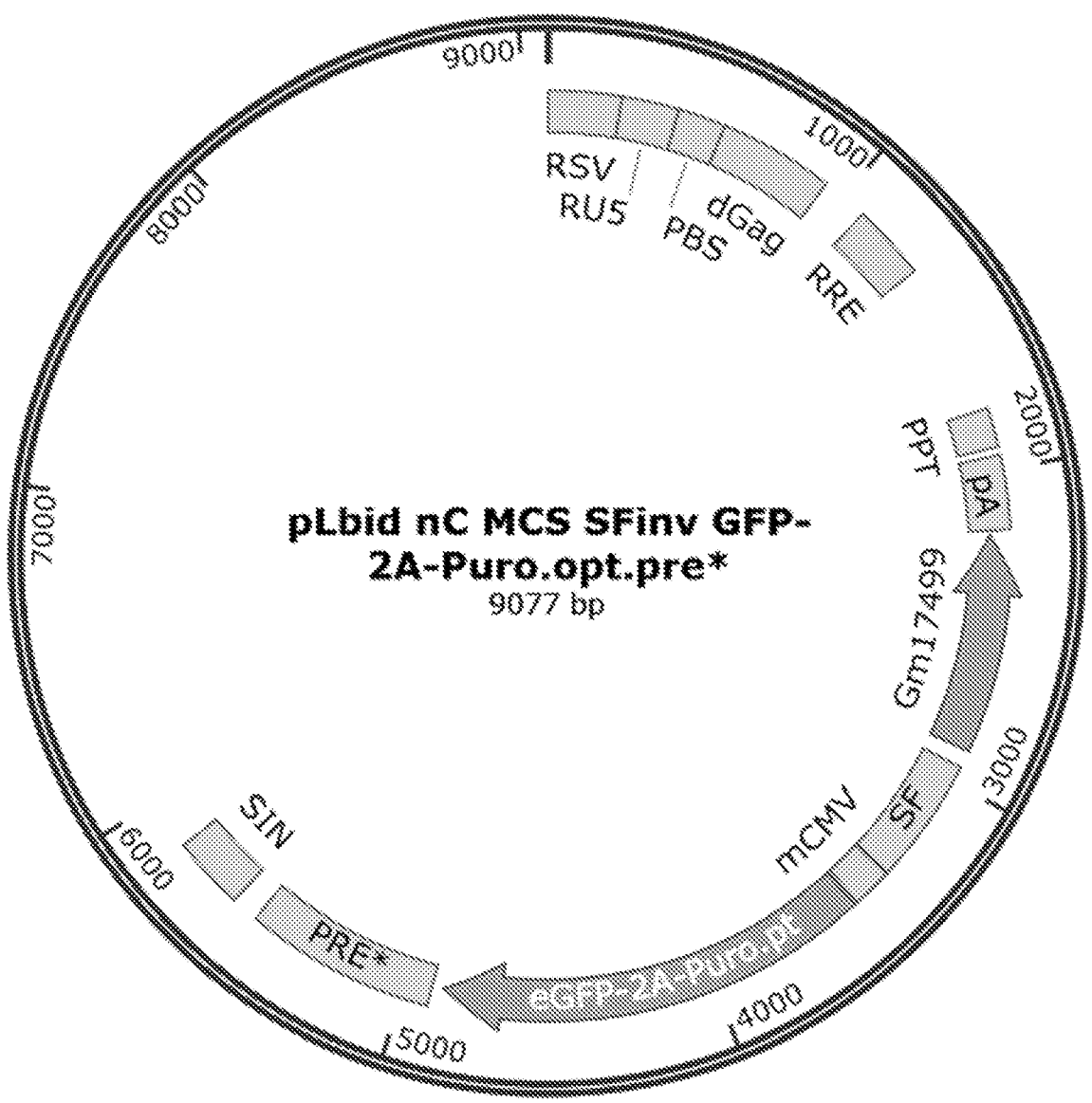
FIG. 7: Representation of the lentiviral overexpression plasmid, designated as pLV+, harboring the full transcript sequence of a lncRNA (e.g. in this case lncRNA Gm17499).

To stably overexpress lncRNA Gm11641, the full length transcript derived from the corresponding database (see Tab. 1) was cloned into the multiple cloning site (MCS) of a lentiviral overexpression vector (kindly provided by A. Schambach, Institute of Experimental Hematology, MHH). This plasmid harbours a bidirectional promoter that allows the production of the lncRNA transcript from the same gene regulatory element, but physically decoupled from the indicator gene GFP (green fluorescent protein) and a selection cassette. By lentiviral transduction the construct was introduced into HL-1 cardiomyocytes (see FIG. 7).

Figure 8:
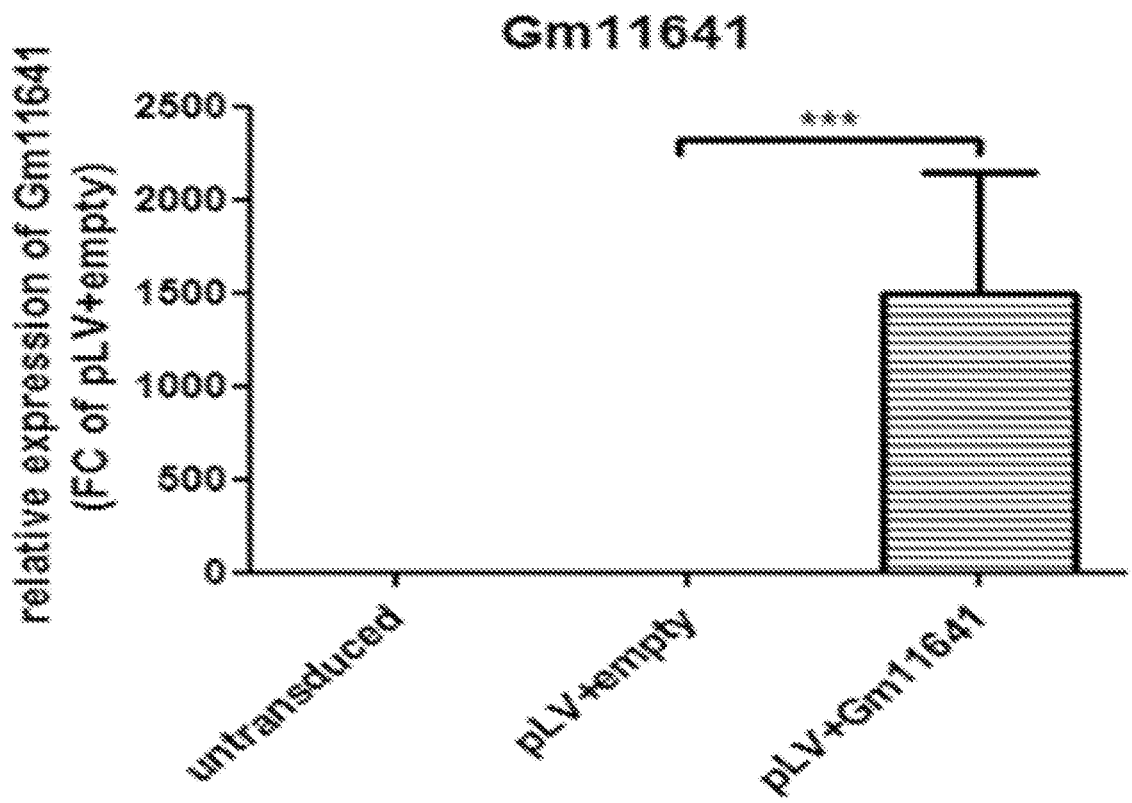
FIG. 8: Lentivirus-mediated overexpression of lncRNA Gm11641. FC—fold change. ***p<0.001.

Lentivirus-mediated transduction of HL-1 cells showed a stable overexpression of lncRNA Gm11641 compared to cells harbouring the empty vector (pLV+empty) or lacking the construct (untransduced) (FIG. 8).

1.7 Repression of lncRNAs

To downregulate lncRNA Gm11641 applied GapmeR antisense oligonuleotides. LNA™ GapmeRs (Exigon) contain a central stretch of DNA monomers flanked by blocks of modified nucleotides (LNA, locked nucleic acids). The DNA gap activates the RNAse H-mediated degradation of targeted RNAs and is also suitable to target transcripts directly in the nucleus. With this technology the lncRNA Gm11641 was successfully downregulated in the cardiomyocyte cell line HL-1 (FIG. 9).

1.8 Functional Characterization of Candidate lncRNA Gm11641

1.8.1 In Vitro Effect of Hypertrophied Cardiomyocytes on Gm11641 Levels

Figure 10:
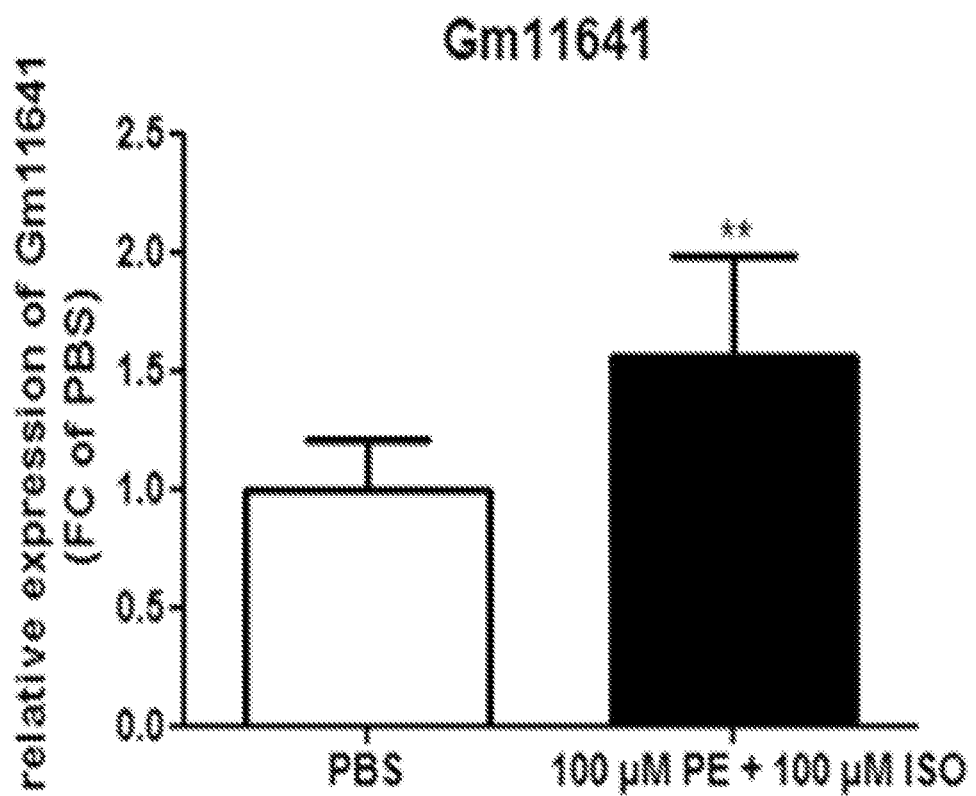
FIG. 10: LncRNA Gm11641 expression in HL-1 cells upon hypertrophic stimulation with phenlyephrine (PE) and isoproterenol (ISO). Expression levels have been evaluated after 48 h of stimulation. **p<0.01.

Cardiomyocyte hypertrophy is an adaptive response on the cellular level to pressure or volume stress in the heart. In vitro hypertrophic growth can be induced by stimuli including phenylephrine (PE) and isoproterenol (ISO). Therefore, HL-1 cells were stimulated with both compounds and investigated the influence on the expression of Gm11641 (FIG. 10).

1.8.2 Influence of Gm11641 Deregulation on Cardiomyocyte Size

The hallmark of hypertrophied cardiomyocytes is an increase in cell size, relative to non-hypertrophic cells. Therefore, the cell size of HL-1 cells was investigated after stimulation with PE and ISO as well as the repressed and elevated expression of lncRNA Gm11641 applying the deregulation tools described above. Results are exemplary given in FIG. 11.

Under basal conditions, the overexpression of lncRNA Gm11641 leads to an increase of cell size measured by cell surface area, showing that this transcript is sufficient to induce cardiomyocyte hypertrophy. In accordance, GapmeR-based repression of lncRNA Gm11641 reduced cardiomyocyte size and further attenuated the PE/ISO-induced increase of cell size. These results demonstrate a pro-hypertrophic function of the lncRNA Gm11641.

1.8.3 Influence on Hypertrophy-Associated Genes

Figure 12A:
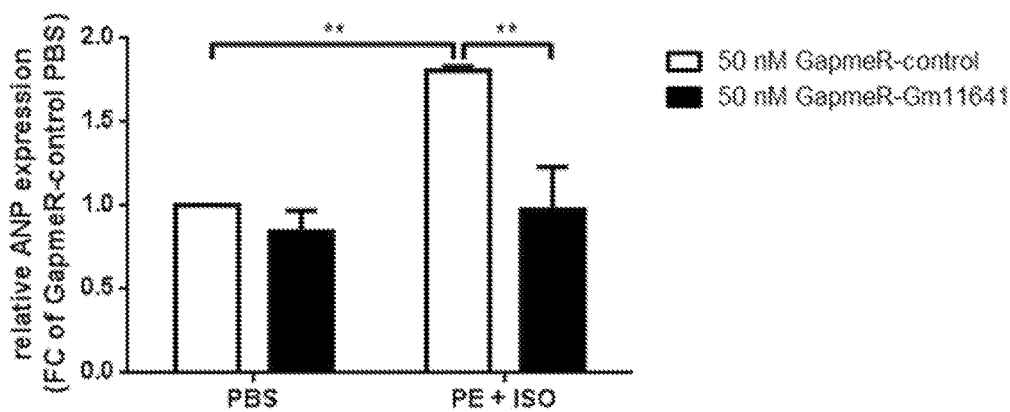
FIG. 12A-B: Expression of arterial natriuretic peptide (ANP) under hypertrophic conditions and deregulation of lncRNA Gm11641. *p<0.05, n.s.=not significant.
Figure 12B:
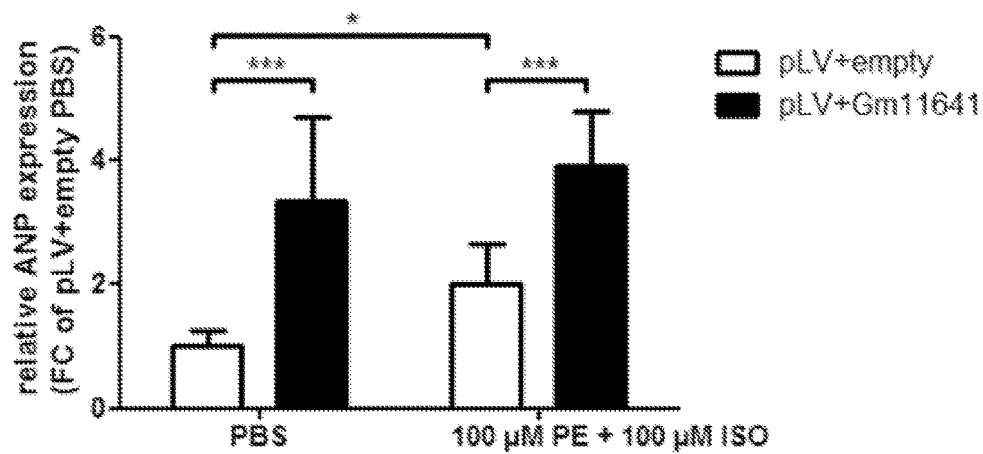

Hypertrophy-induced cardiomyocyte growth is accompanied by reinduction of the "fetal gene program", because gene expression patterns mimic those seen during embryonic development. Applying the same conditions (stimulus and deregulation) regarding the candidate lncRNA Gm11641 expression levels of hypertrophy-associated genes including ANP, BNP (arterial and brain natriuretic peptide), Mcip1.4 (modulatory calcineurin-interacting protein 1, exon 4 isoform), α- and β-MHC (myosin heavy chain) were measured. FIG. 12 represents the result for ANP, while the measurements of the other genes are not shown.

Comparable to the cell size measurement, overexpression of lncRNA Gm11641 leads to an expression induction of the hypertrophy indicator ANP, while the knockdown augmented PE/ISO-induced ANP elevation, supporting that lncRNA Gm11641 acts as a pro-hypertrophic transcript.

1.8.4. Microarry Expression Data

In order to identify cardiac relevant genes that are modulated by Gm11641, global microarray mRNA expression analysis was performed upon lentiviral over-expression or GapmeR-mediated suppression of Gm11641 (alias Chast) in the murine HL-1 cardiomyocyte cell line. Results indicated that either Gm11641 up-regulation or suppression have a strong effect on HL-1 cardiomyocyte transcriptome. A number of cardiac relevant genes such as Axl, Pak3, Myo18B, Egr1, Ogn and Noslap (Tab. 2) are reciprocally regulated after Gm11641 over-expression and suppression. These results indicate that deregulation of Gm11641 expression effects the transcriptional mRNA expression profile and activates pro-hypertrophic pathways in cardiomyocytes.

TABLE 2

Microarray results of reciprocal regulated mRNAs upon Gm11641 silencing (GapmeR) and overexpression (pLV+). FC = fold change.

|  | GapmeR (FC) | pLV+ (FC) |
| --- | --- | --- |
| Axl | −1,499 | 1,510 |
| Pak3 | −1,423 | 1,345 |
| Egr1 | −1,798 | 1,366 |
| Ogn | −1,192 | 1,207 |
| Myo18b | 1,405 | −1,477 |
| Noslap | 1,487 | −2,067 |

1.9 Conservation

To identify the homolog of lncRNA Gm11641 in further species including humans, BLAST was applied, being an algorithm for the comparison of primary DNA sequences with a library of a sequence database. Results of this alignment lead to the following results (Tab. 2):

TABLE 3

BLAST-based sequence comparison of transcript Gm11641 with different species.

|  | *Ratus norvegicus* | | *Homo sapiens* | | *Sus scrofa* | | *Danio reiro* | |
| --- | --- | --- | --- | --- | --- | --- | --- | --- |
|  | coverage | identity | coverage | Identity | coverage | identity | coverage | identity |
| Gm11641 | 99% | 94% | 34% | 81% | 39% | 81% | — | — |

Figure 13A:
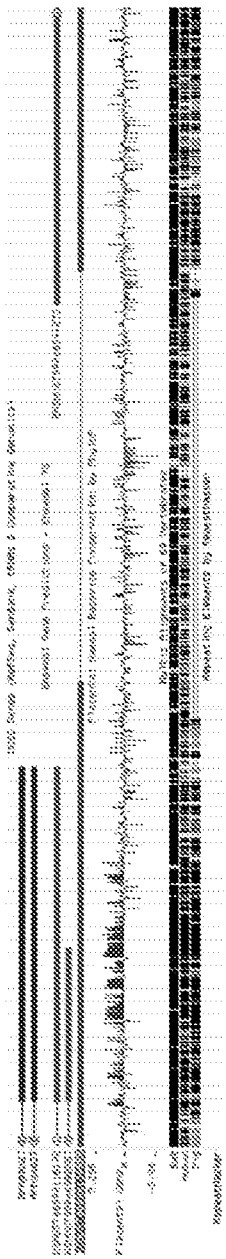
FIG. 13A-E.

The UCSC genome browser was used to depict an alignment across species (FIG. 13A). The alignment identified the human homolog of the mouse lncRNA Gm11641.

Figure 13B:
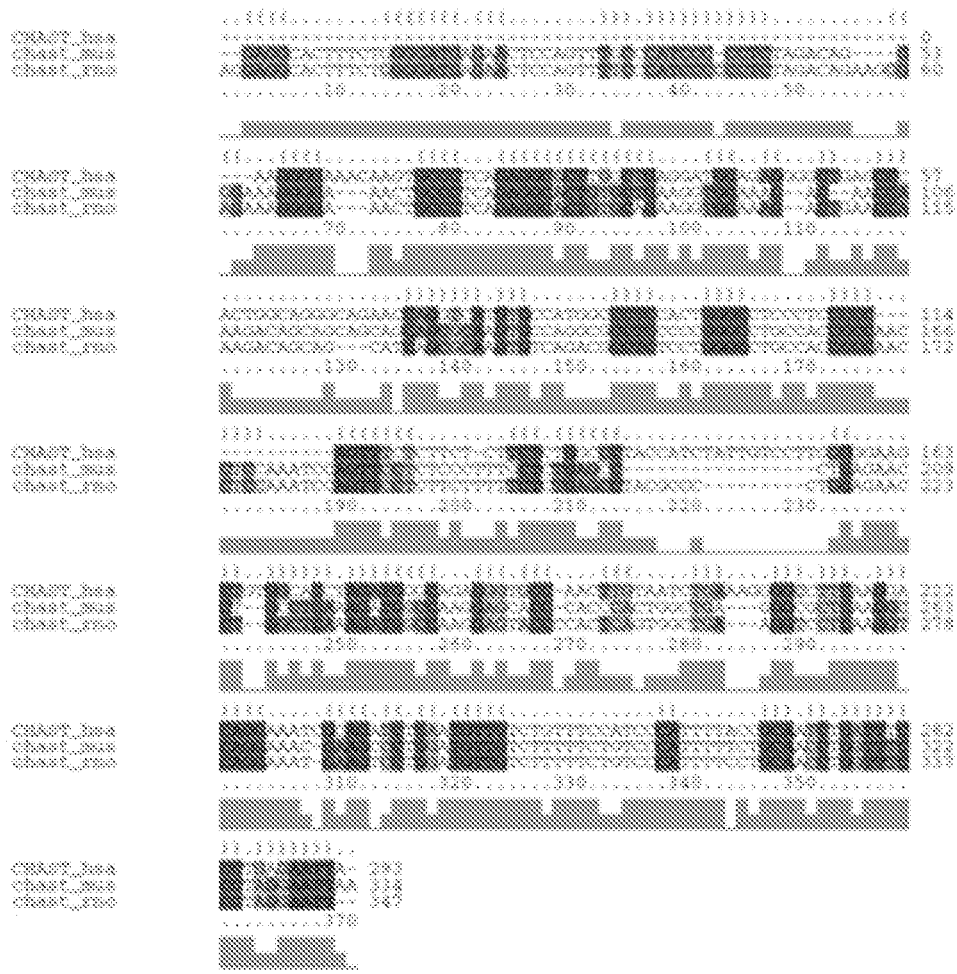
Figure 13C:
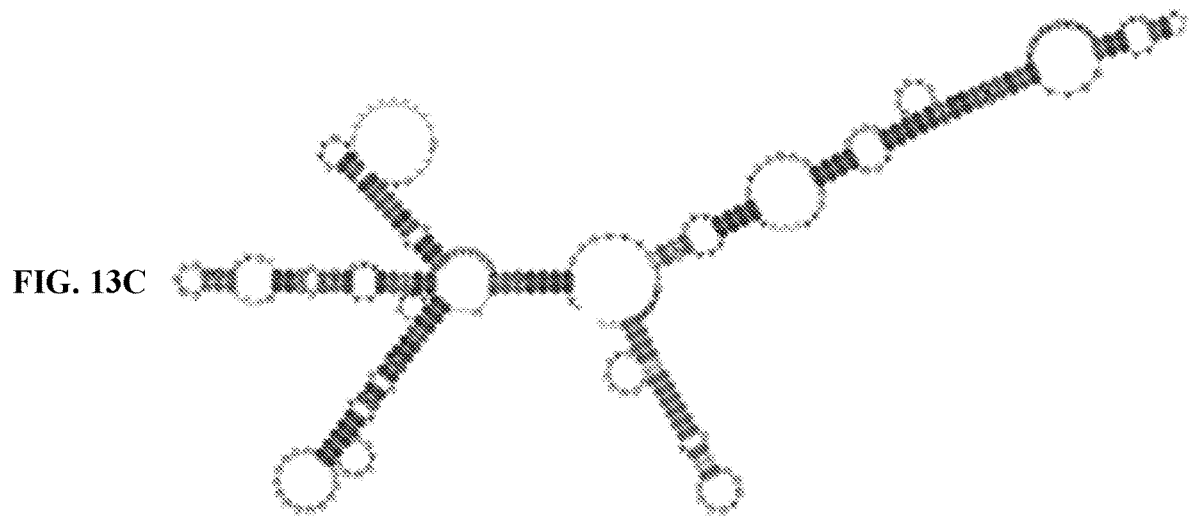
Figure 13D:
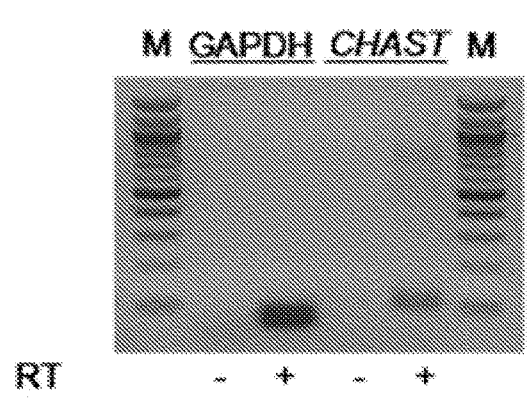
Figure 13E:
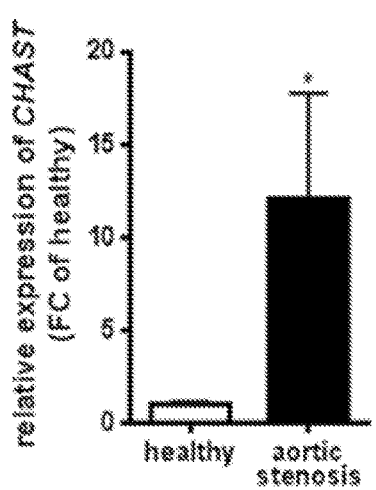
Figure 14A:
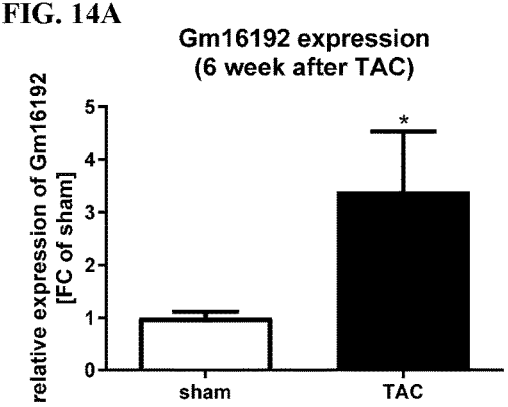
FIG. 14A-F: Validation of candidate lncRNAs in whole heart samples of TAC hearts compared to tissue of sham animals. FC—fold change.). ***p<0.001, *p<0.05, n.s.=not significant.
Figure 14B:
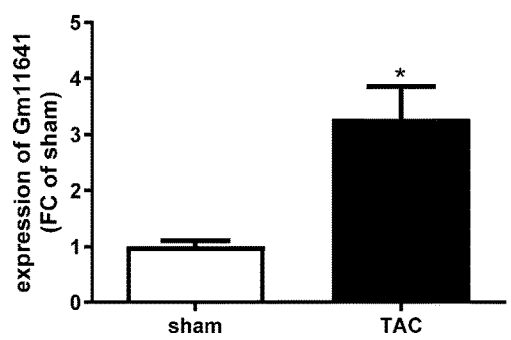
Figure 14C:
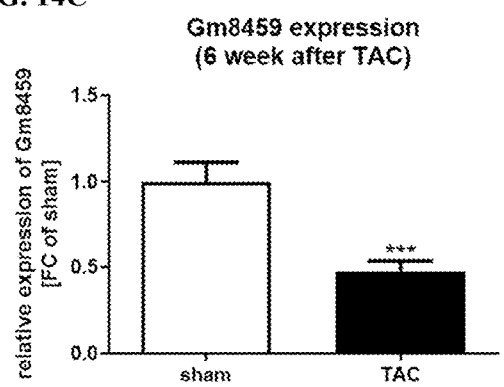
Figure 14D:
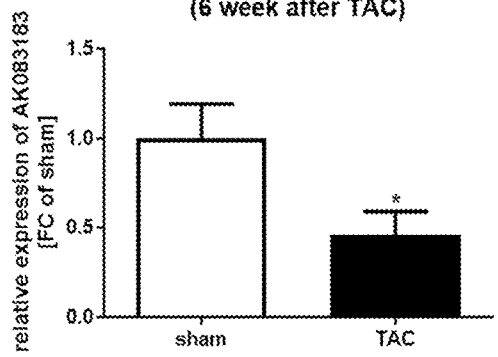
Figure 14E:
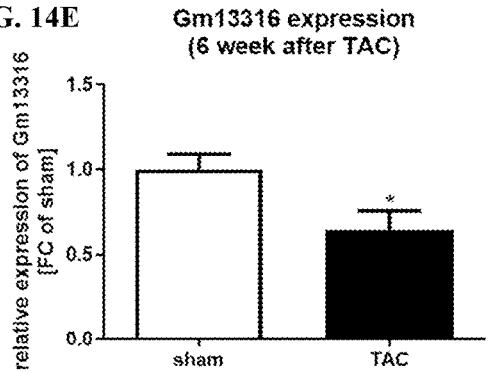
Figure 14F:
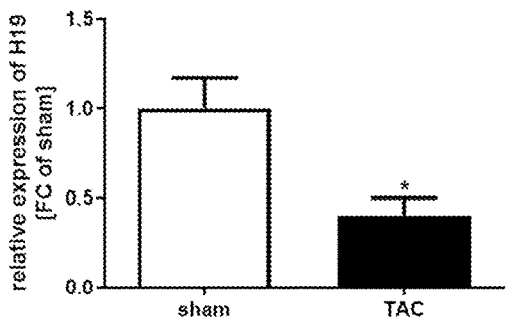

A more detailed sequence and structure alignment of Gm11641 revealed that Gm11641 homologs exist in rat, pig and humans located in intron of a protein coding gene Plekhm in antisense orientation (FIG. 13B). The human homolog is annotated as:

gi|528476558|ref|NC_018928.2|:62843244-62843536 *Homo sapiens* chromosome 17, alternate assembly CHM1_1.1., or gi|568815581:64783259-64783551 *Homo sapiens* chromosome 17, GRCh38.p2 Primary Assembly Presence of a Gm11641 homolog in human heart tissues was verified by gene-specific PCR (FIG. 13B). Complementary DNA (cDNA) was prepared from RNA isolated from total human heart tissues. cDNA preparation reaction without reverse transcription served as internal control to rule-out any possible amplification of contaminating DNA.

Next the expression of this human homolog was examined in 23 control hearts and 21 hypertrophic hearts from patients with aortic stenosis. In line with the results obtained in hypertrophic mouse hearts, the human Gm11641 homolog is also upregulated in human hypertrophic heart tissue (FIG. 13B), evidencing that the findings of this study have a translational potential.

1.10 Regulation of Gm11641 Expression

In cardiomyocytes, the hypertrophic response is orchestrated by growth factors and cytokines influencing several signalling cascades, especially the calcium dependent signalling. The transcription factor NFAT (nuclear factor of activated T-cells) is a central regulator in this pathway, finally leading to the activation of the pro-hypertrophic program.

Therefore, it was determined if this central regulator has an impact on the expression of Gm11641. Bioinformatic tools predict binding sites for several hypertrophy-related transcription factors in the Gm11641 promoter. This includes also NFAT binding sites (FIG. 36).

To study the influence of NFAT in more detail, the expression of Gm11641 was assessed in calcineurin transgenic mouse hearts and an induction of Gm11641 expression was found upon constitutively activated NFAT signalling. In vitro, inhibition of NFAT by 11R-VIVIT led to reduced levels of Gm11641 in HL-1 cardiomyocytes. This data indicates that Gm11641 expression depends on the pro-hypertrophic NFAT pathway.

1.11 In Vivo Studies of Gm11641

Pathological hypertrophy is a response to stress or disease such as hypertension, injuries of the heart muscle, heart valve stenosis, or neurohormones. This leads to an increase in heart muscle mass and finally to a thickening of the ventricular walls, especially of the left ventricle. Although the muscle mass is elevated, the pumping ability of the heart is not increased. On the contrary, the performance of the heart is disturbed and can finally lead to a complete failure.

Figure 37A:
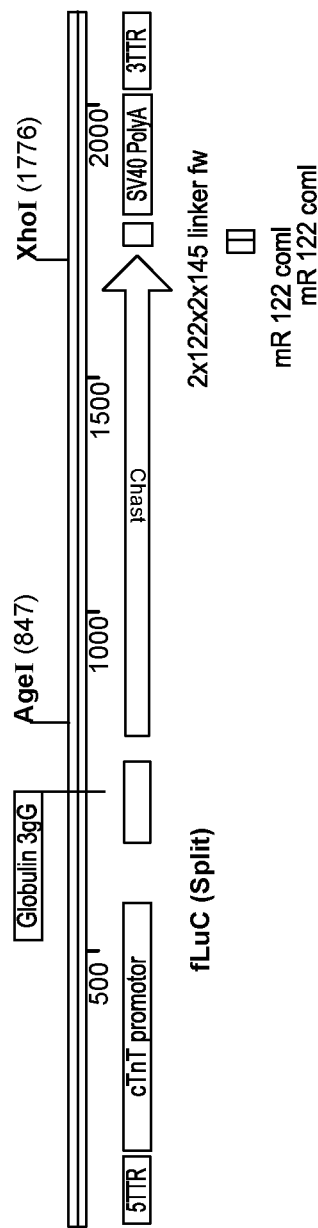
FIG. 37A-B: Cardiac specific overexpression of Gm11641 in mice applying AAV9 (6 weeks post injection). Depiction of the AAV9 construct FIG. 37A and the overexpression efficiency in mouse hearts compared to the control vector FIG. 37B n=3. *p<0.05; FC=fold change, Gm11641 is referred to in FIG. 36 as "Chast".
Figure 37B:
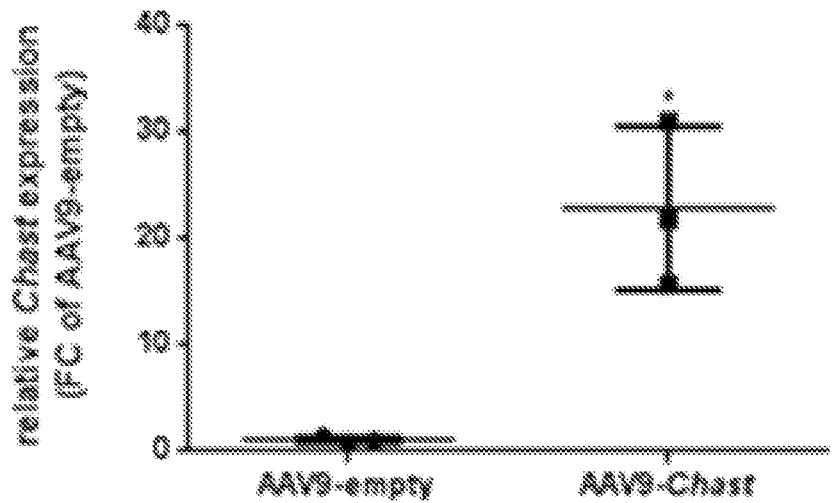
Figure 38A:
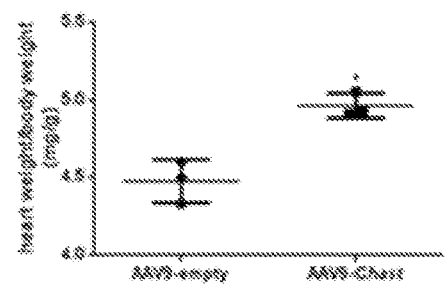
FIG. 38A-D: Overexpression by AAV9-Gm11641 in vivo for 6 weeks leads to cardiac hypertrophy (0.5+E12 copies per animal). This led to an induction of the FIG. 38A heart-to-body-weight ratio and the FIG. 38B left ventricular mass as well as an enlargement of the cardiomyocyte diameter. n=3. *p<0.05. LV mass=left ventricular mass, DAPI=4',6-diamidino-2-phenylindole (DNA stain); WGA=wheat germ agglutinin (membrane stain), a.u.=arbitrary unit, Gm11641 is referred to in FIG. 38 as "Chast".
Figure 38B:
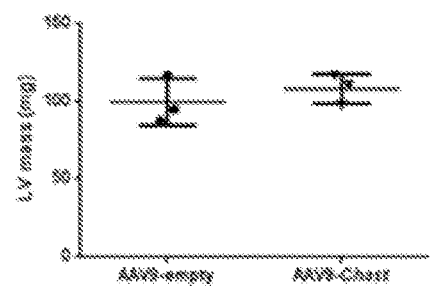
Figure 38C:
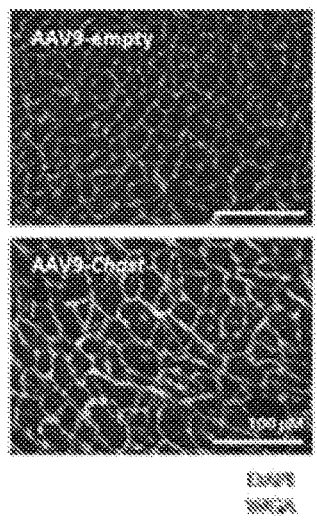
Figure 38D:
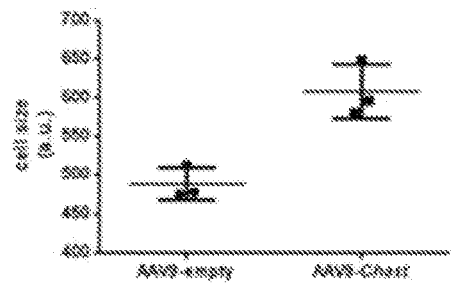

To analyze the role of Gm11641 in vivo this transcript was overexpressed applying adenoviral vectors (AAV). AAV is small virus lacking an envelope and harboring a single-stranded DNA. To transfer the genetic material, AAV depends on a helper virus. However, transduction of AAV vectors does not result in the expression of further viral genes contributing to their low immunogenicity. Among all serotypes, AAV9 appears to be the most cardiotropic one. Therefore, an AAV9 was applied under the control of the cardiac-specific troponin T promoter to achieve an induction of Gm11641 directed to cardiomyocytes (FIG. 37).

Applying the AAV9-Gm11641 construct, a 20-fold induction of Gm11641 was achieved in whole heart samples. On the functional level, an induction of the heart to body weight ratio was observed (FIG. 38, upper left), indicating that Gm11641 overexpression increases the muscle mass of the left ventricle (FIG. 38, upper right). The size of cardiomyocytes was further analyzed and it was found that Gm11641 induces cardiomyocyte growth (FIG. 38, lower).

Figure 39:
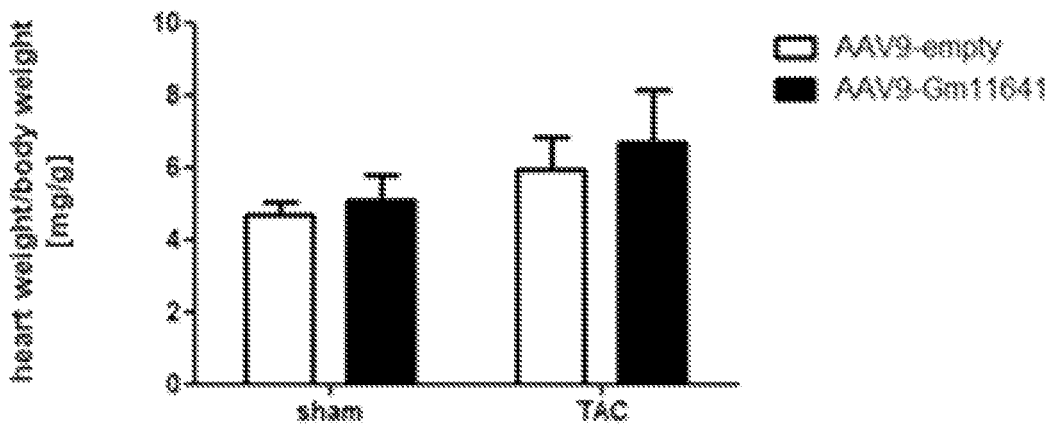
FIG. 39: TAC operation and overexpression of Gm1164 by AAV9 (0.5+E12 copies per animal) for 6 weeks led to an induction of the heart-to-body-weight ratio. n=5–8.

Further, left ventricular pressure overload was applied by TAC operation and Gm11641 was overexpressed by AAV9 for 6 weeks. As expected, the aortic constriction led to an increase in the heart-to-body-weight ratio, as well as the simple injection of AAV9-Gm11641. Interestingly, TAC operation and AAV9-Gm11641 administration exacerbated the induction of the heart mass (FIG. 39).

1.12 Conclusion

In conclusion, based on the findings in the tested cardiac hypertrophy models on the lncRNA Gm11641 this lncRNA is of diagnostic and therapeutic value for cardiac hypertrophy.

Example 2—Identification of Pro-Hypertrophic and Anti-Hypertrophic lncRNAs 2.1 lncRNA Profiling and Validation To achieve general lncRNA profiling Microarray analysis was performed applying platforms provided by Agilent/Life Technologies (NCode™ Mouse Non-coding RNA Microarrays) and Arraystar (Arraystar Mouse LncRNA microarray V2.0). Candidate transcripts were verified as being expressed in heart tissue via PCR (in cDNA samples derived from RNA treated with DNAse I or not prior reverse transcription) and the deregulation validated by real-time PCR.

The following Tables 3 and 4 and FIGS. 14 and 15 summarize candidate lncRNAs that have been validated from different Microarrays:

TABLE 4

LncNA candidates derived from Arraystar Mouse LncRNA microarray V2.0 analyzing whole heart samples from 6 week sham and TAC mice.

| Name | Identifier | Source | Size | relationship | related gene | FC | Regulation |
|---|---|---|---|---|---|---|---|
| Gm16192 | ENSMUST00000148357 | Ensembl | 937 bp | antisense | Mtus1 | 4, 20 | Up |
| Gm11641 | ENSMUST00000130556 | Ensembl | 923 bp | antisense | Arhgap27 | 3, 85 | Up |
| Gm8459 | ENSMUST00000162504 | Ensembl | 760 bp | intergenic | — | −10, 09 | Down |
| AK083183 | AK083183.1 | Fantom3 | 2759 bp | intergenic | — | −8, 86 | Down |
| Gm13316 | ENSMUST00000140537 | Ensembl | 691 bp | antisense | Cacnb2 | −2, 83 | Down |
| H19 | ENSMUST00000136359 | Ensembl | 2286 bp | intergenic | — | −2, 01 | Down |
| (NR_001592.1) | ENSMUST00000152754 | Ensembl | 1853 bp | intergenic | — | −2, 06 | Down |
| | ENSMUST00000140716 | Ensembl | 817 bp | Intergenic | — | −5, 30 | Down |

TABLE 5

LncNA candidates derived from Arraystar Mouse LncRNA microarray V2.0 analyzing a cardiomyocyte-specific fraction of 12 week healthy vs. 13 week TAC mouse hearts.

| Name | Identifier | Source | Size | relationship | related gene | FC | Regulation |
|---|---|---|---|---|---|---|---|
| AK013700 | AK013700.1 | predicted | 725 bp | intergenic | — | 10, 93 | Up |
| Gm15892-002 | ENSMUST00000152627 | Ensembl | 439 bp | intergenic | — | 9, 54 | Up |
| BCO23483 | uc007dvi.1 | UCSC | 1726 bp | intergenic | — | 6, 52 | Up |
| Gm12224-001 | ENSMUST00000124047 | Ensembl | 567 bp | antisense | AcsI6 | 6, 20 | Up |
| AJ409495 | AJ409495.1 | NRED | 292 bp | intergenic | — | 5, 80 | Up |
| Gm16192 | ENSMUST00000148357 | Ensembl | 937 bp | antisense | Mtus1 | 5, 50 | Up |
| Gm8822-202 | ENSMUST00000168371 | Ensembl | 339 bp | intergenic | — | −10, 12 | Down |
| H19 | ENSMUST00000140716 | Ensembl | 817 bp | intergenic | — | −4, 73 | Down |
| (NR_001592.1) | ENSMUST00000136359 | Ensem bl | 2286 bp | intergenic | — | −2, 48 | Down |

2.2 Organ Expression of Candidate lncRNAs

To determine the expression specificity of lncRNAs in different organs (FIG. 16), the expression of candidate transcripts was measured in 14 different tissue samples including heart, aorta, plasma, bone marrow, skeletal muscle, lung, liver, spleen, kidney, brain, lymph node, thymus, gall bladder, and skin. Most lncRNAs are abundant in several organs. The transcripts Gm8459, H19 and Gm12224-1 seem to be most specifically enriched in muscle tissue including the heart.

2.3 Expression of Candidate lncRNAs in Cellular Fractions of the Heart

The expression profile of candidate lncRNAs was examined in the three main cell types of the heart: cardiomyocytes, cardiac fibroblasts and endothelial cells (FIG. 17). Therefore, adult mouse heart cells were isolated from several individual hearts applying retrograde perfusion and enzymatic dissociation protocols and determined the levels of lncRNA candidates in each fraction.

2.4 Subcellular Localization of Candidate lncRNAs

Figure 18A:
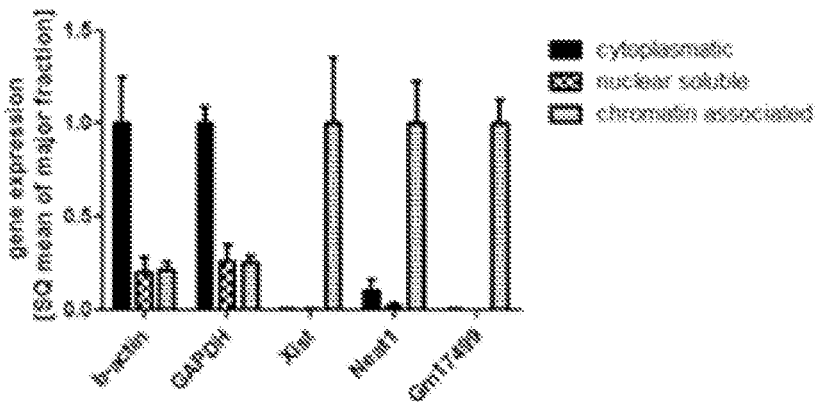
FIG. 18A-C: Subcellular localization of candidate lncRNAs.
Figure 18B:
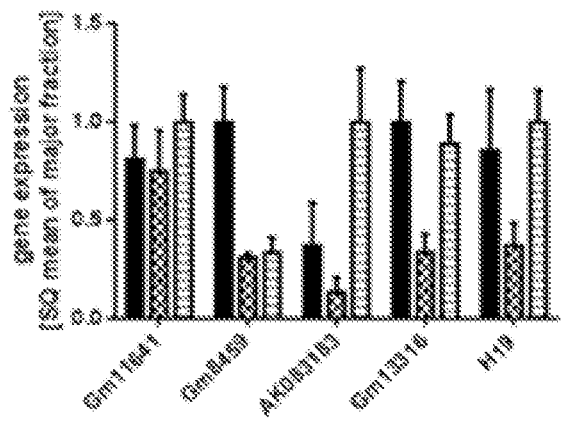
Figure 18C:
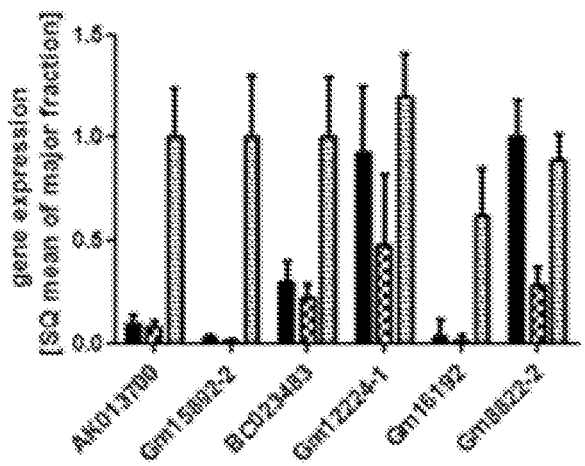

To further elucidate the action mechanism of the candidate lncRNAs, the subcellular localization was analysed by biochemical separation of the total RNA derived from HL-1 cells (a cardiomyocyte cell line) into cytoplasmatic, nuclear-soluble and chromatin-associated fraction. (according to: Cabianca et al Cell. 11; 149(4):819-31.) The relative abundance of the transcripts in the different fractions was measured by RT-PCR. The known genes GAPDH and β-Actin as well as Xist and Neat1 were run as controls for cytoplasmatic localization or chromatin-bound enrichment, respectively (FIG. 18).

More than half of the lncRNA candidates are found to be chromatin-associated, while nuclear soluble lncRNAs are not among the candidates. Only one transcript was enriched in the cytoplasm (Gm8459).

2.5. Overexpression of Candidate lncRNAs

Figure 19:
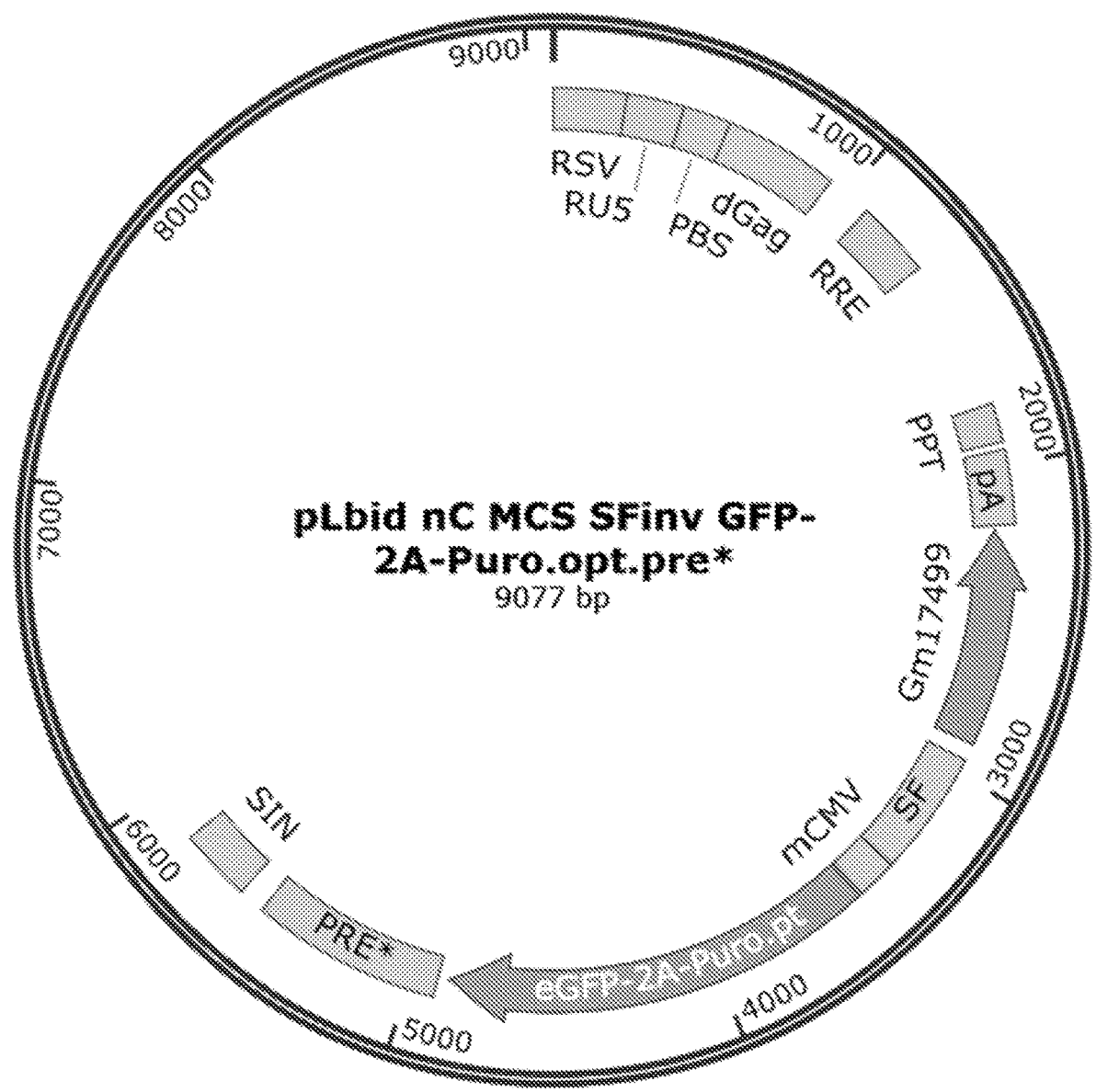
FIG. 19: Representation of the lentiviral overexpression plasmid, designated as pLV+Gm17499, harboring the full transcript sequence of the lncRNA Gm17499.

To stably overexpress candidate lncRNAs, the full length transcript derived from the corresponding database was cloned into the multiple cloning site (MCS) of a lentiviral overexpression vector (kindly provided by A. Schambach, Institute of Experimental Hematology, MHH). This plasmid harbours a bidirectional promoter that allows the production of the lncRNA transcripts from the same gene regulatory element, but physically decoupled from the indicator gene GFP (green fluorescent protein). By lentiviral transduction the construct was introduced into HL-1 cells (see FIG. 19). The following results are given exemplary for the lncRNA candidate Gm17499.

Figure 20:
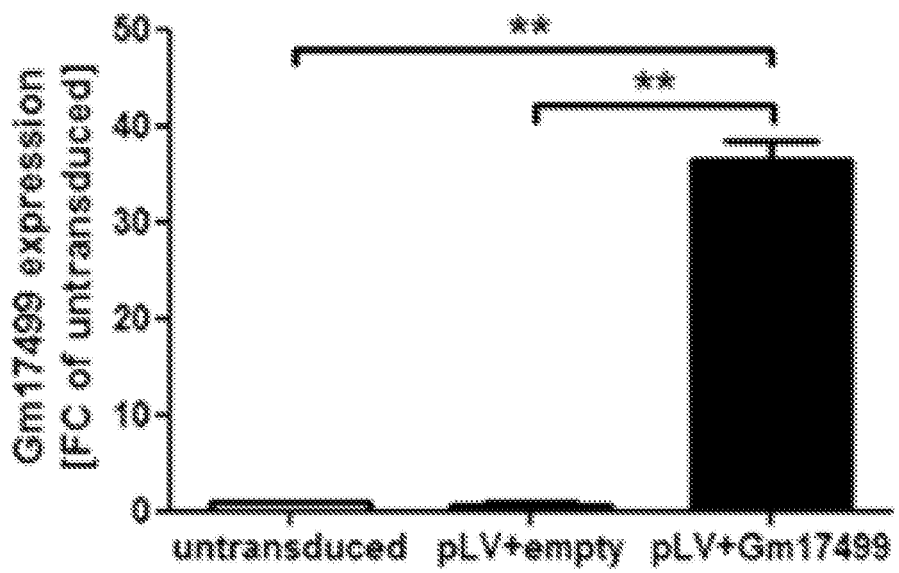
FIG. 20: Lentivirus-mediated overexpression of lncRNA Gm17499. FC—fold change. **p<0.01.
Figure 21A:
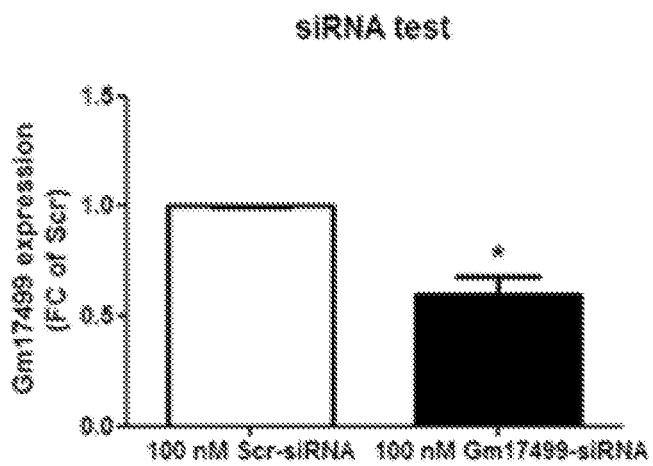
FIG. 21A-E: Test of different antisense chemistries to suppress candidate lncRNA Gm17499. Expression levels have been evaluated after 48 h of incubation time. FC—fold change. *p<0.05, p<0.01, *p<0.001, n.s.=not significant.
Figure 21B:
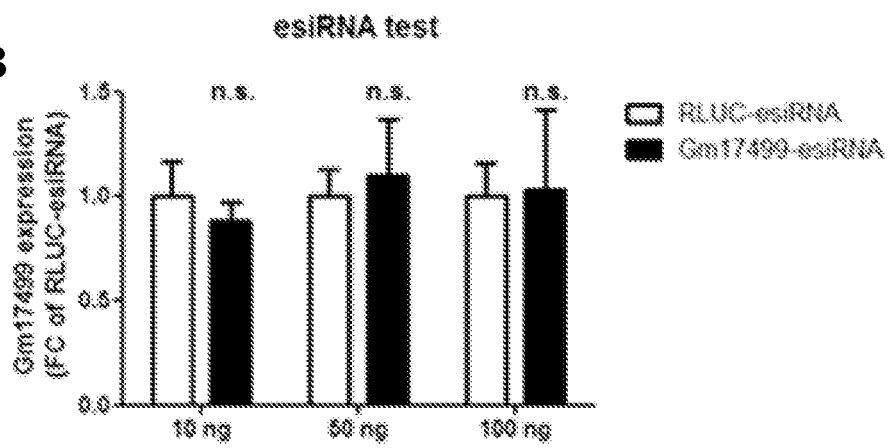
Figure 21C:
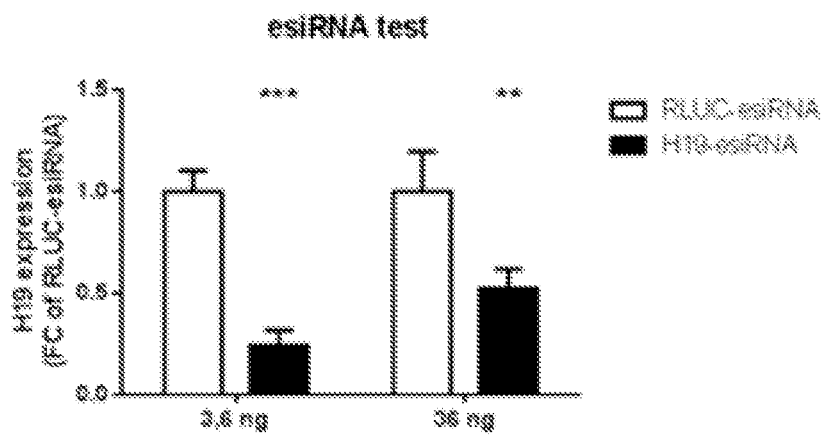
Figure 21D:
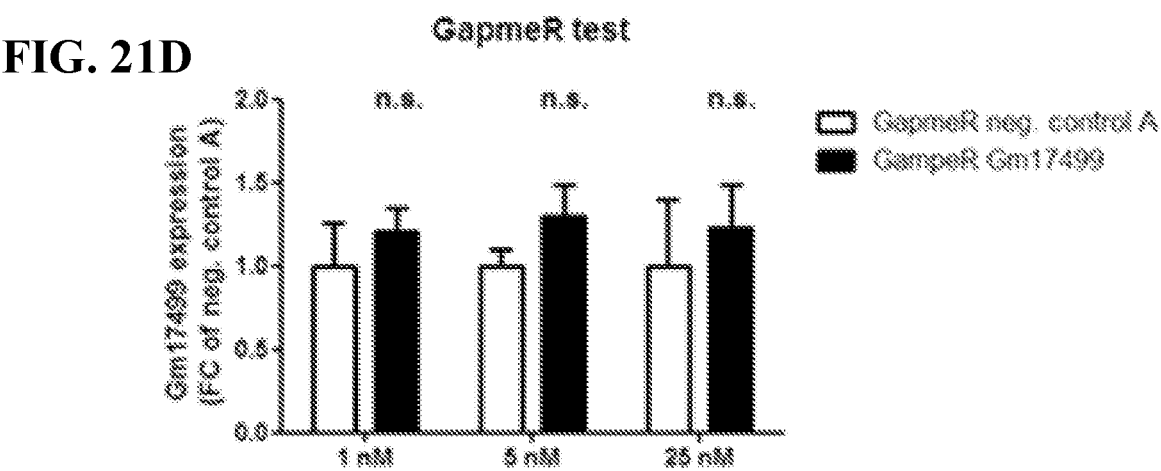
Figure 21E:
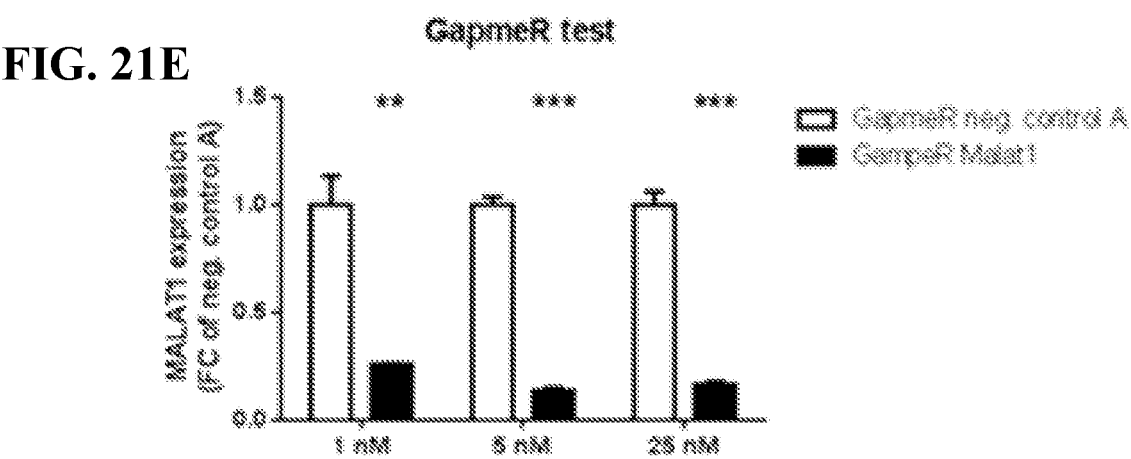
Figure 22A:
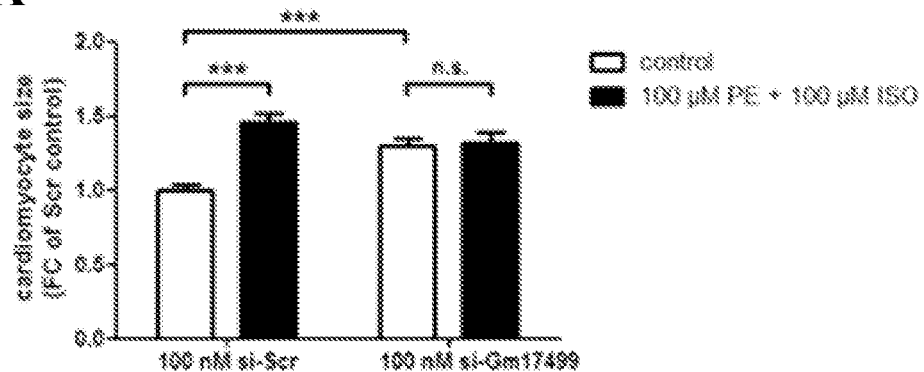
FIG. 22A-D: SiRNA-based silencing and lentivirus-mediated overexpression of lncRNA Gm17499 in HL-1 cells stimulated with phenlyephrin (PE) and isoproterenol (ISO). *p<0.001, p<0.01, *p<0.05, n.s.=not significant. a.u.=arbitrary unit. Scale bar in the picture represents 50 μM.
Figure 22B:
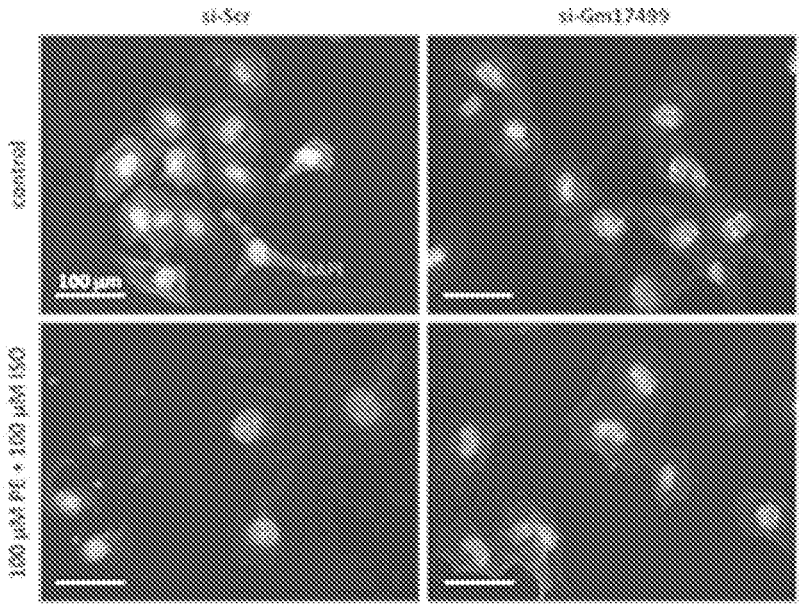
Figure 22C:
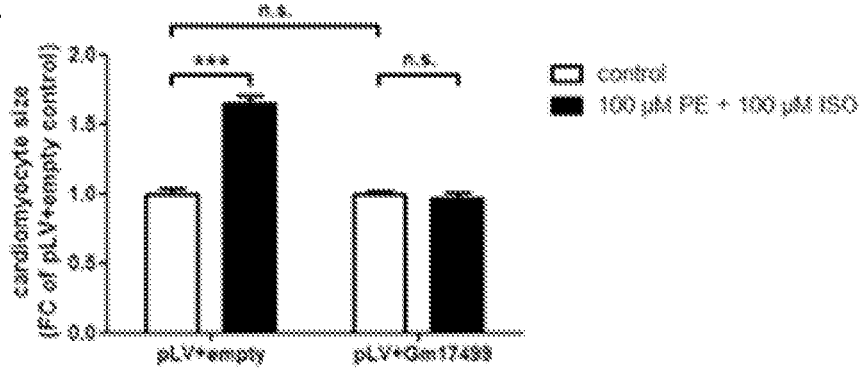
Figure 22D:
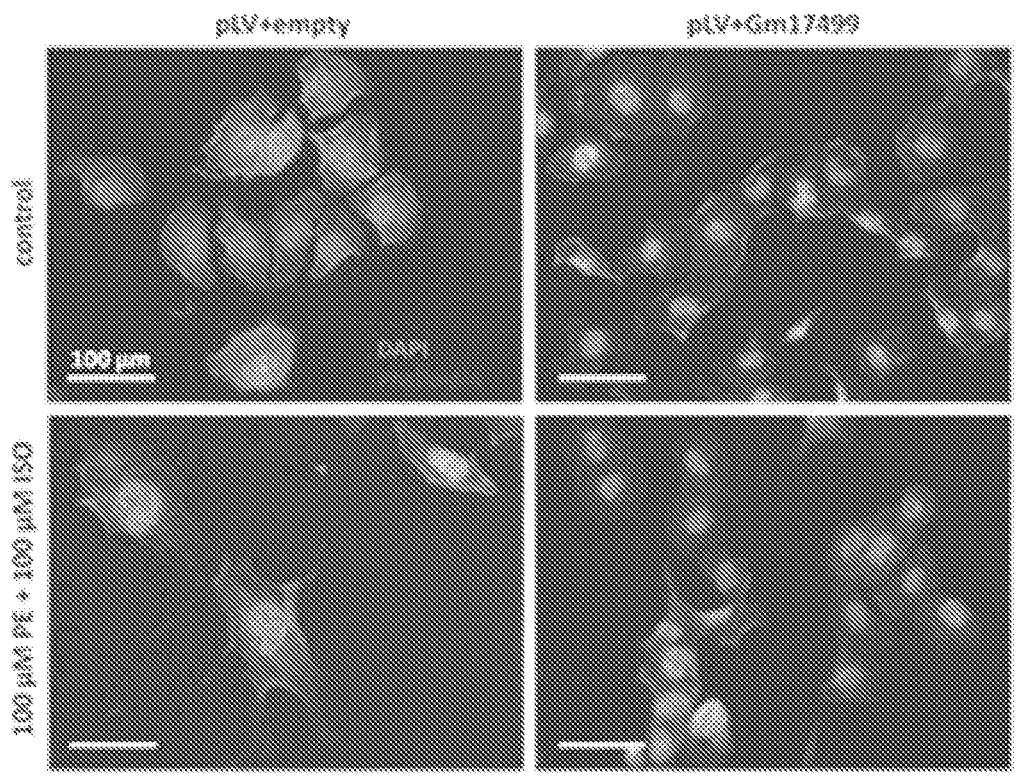
Figure 23A:
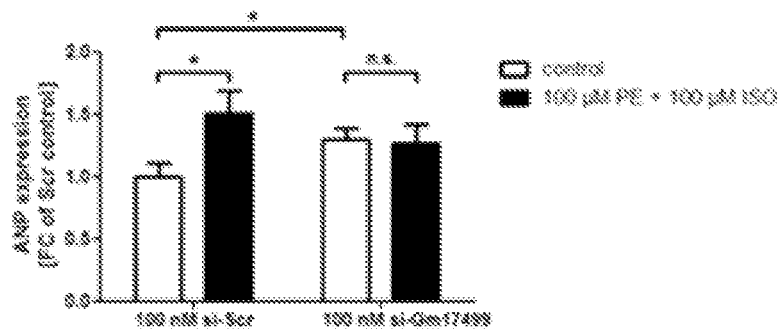
FIG. 23A-F: Expression of hypertrophy-associated genes under hypertrophic conditions and deregulation of lncRNA Gm17499. First row represents expression of ANP, the second that of BNP and the last row shows Mcip1.4 levels. *p<0.05, n.s.=not significant.
Figure 23B:
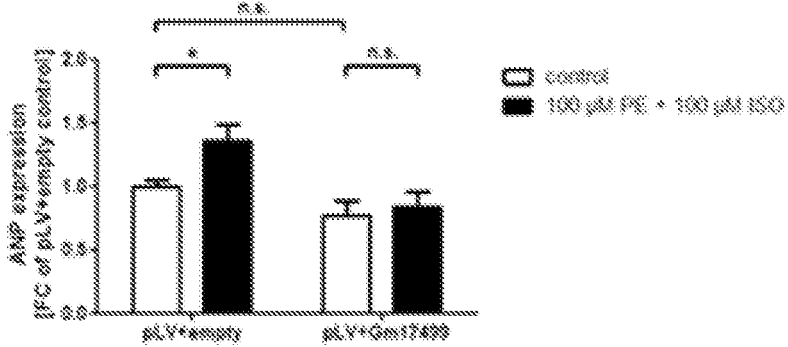
Figure 23C:
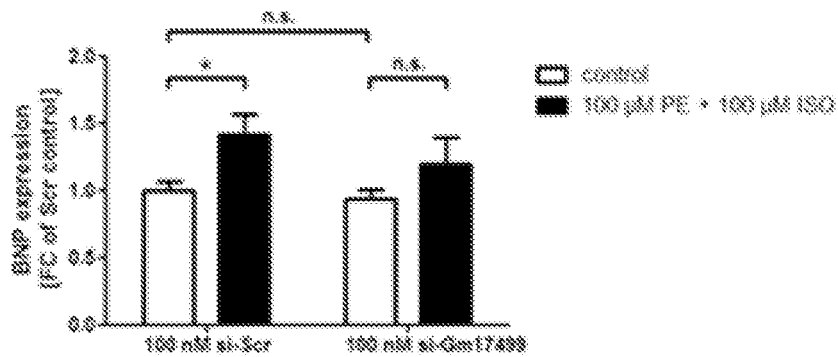
Figure 23D:
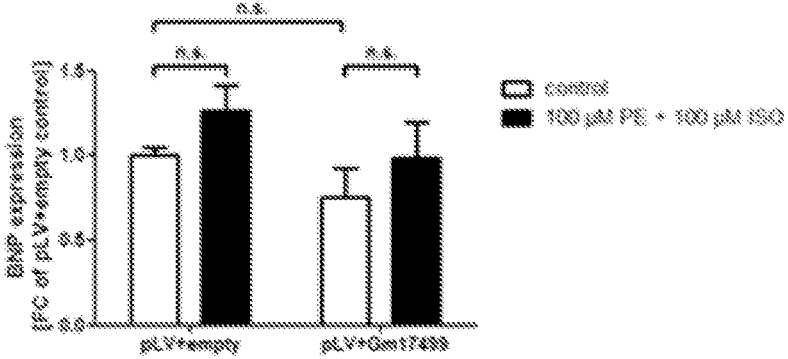
Figure 23E:
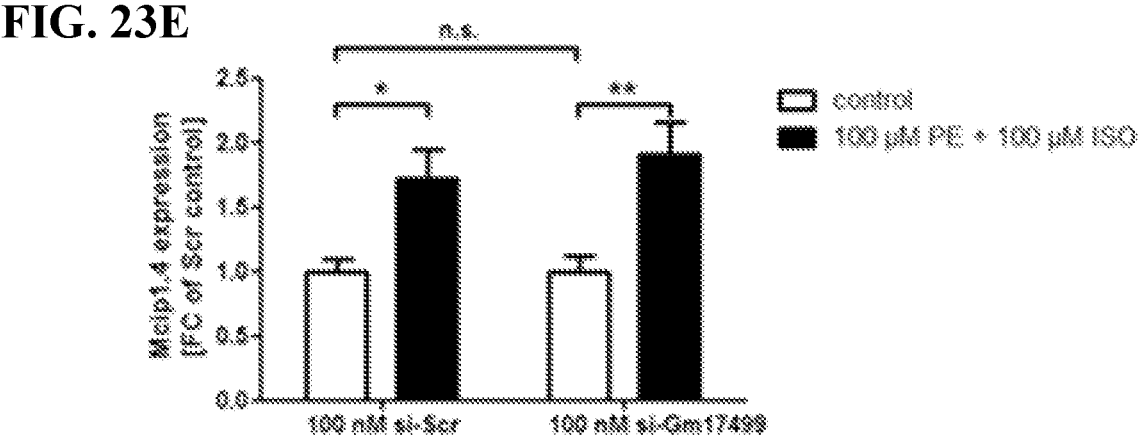
Figure 23F:
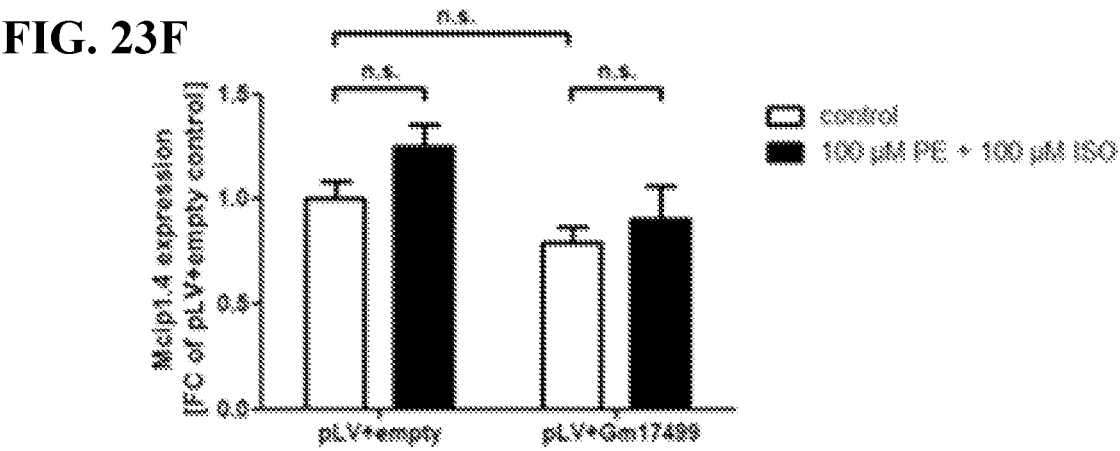

Lentivirus-mediated transduction of HL-1 cells showed a stable overexpression of lncRNA Gm17499 compared to cells harbouring the empty vector (pLV+empty) or lacking the construct (untransduced) (FIG. 20).

2.6 Repression of lncRNAs

To downregulate the lncRNA transcripts three different antisense chemistries were applied: siRNAs, esiRNAs, and GapmeRs. SiRNAs (small interfering RNAs) are, similar to microRNAs, short molecules (20-25 nucleotides) that are involved in the RNA interference pathway. They bind to complementary nucleotide sequences and induce their degradation by a cytoplasmatic localized machinery. EsiRNAs (Eupheria Biotech/Sigma-Aldrich) are endoribonuclease-prepared siRNAs resulting from cleavage of long double-stranded RNAs. This antisense species targets not only one specific sequence as it is the case for siRNAs, but several sequences all over the target. LNA™ GapmeRs (Exigon) contain a central stretch of DNA monomers flanked by blocks of modified nucleotides (LNA, locked nucleic acids). The DNA gap activates the degradation of target RNA and is suitable to target transcripts directly in the nucleus.

Exemplary, the results for Gm17499 applying all three chemistries are shown (FIG. 21) as well as for H19. H19 was successfully downregulated with esiRNA and Malat1 and was repressed applying GapmeRs (this lncRNA served as positive control for the GapmeR technology).

2.7 Functional Characterization of Candidate lncRNAs

2.7.1 Influence on cardiomyocyte size

Cardiomyocyte hypertrophy is an adaptive response on the cellular level to pressure or volume stress in the heart. In vitro hypertrophic growth can be induced by stimuli including phenylephrine (PE) and isoproterenol (ISO). Therefore, HL-1 cells were stimulated with both compounds and investigated cardiomyocyte cell size under altered lncRNA levels. Results are exemplary given for the lncRNA Gm17499 (FIG. 22).

Enhanced expression of lncRNA Gm17499 prevents cell size increase due to pro-hypertrophic stimuli, while its silencing resulted in an enlargement of cardiomyocytes, indicating an anti-hypertrophic function of this transcript.

2.7.2 Influence on Hypertrophy-Associated Genes

Hypertrophy-induced cardiomyocyte growth is accompanied by a reinduction of the "fetal gene program", because gene expression patterns mimic those seen during embryonic development. Applying the same conditions (stimulus and deregulation) regarding the candidate lncRNA Gm17499 expression levels of hypertrophy-associated genes including ANP, BNP (arterial and brain natriuretic peptide), and Mcip1.4 (modulatory calcineurin-interacting protein 1, exon 4 isoform) were measured (FIG. 23).

2.8. Conclusion

In conclusion, based on the above experimental findings the deregulated lncRNAs in the tested cardiac hypertrophy model (left ventricular pressure overload) are of diagnostic and therapeutic interest for cardiac hypertrophy. In particular, the following lncRNAs are of major importance:

TABLE 6

Summary of investigated lncRNAs candidates.

| Name | Identifier | Source | Size | relationship | related gene |
|---|---|---|---|---|---|
| Gm17499 | ENSMUST00000171177 | Ensembl | 692 bp | Antisense | Tmpo |
| Gm16192 | ENSMUST00000148357 | Ensembl | 937 bp | antisense | Mtus1 |
| Gm11641 | ENSMUST00000130556 | Ensembl | 923 bp | Antisense | — |
| Gm8459 | ENSMUST00000162504 | Ensembl | 760 bp | intergenic | — |
| AK083183 | AK083183.1 | Fantom3 | 2759 bp | intergenic | — |
| Gm13316 | ENSMUST00000140537 | Ensembl | 691 bp | antisense | Cacnb2 |
| H19 | ENSMUST00000136359 | Ensembl | 2286 bp | intergenic | — |
| (NR_001592.1) | ENSMUST00000152754 | Ensembl | 1853 bp | intergenic | — |
|  | ENSMUST00000140716 | Ensembl | 817 bp | Intergenic | — |
| AK013700 | AK013700.1 | predicted | 725 bp | intergenic | — |
| Gm15892-002 | ENSMUST00000152627 | Ensembl | 439 bp | intergenic | — |
| BC023483 | uc007dvi.1 | UCSC | 1726 bp | intergenic | — |
| Gm12224-001 | ENSMUST00000124047 | Ensembl | 567 bp | antisense | Acsl6 |
| AJ409495 | AJ409495.1 | NRED | 292 bp | intergenic | — |
| Gm8822-202 | ENSMUST00000168371 | Ensembl | 339 bp | intergenic | — |

TABLE 7

Human homologs of the the investigated lncRNAs candidates

| Mouse lncRNA | Identifier | human homolog | Identity to mouse sequence |
|---|---|---|---|
| Gm17499 | ENSMUST00000171177 | >gi\|568815586\|ref\|NC_000012.12\|: 98547558-98547816<br>*Homo sapiens* thymopoietin (TMPO), chromosome 12, GRCh38 Primary Assembly | 88.42% |
| Gm16192 | ENSMUST00000148357 | >gi\|17224595\|gb\|AF293357.1\|: 128-394<br>*Homo sapiens* AT2 receptor-interacting protein 1 mRNA, complete cds | 78.47% |
| Gm11641 |  | >gi\|568815581:64783259-64783551<br>*Homo sapiens* chromosome 17, GRCh38.p2/Primary Assembly | 69% |
| Gm8459 | ENSMUST00000162504 | >gi\|307219258\|ref\|NG_001223.5\|: 149-953<br>*Homo sapiens* voltage-dependent anion channel 1 pseudogene 2 (VDAC1P2) on chromosome X | 80.52% |
| AK083183 | AK083183.1 | >gi\|568815595\|ref\|NC_000003.12\|: 142958129-142958893<br>*Homo sapiens* chromosome 3, GRCh38 Primary Assembly | 69.10% |

TABLE 7-continued

Human homologs of the the investigated lncRNAs candidates

| Mouse lncRNA | Identifier | human homolog | Identity to mouse sequence |
|---|---|---|---|
| Gm13316 | ENSMUST00000140537 | >gi\|69122714\|ref\|NM_014409.3\|: 1241-1929<br>*Homo sapiens* TAF5-like RNA polymerase II, p300/CBP-associated factor (PCAF)-associated factor, 65 kDa (TAF5L), transcript variant 1, mRNA | 87.37% |
| H19 | NR_001592.1 | * >gi\|57862814\|ref\|NR_002196.1\|: 708-2305<br>*Homo sapiens* H19, imprinted maternally expressed transcript (non-protein coding) (H19), long non-coding RNA | 71.25% |
| AK01370 | AK013700.10 | >gi\|13899395\|gb\|AC008383.8\| AC008383:167188-167922<br>*Homo sapiens* chromosome 5 clone CTC-222022, complete sequence | 71.98% |
| Gm15892-002 | ENSMUST00000152627 | >gi\|21754306\|dbj\|AK095112.1\|: 3681-4000<br>*Homo sapiens* cDNA FLJ37793 fis, clone BRHIP3000473 | 80.00% |
| BC023483 | uc007dvi.1 | >gi\|568815597\|ref\|NC_000001.11\|: 245708650-245709375<br>*Homo sapiens* chromosome 1, GRCh38 Primary Assembly | 74.27% |
| Gm12224-001 | ENSMUST00000124047 | >gi\|568815593\|ref\|NC_000005.10\|: 131971540-131971671<br>*Homo sapiens* chromosome 5, GRCh38 Primary Assembly | 88.64% |
| AJ409495 | AJ409495.1 | >gi\|568815593\|ref\|NC_000005.10\|: 123761272-123761427 chromosome 5, GRCh38 Primary Assembly | 89.17% |
| Gm8822-202 | ENSMUST00000168371 | >gi\|27882035\|gb\|BC044590.1\|: 321-659<br>*Homo sapiens* ARP3 actin-related protein 3 homolog (yeast), mRNA (cDNA cloneMGC:57216 IMAGE:5261640), complete cds | 94.10% |

Example 3—Further Characterization of the Anti-Hypertrophic lncRNA H19

3.1. Differential Expression in 4 and 6 Week sham/TAC

To identify lncRNA candidates deregulated in whole heart samples 6 weeks after TAC (transverse aortic constriction) or in cardiomyocytes from mouse hearts 13 weeks after TAC general lncRNA profiling provided by Arraystar was performed (Arraystar Mouse LncRNA microarray V2.0). From this platform the lncRNA H19 (NR_001592.1) was identified as one of the potential candidates in addition to Gm17499 and Gm11641 (Tab. 8 and 9).

TABLE 8

H19 lncRNA derived from Arraystar Mouse LncRNA microarray V2.0 analyzing whole heart samples from 6 week sham and TAC mice.

| Name | Identifier | Source | Size | relationship | FC | Regulation |
|---|---|---|---|---|---|---|
| H19 | ENSMUST00000136359 | Ensembl | 2286 bp | intergenic | −2, 01 | Down |
| (NR_001592.1) | ENSMUST00000152754 | Ensembl | 1853 bp | intergenic | −2, 06 | Down |
|  | ENSMUST00000140716 | Ensembl | 817 bp | intergenic | −5, 30 | Down |

TABLE 9

H19 lncRNA derived from Arraystar Mouse LncRNA microarray V2.0 analyzing a cardiomyocyte-specific fraction of 12 week healthy vs. 13 week TAC mouse hearts.

| Name | Identifier | Source | Size | relationship | FC | Regulation |
|---|---|---|---|---|---|---|
| H19 | ENSMUST00000140716 | Ensembl | 817 bp | intergenic | −4, 73 | Down |
| (NR_001592.1) | ENSMUST00000136359 | Ensembl | 2286 bp | intergenic | −2, 48 | Down |

Figure 15A:
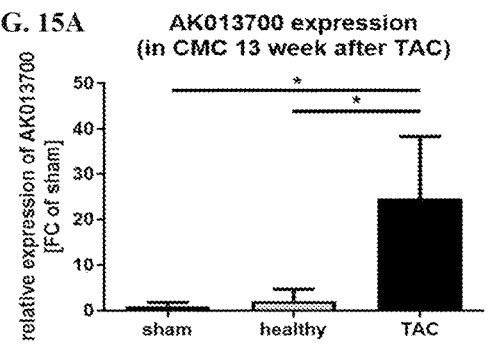
FIG. 15A-J FIG. 15A-FIG. 15H Validation of candidate lncRNAs derived Arraystar Mouse LncRNA microarray V2.0 comparing a cardiomyocyte (CMC) samples from 12 week healthy or 13 week sham vs. 13 week TAC mouse hearts. Candidate AJ409495 is potentially protein coding and will not be considered in the following presentation of the results. FC—fold change. CMC—cardiomyocytes. *p<0.001, p<0.01, *p<0.05, n.s.=not significant.
Figure 15B:
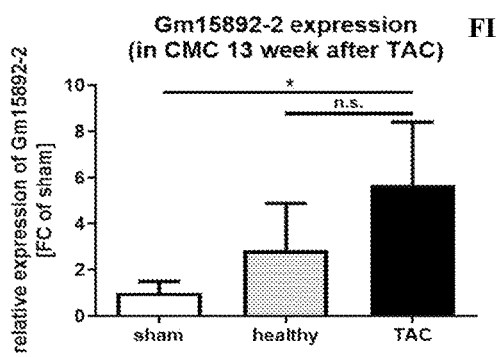
Figure 24A:
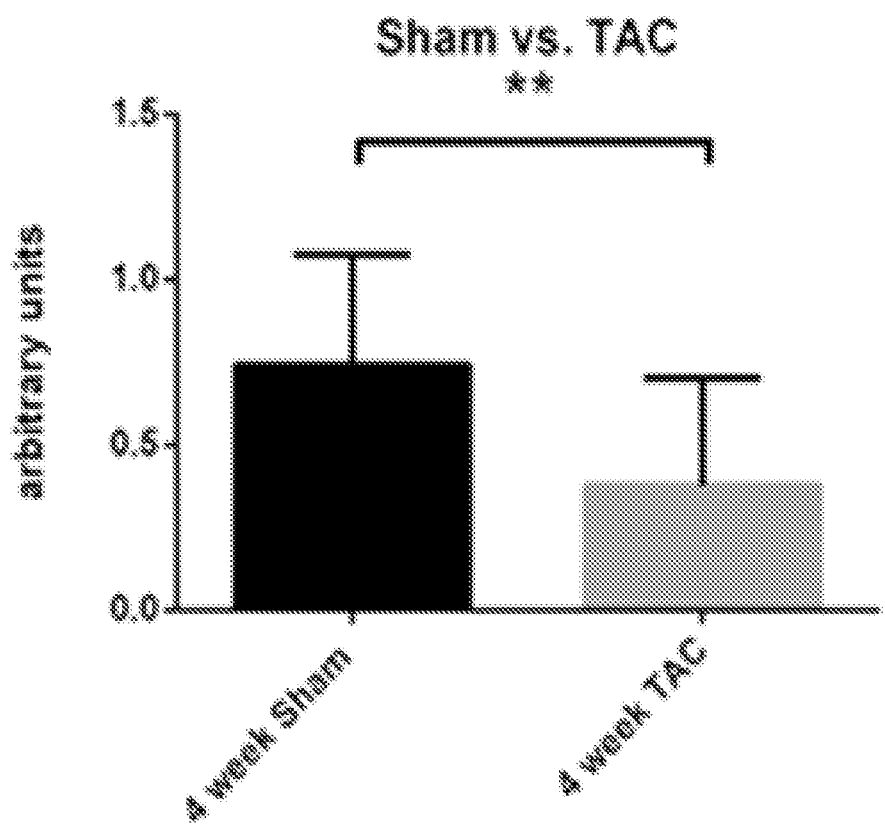
FIG. 24A-B: Validation of candidate lncRNA H19 expression 4 and 6 weeks after TAC operation. **p<0.001, *p<0.05. n=5×7.
Figure 24B:
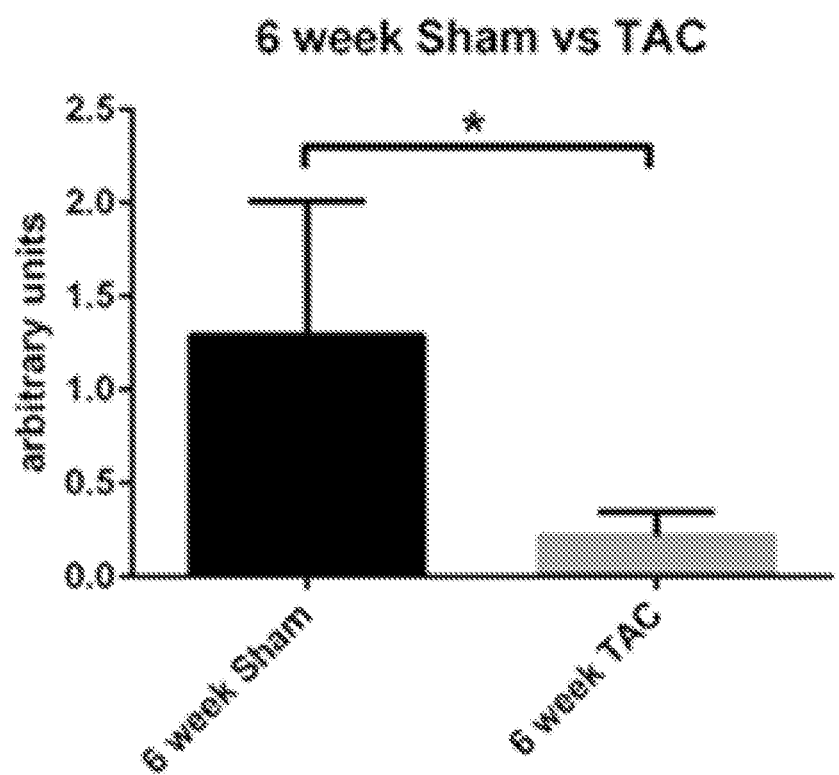

The downregulation of candidate lncRNA H19 four and six weeks after TAC surgery was validated by real-time PCR (RT-PCR) (FIGS. 24A and B; validation of the cardiomyocyte-specific array is shown above (Table 8 and FIGS. 15A and B). The repression of H19 was verified in whole heart samples 6 weeks after TAC operation. In addition, this repression was observed in earlier as well as later stages of hypertrophy and heart failure (FIG. 15B). The validation of the CMC-specific array revealed, that this repression can be found in cardiomyocytes (FIG. 15A), suggesting that H19 might be involved in the development of cardiac hypertrophy and modulation of H19 levels is of therapeutical value.

Figure 15C:
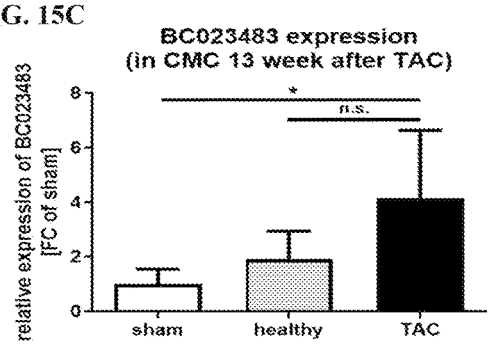
Figure 15D:
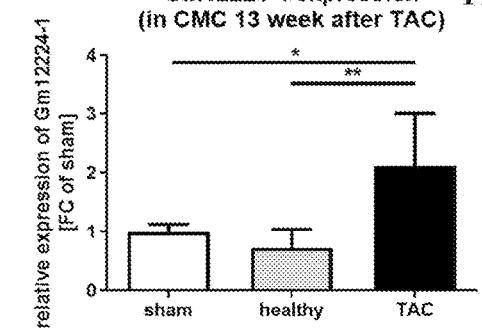
Figure 15E:
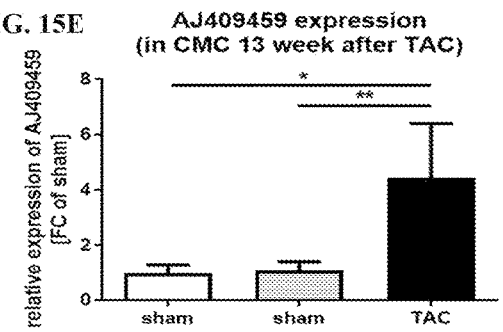
Figure 15F:
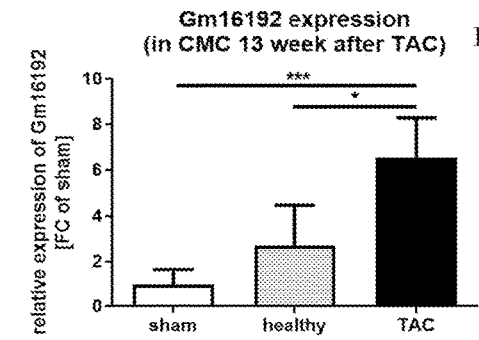
Figure 15G:
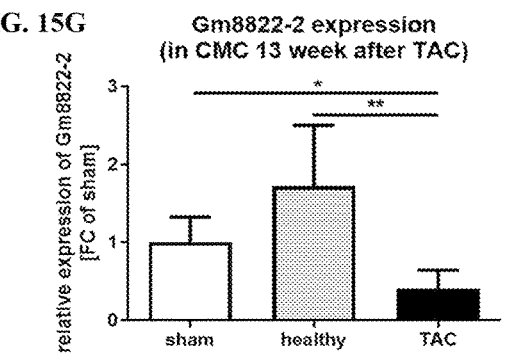
Figure 15H:
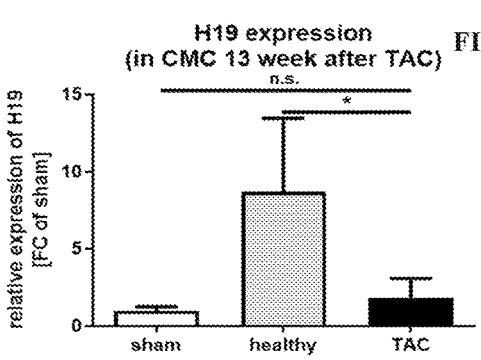
Figure 15I:
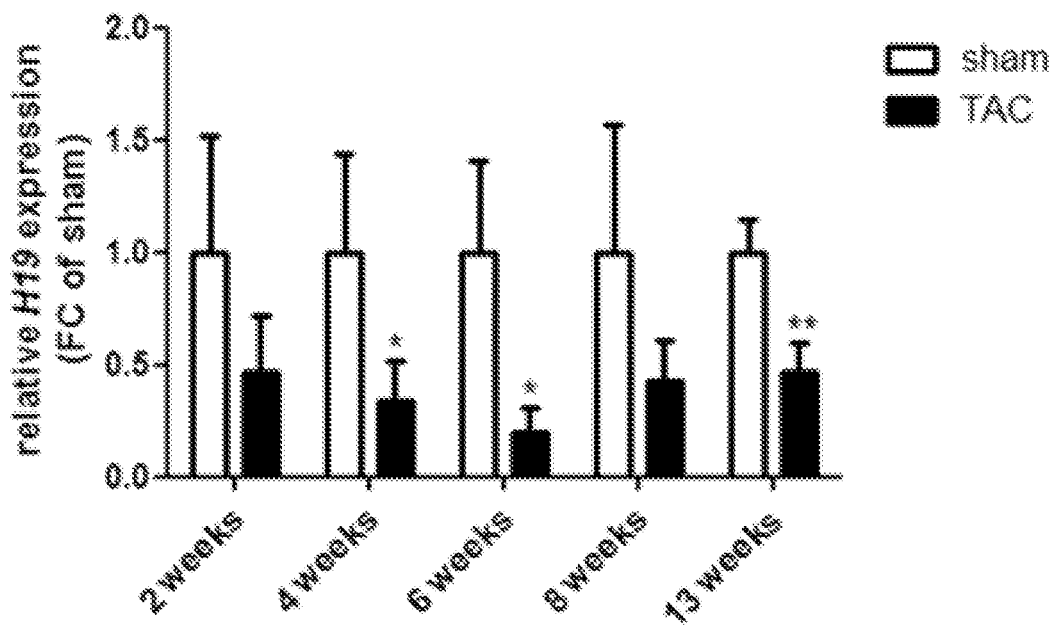
Figure 15J:
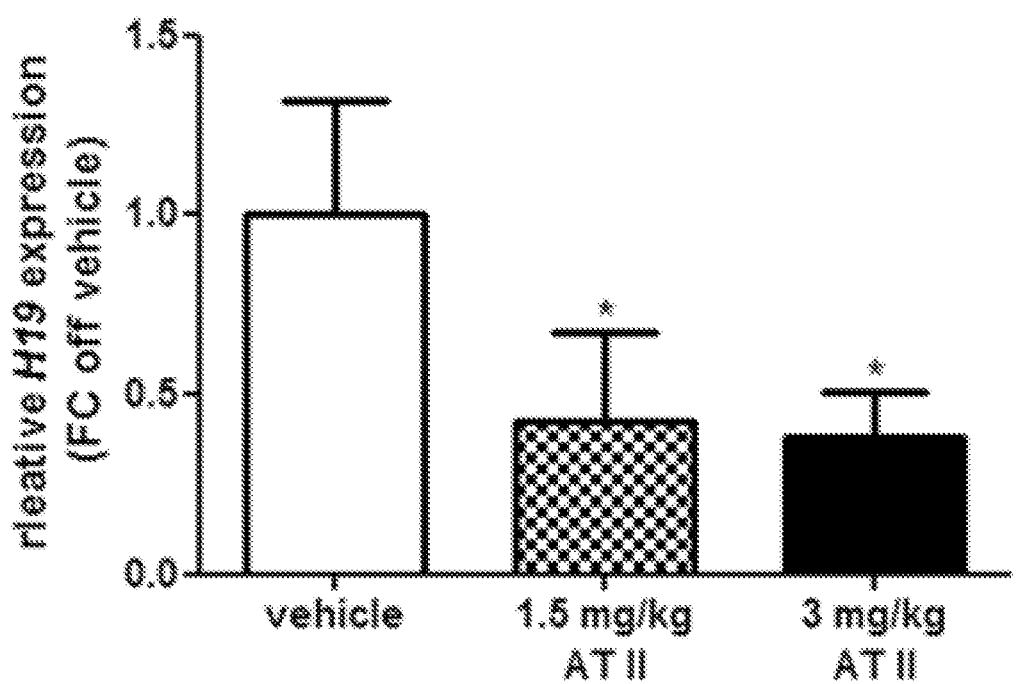
Figure 16G:
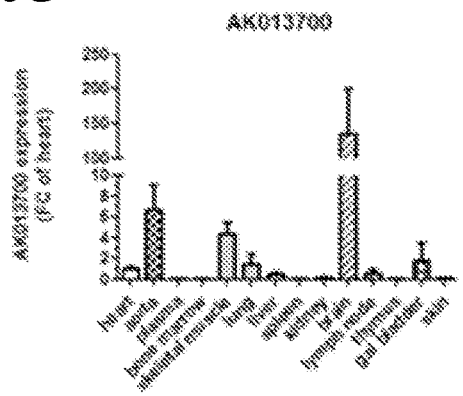
Figure 16H:
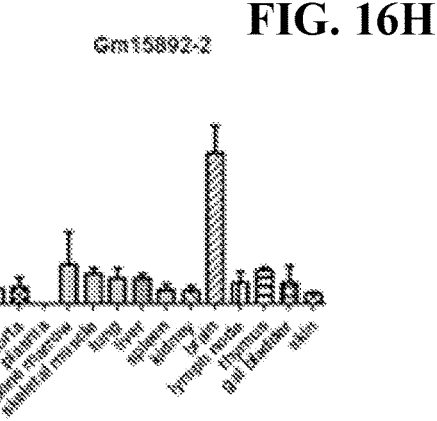
Figure 16I:
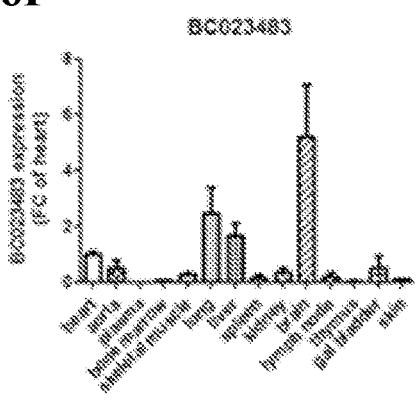
Figure 16J:
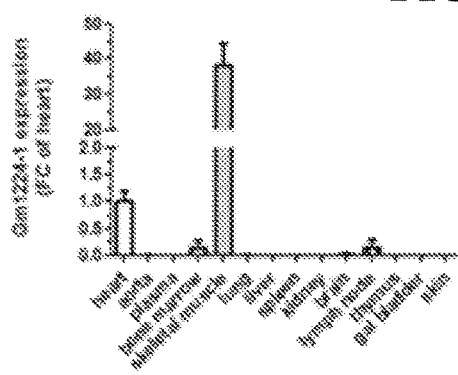
Figure 16K:
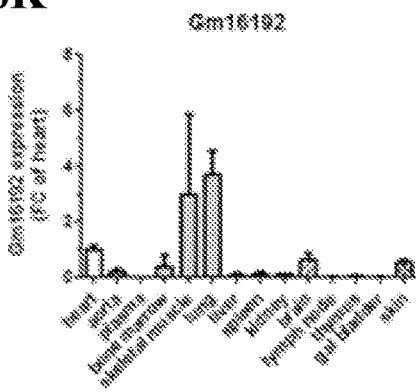
Figure 16L:
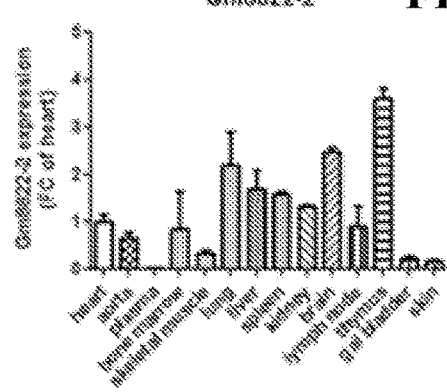
Figure 17A:
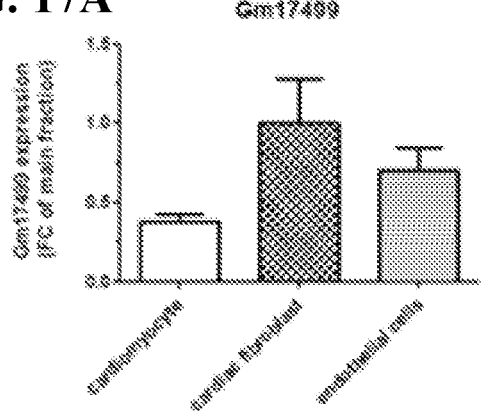
FIG. 17A-K: Expression of candidate lncRNAs in cardiomyocytes, cardiac fibroblasts and endothelial cells derived from mouse hearts. FC—fold change.
Figure 17B:
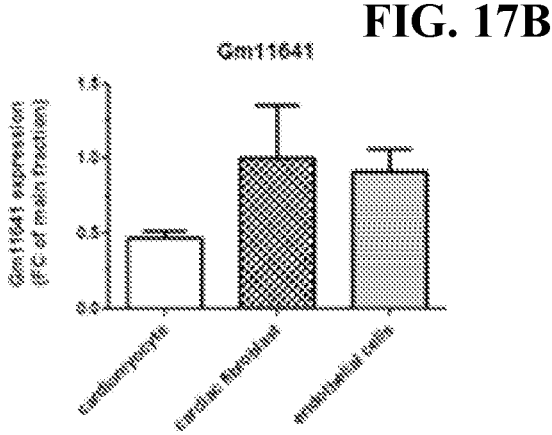
Figure 17C:
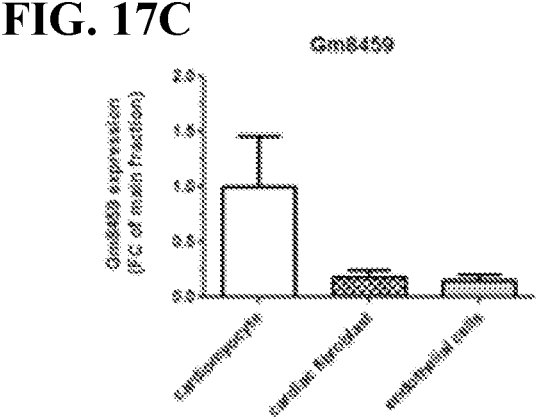
Figure 17D:
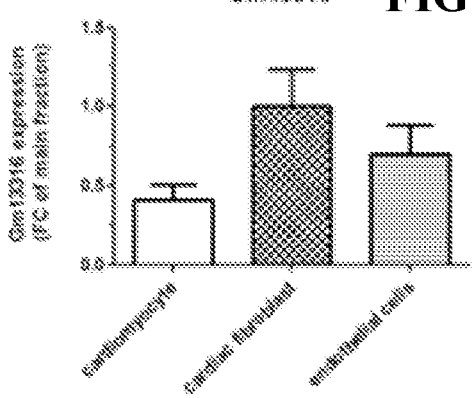
Figure 17E:
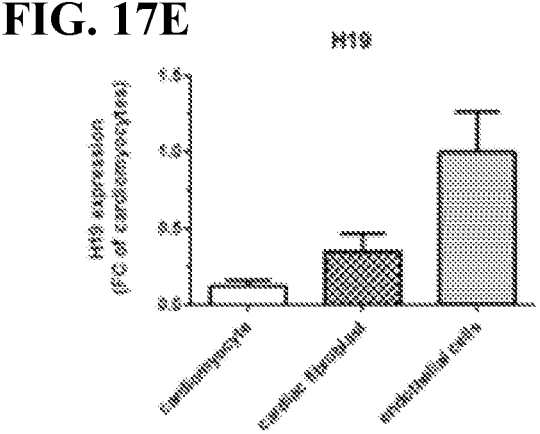
Figure 17F:
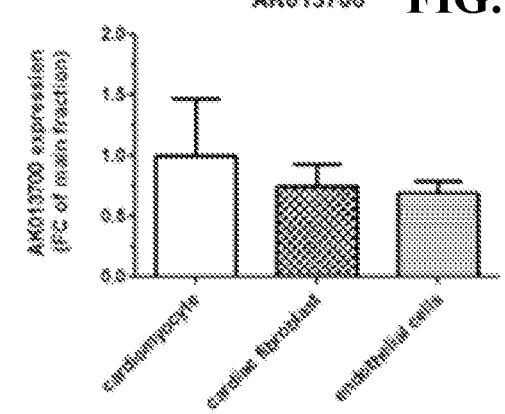
Figure 17G:
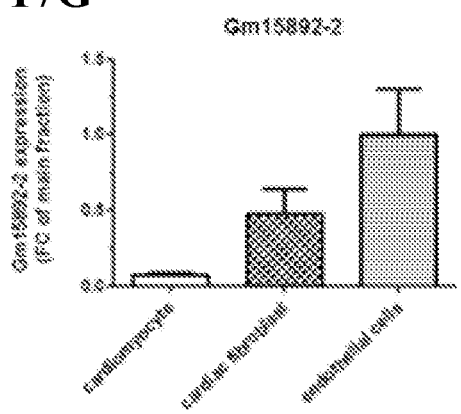
Figure 17H:
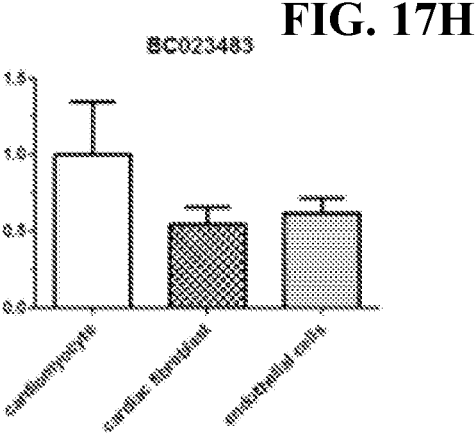
Figure 17I:
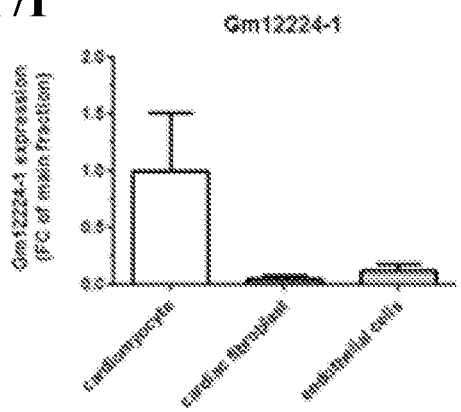
Figure 17J:
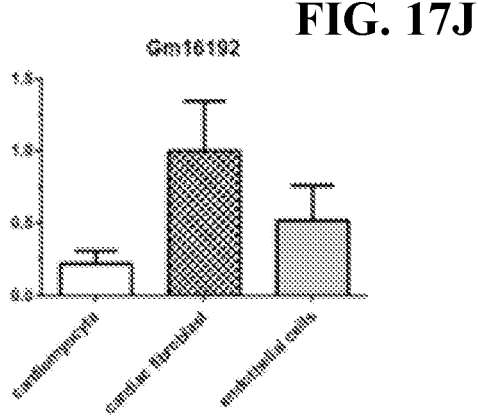
Figure 17K:
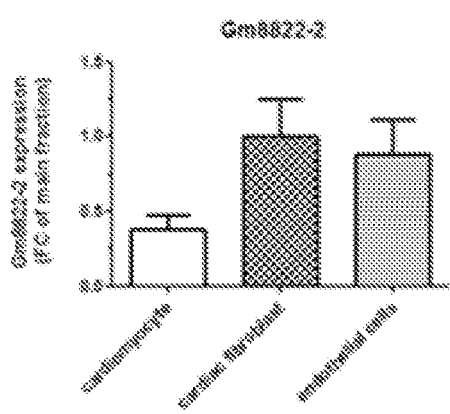

A second model of cardiac hypertrophy is the continuous infusion of angiotensin II (ATII). This compound is a central product of the renin-angiotensin system and causes an increase in blood pressure via its vasoconstrictive effect. Clinical studies on the effect of angiotensin-converting enzyme (ACE) inhibitors revealed that ATII plays also a central role in the pathophyiology of cardiac hypertrophy, remodeling and heart failure. To induce cardiac hypertrophy, osmotic minipumps (Alzet pumps) are implanted subcutaneously into mice for 2 weeks. In this model, the same reduction of H19 levels was observed as for the TAC model, underlining the relevance of this lncRNA in cardiac hypertrophy (FIG. 15C).

3.2 Organ Expression of Candidate lncRNA H19

To determine the abundance and tissue specific expression of lncRNA H19 in different organs (FIG. 16), its expression was measured in 14 different tissue samples including heart, aorta, plasma, bone marrow, skeletal muscle, lung, liver, spleen, kidney, brain, lymph node, thymus, gall bladder, and skin. H19 shows a strong enrichment in muscle tissue, including heart, skeletal muscle, and gal bladder.

3.3 Expression of Candidate lncRNA H19 in Cellular Fractions of the Heart

The expression profile of lncRNA H19 was examined in the three main cell types of the heart: cardiomyocytes, cardiac fibroblasts and endothelial cells. Therefore, adult mouse heart cells were isolated from several individual hearts applying retrograde perfusion and enzymatic dissociation protocols and determined the levels of lncRNA candidates in each fraction. H19 was found to be expressed in all cardiac cell types (FIG. 17).

3.4 Subcellular Localization of Candidate lncRNA H19

The biological function of lncRNAs is strongly determined by their subcellular localization. Therefore, a biochemical separation of the total RNA derived from HL-1 cells (a mouse cardiomyocyte cell line) into cytoplasmatic, nuclear-soluble and chromatin-associated fraction was performed (according to: Cabianca et al Cell. 11; 149(4):819-31.). The relative abundance of lncRNA H19 in the different fractions was measured by quantitative RT-PCR. The known housekeeping genes GAPDH and β-Actin as well as the lncRNAs Xist and Neat1 were used as controls for cytoplasmatic localization or chromatin-bound enrichment, respectively. H19 is found in all subcellular fractions, the cytosol, nuclear soluble and chromatin associated compartments of cardiomyocytes (FIG. 18). This indicates that H19 has the possibility to modulate both transcriptional and post-transcriptional processes.

3.5 Repression of Candidate lncRNA H19

To downregulate H19 lncRNA an antisense chemistry named esiRNA was applied. EsiRNAs (Eupheria Biotech/Sigma-Aldrich) are endoribonuclease-prepared siRNAs resulting from cleavage of long double-stranded RNAs. This antisense species targets not only one specific sequence as it is the case for siRNAs, but several sequences all over the target.

Figure 26A:
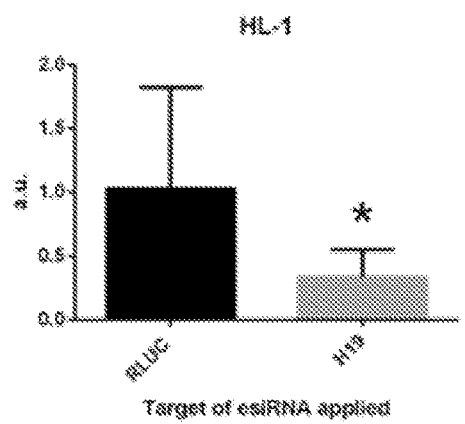
FIG. 26A-D.
Figure 26B:
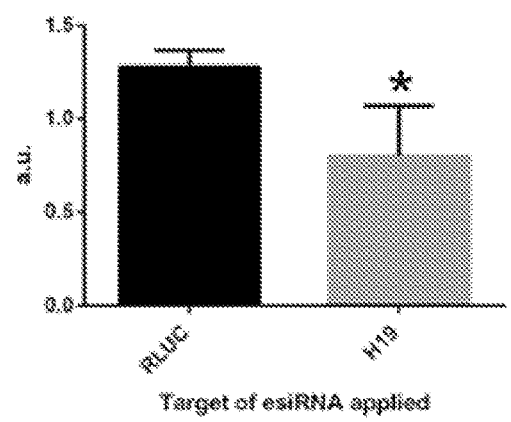

Compared to a control transfection (RLUC, renilla luciferase), lncRNA H19 was significantly downregulated in two different cardiomyocyte cell lines derived from mouse (HL-1) and rat (H9C2) (FIGS. 26A and B).

Figure 26C:
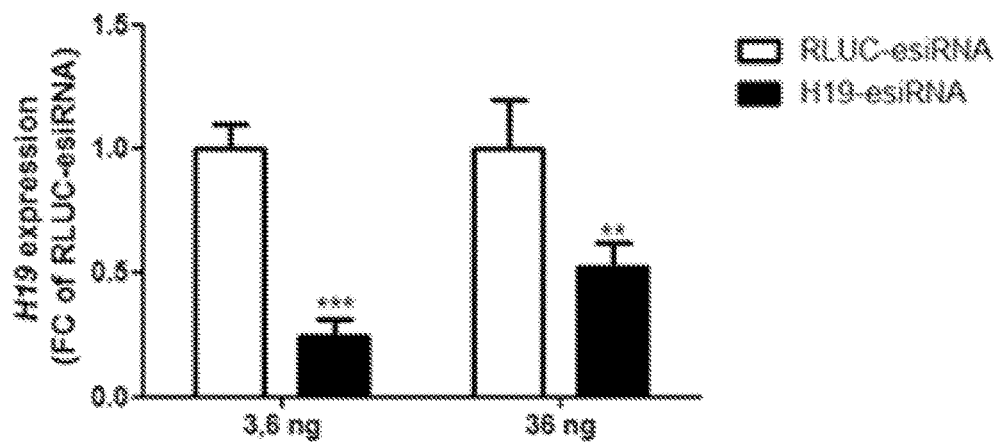
Figure 26D:
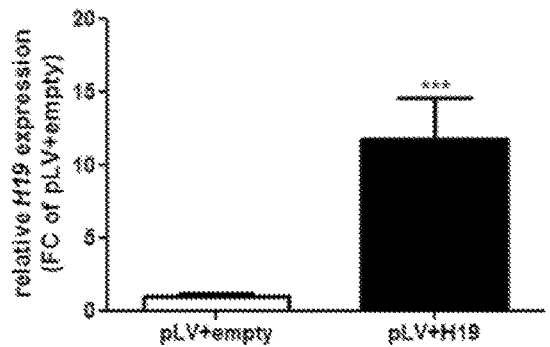

To stably overexpress this transcript, the full length transcript was cloned into the multiple cloning site (MCS) of a lentiviral overexpression vector. This plasmid harbours a bidirectional promoter that allows the production of the lncRNA transcript from the same gene regulatory element, but physically decoupled from the indicator gene GFP (green fluorescent protein) and a selection cassette. By lentiviral transduction the construct was introduced into HL-1 cardiomyocytes. Lentivirus-mediated transduction of HL-1 cells showed a stable overexpression of H19 compared to cells harbouring the control vector (pLV+empty) (FIG. 26C).

3.6 Functional Characterization of lncRNA H19

3.6.1 In Vitro Effect of Hypertrophied Cardiomyocytes on H19 Levels

Figure 25:
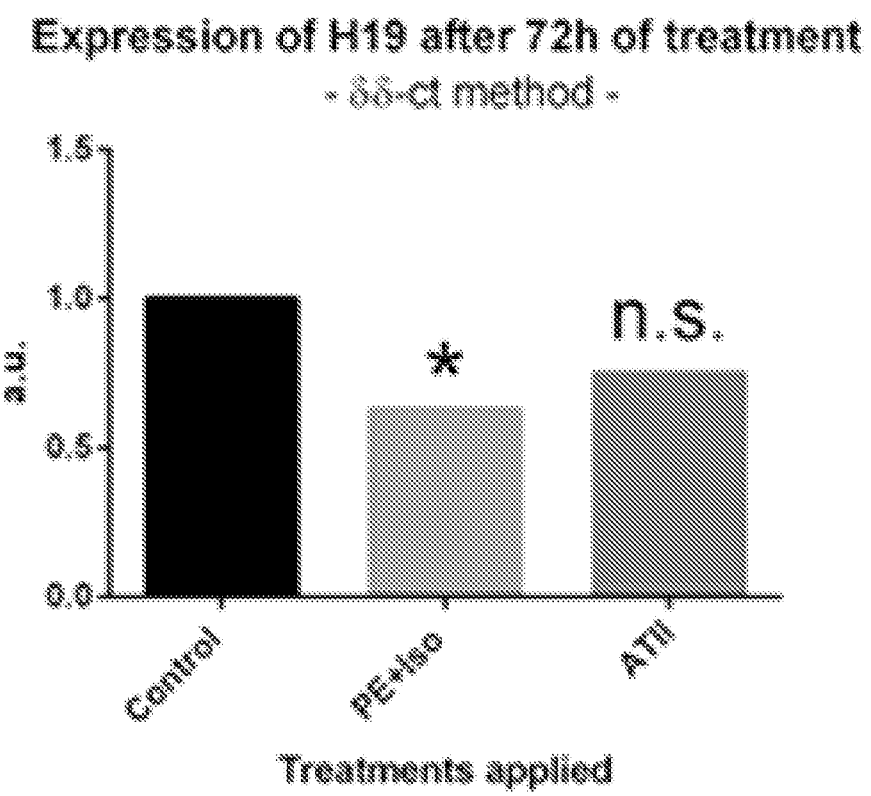
FIG. 25: LncRNA H19 expression in primary neonatal rat cardiomyocytes (NRCM) after 72 h treatment with pro-hypertrophic phenylephrine (PE) and isoproterenol (ISO) or Angiotensin II (ATII). n.s.—not significant. *p<0.05.

Cardiomyocyte hypertrophy is an adaptive response on the cellular level to pressure or volume stress in the heart. In vitro hypertrophic growth can be induced by stimuli including phenylephrine (PE) and isoproterenol (ISO) or Angiontensin II (ATII). Therefore, HL-1 cells were stimulated with these compounds and investigated their influence on the expression of H19 (FIG. 25).

3.6.2 Influence of H19 Repression on Cardiomyocyte Size

Figure 27A:
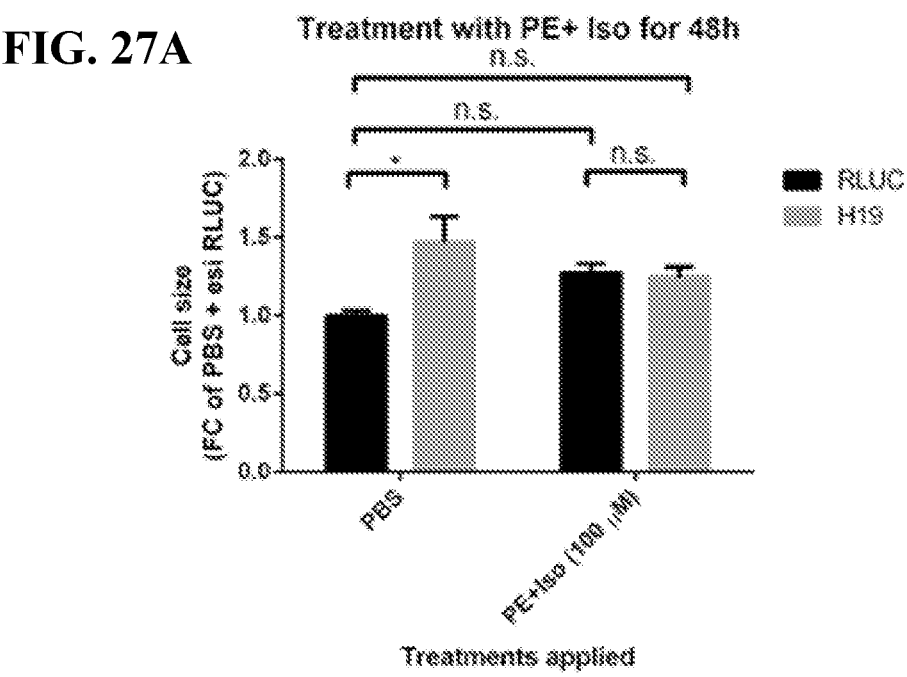
FIG. 27A-E.
Figure 27B:
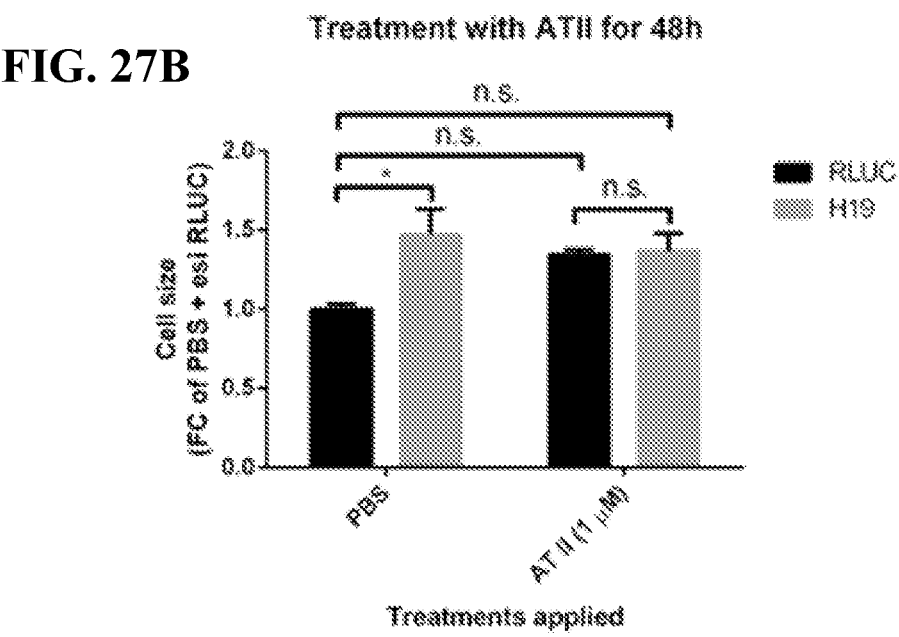
Figure 27C:
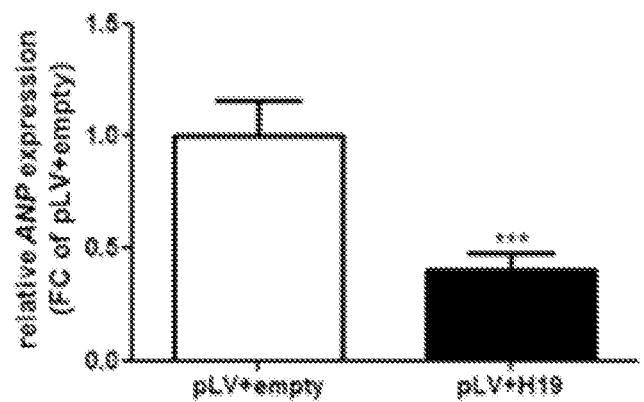
Figure 27D:
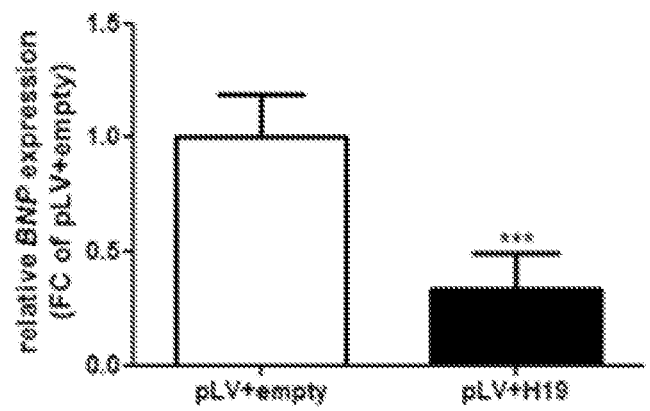
Figure 27E:
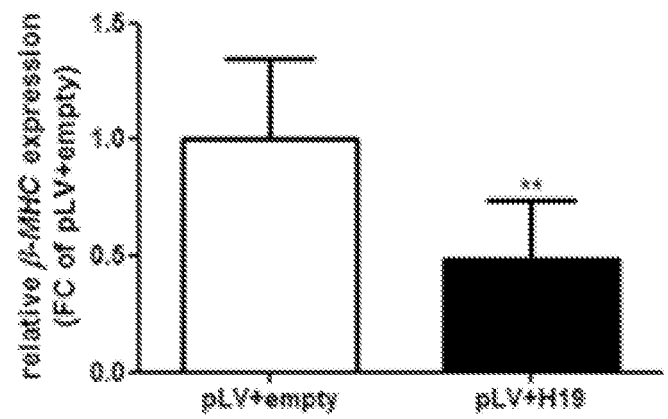
Figure 28A:
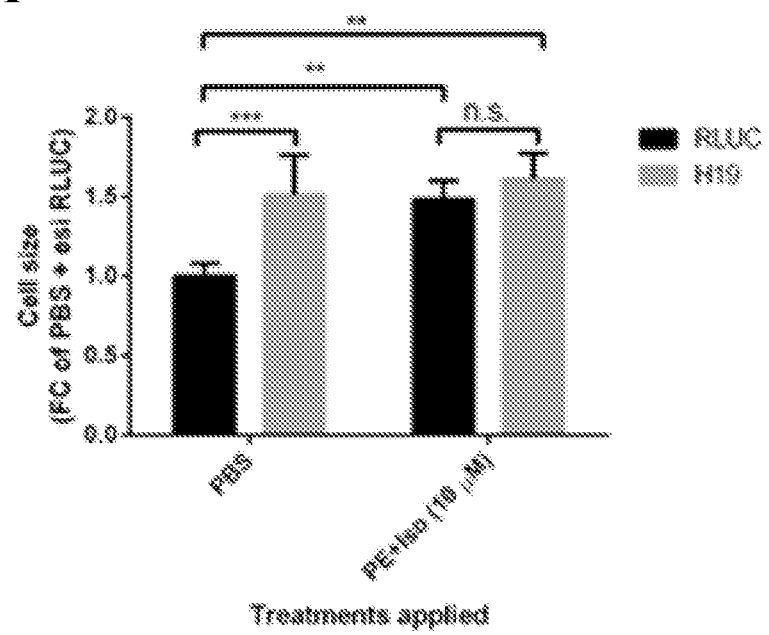
FIG. 28A-B: Cell size of rat cardiomyocyte cell line H9C2 repressing H19 (by esiRNA) treated with the hypertrophic stimuli phenylephrine (PE) and isoproterenol (ISO) FIG. 28A or Angiotensin II (ATII) FIG. 28B for 48 h. RLUC—esiRNA against renilla luciferase (negative control), H19—esiRNA against H19. *p<0.001, p<0.01. n.s.—not significant.
Figure 28B:
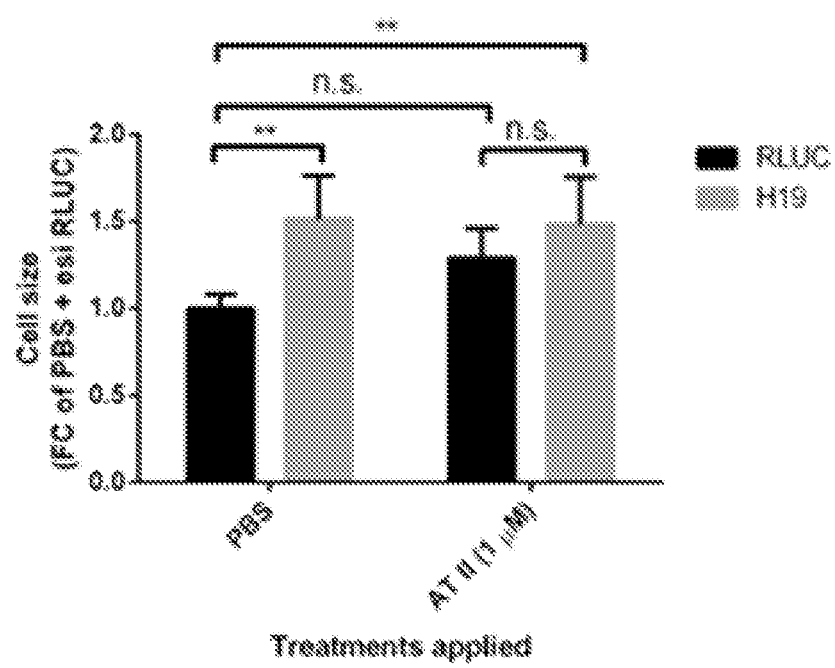
Figure 29A:
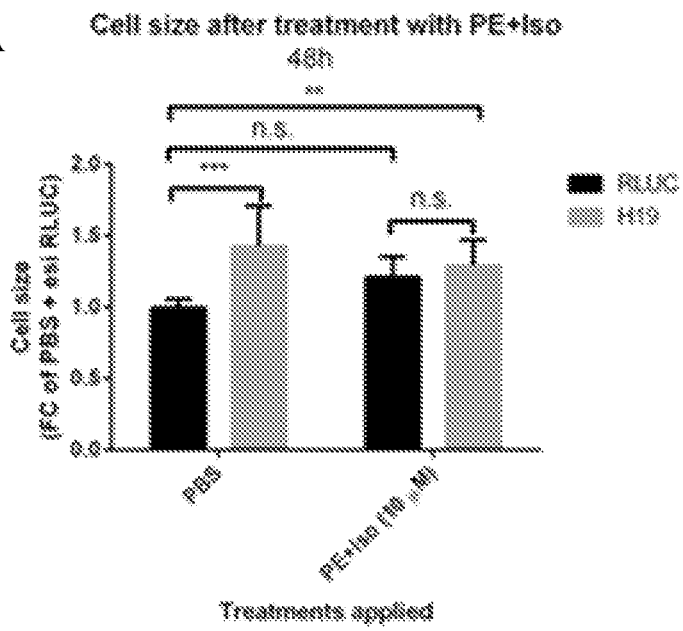
FIG. 29A-B: Cell size of primary neonatal rat cardiomyocytes (NRCM) repressing H19 (by esiRNA) treated with the hypertrophic stimuli FIG. 29A phenylephrine (PE) and isoproterenol (ISO) or FIG. 29B Angiotensin II (ATII) for 48 h. RLUC—esiRNA against renilla luciferase (negative control), H19—esiRNA against H19. *p<0.001, p<0.01. n.s.—not significant.
Figure 29B:
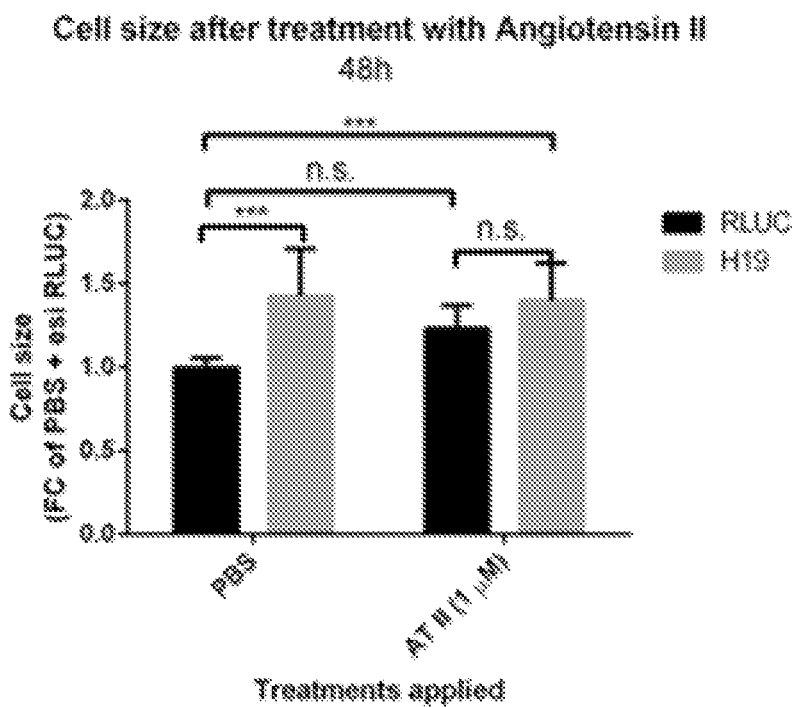
Figure 30A:
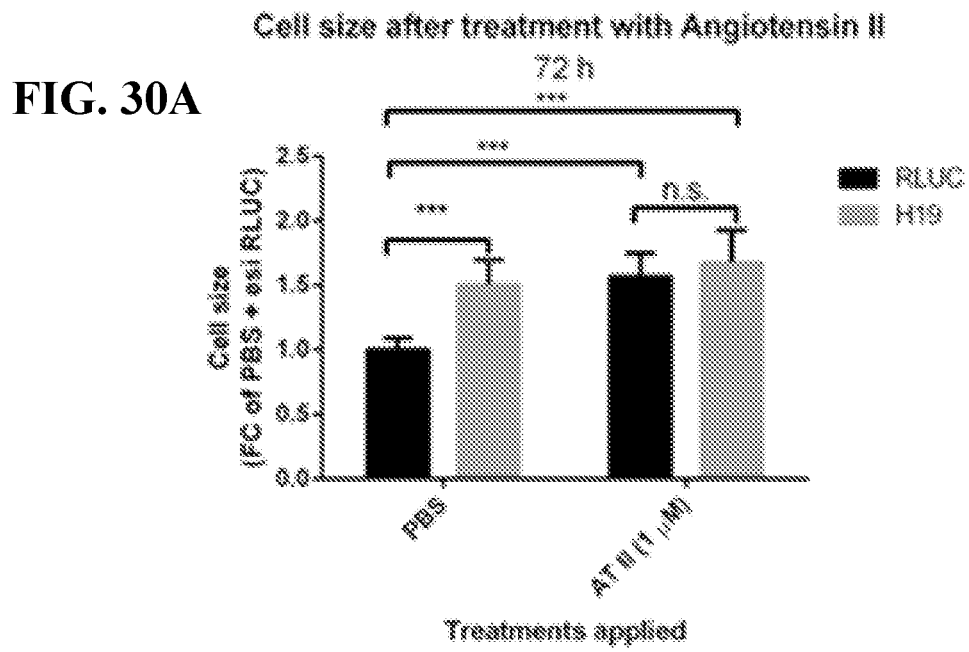
FIG. 30A-B: Cell size of primary neonatal rat cardiomyocytes (NRCM) repressing H19 (by esiRNA) treated with the hypertrophic stimuli FIG. 30A phenylephrine (PE) and isoproterenol (ISO) or FIG. 30B Angiotensin II (ATII) for 72 h. RLUC—esiRNA against renilla luciferase (negative control), H19—esiRNA against H19. ***p<0.001. n.s.—not significant.
Figure 30B:
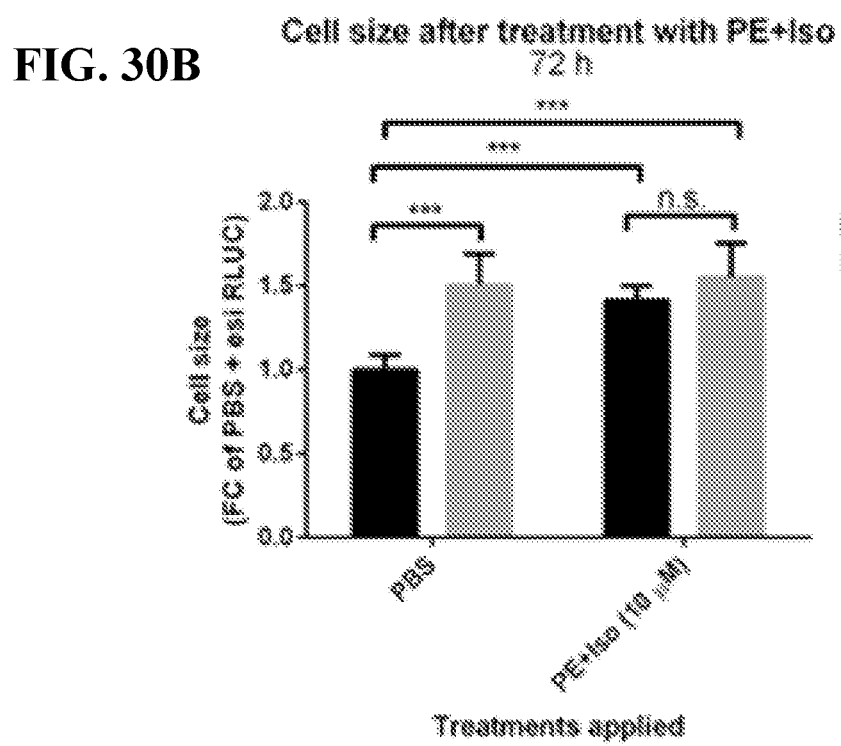

The hallmark of hypertrophied cardiomyocytes is an increase in cell size, relative to non-hypertrophic cells. Therefore, the cell size of cardiomyocytes was investigated after stimulation with PE and ISO or ATII while repressing H19 with esiRNA. The knockdown of H19 resulted in a significant increase in cardiomyocyte size in rat H9C2 cell line after 48 h as well as in neonatal rat cardiomyocytes (NRCMs) after 72 h (FIG. 28 to 30). This effect was observed after treatment with PE and ISO in both rat cardiomyocyte cell line as well as in NRCMs after AT II treatment. In the HL-1 cell line a comparable trend was observed (FIG. 27A).

Moreover, H19 was overexpressed in HL-1 cells. Overexpression of H19 in HL-1 cardiomyocytes led to a decrease of cardiac stress markers atrial and brain natriuretic peptide (ANP, BNP) and reduced levels of β-MHC (β-myosin heavy chain), another prominent marker of cardiac hypertrophy (FIG. 27A), further proving that induction of H19 has a cardioprotective effect.

3.7 Analysis of H19 Expression in Healthy and Diseased Human Heart Tissues

Figure 31:
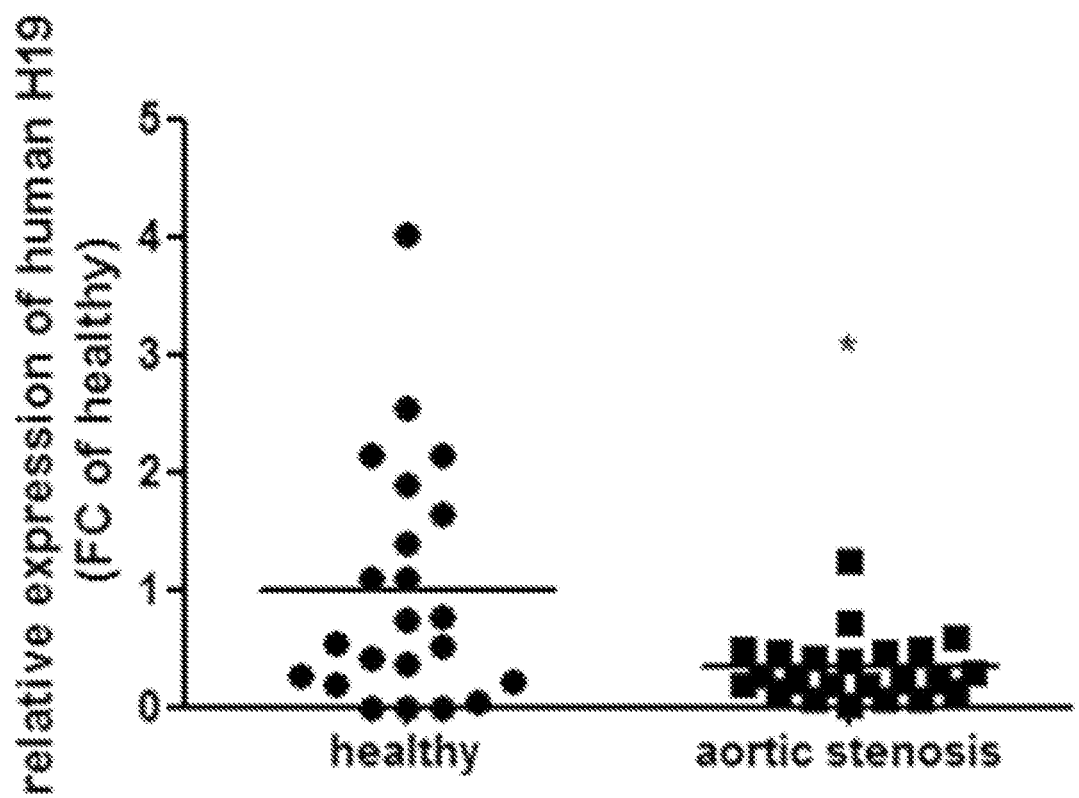
FIG. 31: H19 expression analysis in human healthy (n=22) and hypertrophic (aortic stenosis; n=23) heart tissues by real time PCR (RT-PCR). AS: aortic stenosis. **p<0.01

Aortic stenosis refers to calcification of aortic valve, which inhibits flow of blood. As a result heart needs to pump blood at a high pressure, finally leading to hypertrophic growth of the heart muscle. H19 expression was measured in 22 healthy heart tissues and 23 hypertrophic (aortic stenosis) heart tissues and found that H19 expression is strongly reduced in hypertrophic hearts (FIG. 31). This data from human subjects corroborates the findings described herein in mouse and rat in vitro models, and further evidences that H19 is a bona fide therapeutic target to prevent cardiac hypertrophy.

3.8. Evolutionary Conservation of H19

Figure 32:
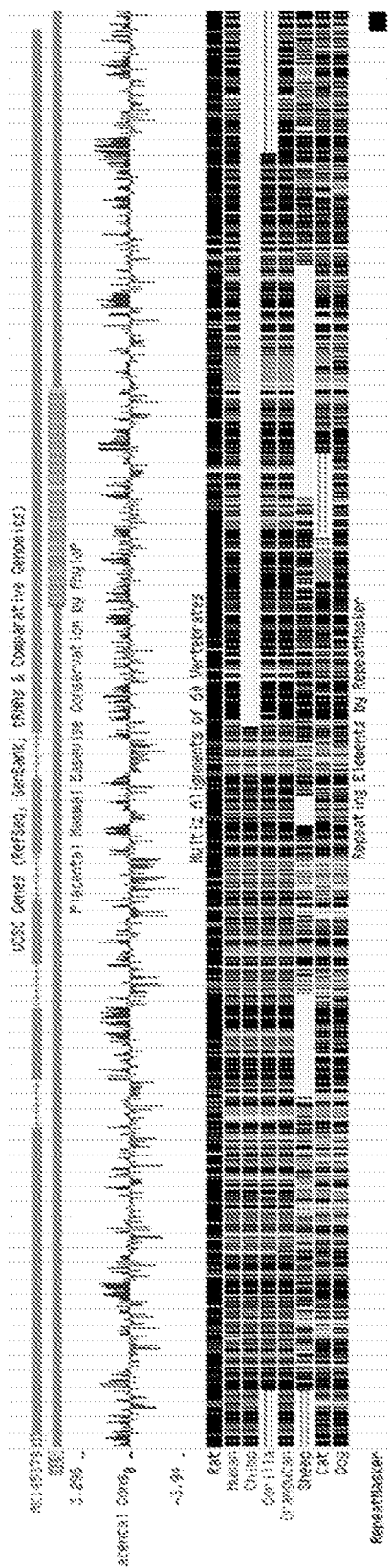
FIG. 32: Representation of conservation of the H19 sequence in different species applying the UCSC genome browser.
Figure 33A:
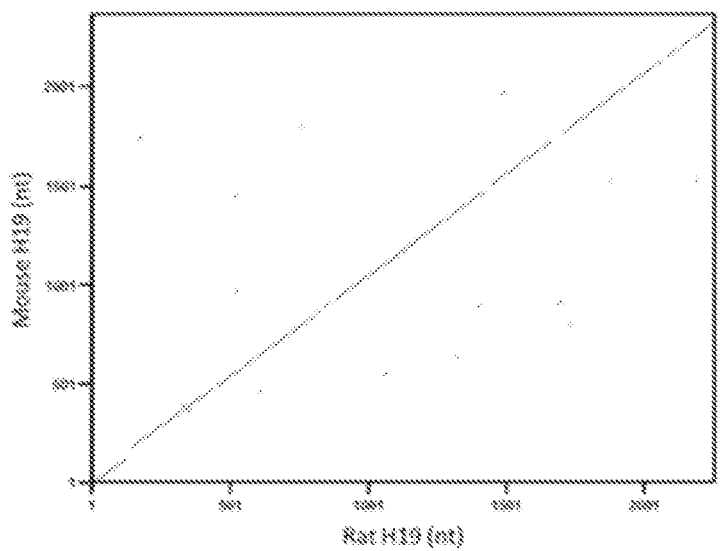
FIG. 33A-C: Sequence comparison of H19 sequences by Dotplot analysis. A strong conservation among mouse and rat, as well as mouse and humans can be observed. A homolog also exists in pig.
Figure 33B:
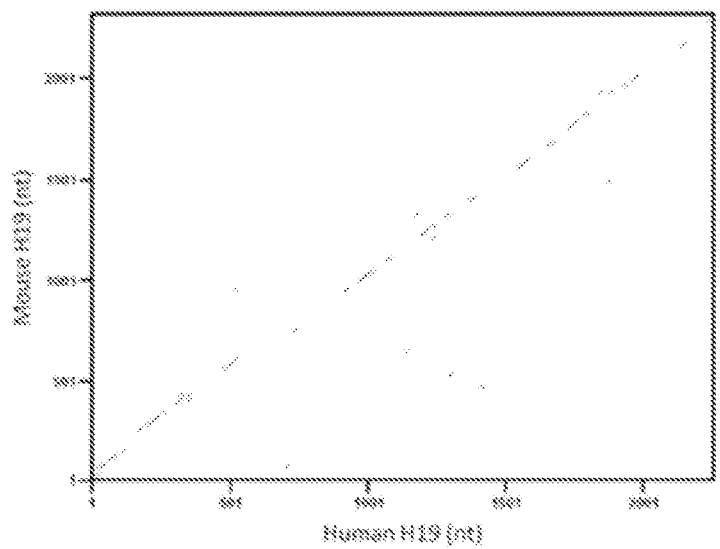
Figure 33C:
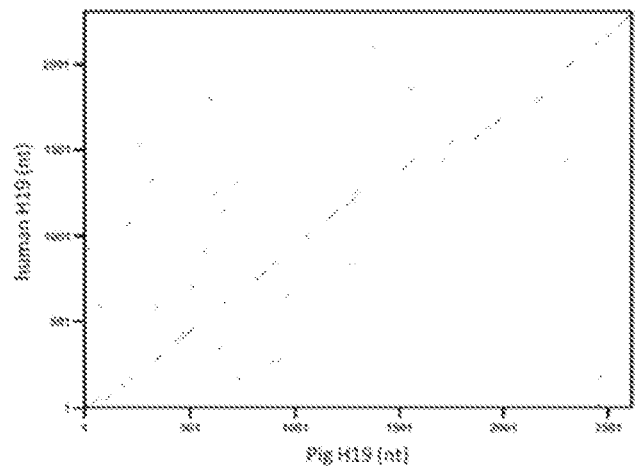

Several studies have shown that the H19 sequence as well the H19-imprinting mechanism are highly conserved among humans and rodents. This can be also depicted applying the UCSC genome browser (FIG. 32). A more detailed alignment of various H19 sequence by Dotplot analysis underlines these findings (FIG. 33) and shows a strong sequential relation between the murine and rat sequence, as well as the murine and human sequence. A further comparison revealed that the human H19 exhibits a homolog in pigs, enabling the performance of H19-related therapy strategies in large animal models.

3.9 In Vivo Studies on H19

To study the effects of H19 on cardiac remodeling in vivo a H19 knockout mouse was investigated. The deletion of H19 was achieved by neomycin resistance cassette that replaced the promoter and the entire 3 kb transcription unit of H19 (strain description: H19$^{tm1Lda}$ in a 129S2/SvPas background).

Figure 34:
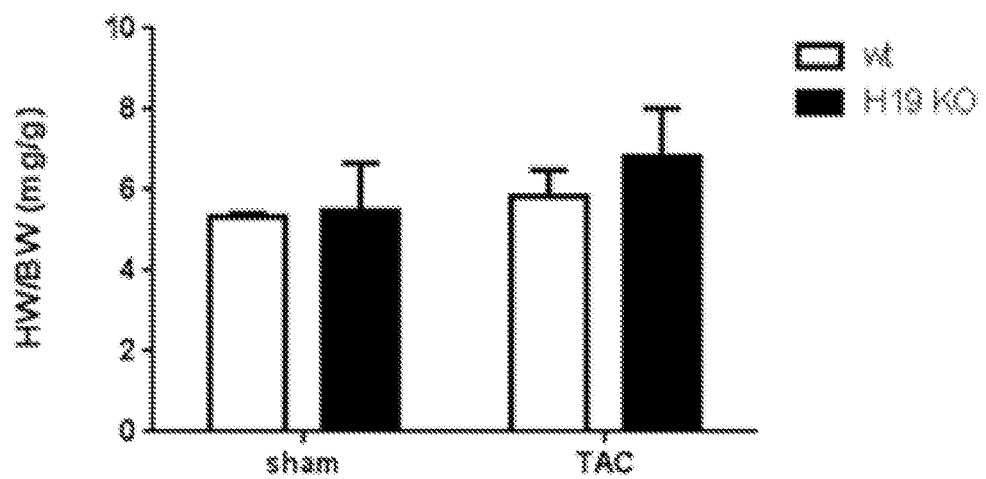
FIG. 34: TAC operation in H19 knockout mice and their wt littermates. After 6 weeks an induction of the heart-to-body-weight ratio was observed. n=2×8. HW=heart weight, BW=body weight, Wt=wild type.

The H19 knockout animals and their wildtype littermates (wt) were subjected to transverse aortic constriction (FIG. 34). As expected, after 6 weeks post surgery the wt showed an induction and heart-to-body-weight ratio. This gain of heart mass was also observed for sham mice comparing wt and H19 knockout animals, while TAC-operated mice lacking the H19 gene showed an exacerbated phenotype.

Figure 35A:
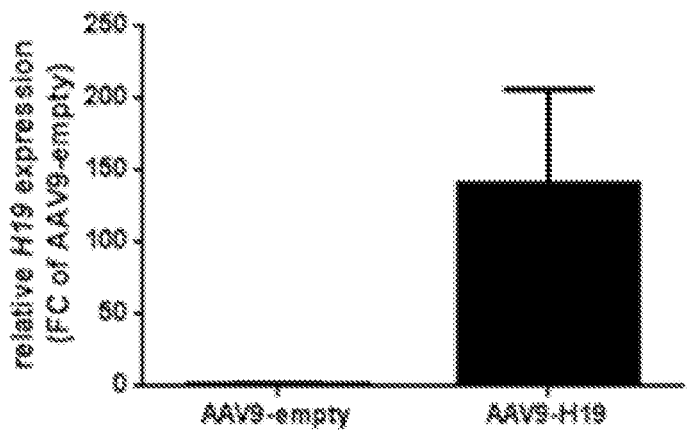
FIG. 35A-C: Overexpression by AAV9-H19 in vivo for 6 weeks leads to a reversion of the hypertrophic gene program (2+E12 copies per animal). n=3. *p<0.05. FC=fold change.
Figure 35B:
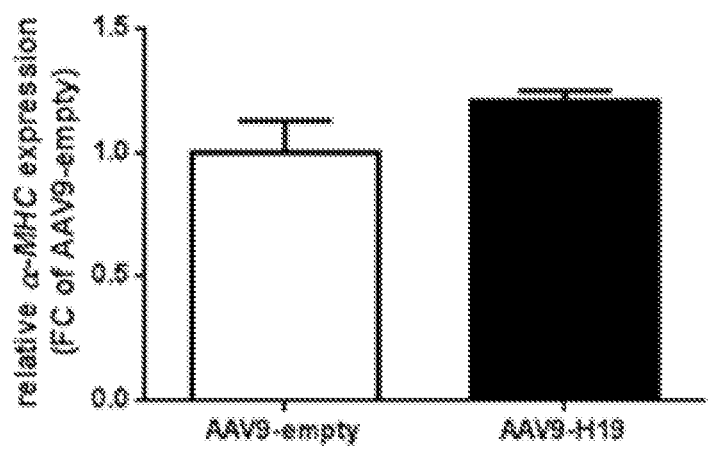
Figure 35C:
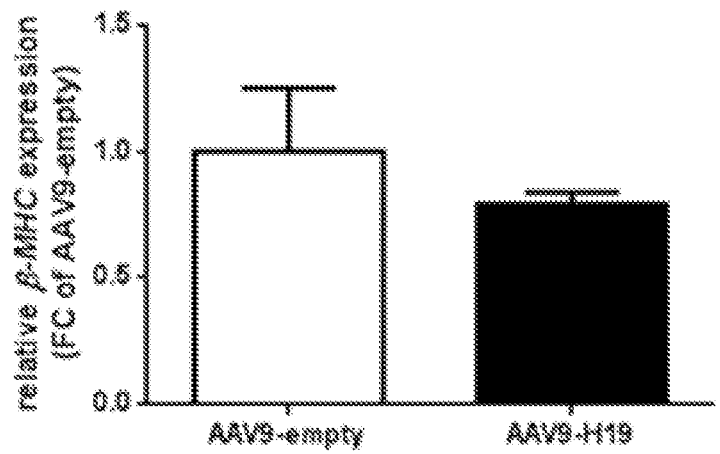

To get a more detailed analysis of the role of H19 in cardiac hypertrophy and to develop a potential therapeutic strategy, this transcript was overexpressed applying adenoviral vectors (AAV). An AAV9 was applied under the control of the cardiac-specific troponin T promoter to achieve an induction of H19 directed to cardiomyocytes (FIG. 35).

Applying the AAV9-H19 construct, a 150-fold induction of H19 was achieved in whole heart samples. Changes on transcriptional level of specific markers of cardiac hypertrophy were analyzed. Among them are the transcripts α-MHC, which is down-regulated in cardiac hypertrophy, and β-MHC, which is up-regulated. By in vivo overexpression of H19, a reversion of the α-MHC-to-β-MHC switch was observed (FIG. 35), indicating that adenoviral administration of H19 has a beneficial effect on the hypertrophic gene program and serves as a therapeutic strategy.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

---

The invention claimed is:

1. A method for treating a human subject having pathological ventricular cardiac hypertrophy comprising administering to the subject a compound promoting expression and/or activity of a lncRNA of SEQ ID NO: 12, wherein the compound is
   (a) a nucleic acid sequence which comprises or consists of the nucleic acid sequence of the lncRNA of SEQ ID NO: 12 or a nucleic acid sequence having at least 99% sequence identity over the entire length of SEQ ID NO: 12,
   (b) an expression vector expressing the nucleic acid sequence of (a), or
   (c) a host comprising the expression vector of (b).

2. The method of claim 1, wherein the expression of the nucleic acid sequence is under the control of a heart-specific promoter.

3. The method of claim 1, wherein the nucleic acid sequence comprises the entire length of SEQ ID NO: 12.

4. The method of claim 1, wherein the host is a prokaryotic or eukaryotic cell.

5. The method of claim 1, wherein the compound promoting the expression and/or the activity of the lncRNA of SEQ ID NO: 12 is formulated as a pharmaceutical composition.

6. The method of claim 5, wherein the pharmaceutical composition comprises a pharmaceutically acceptable carrier or excipient.

7. The method of claim 1, wherein the compound promoting the expression and/or the activity of the lncRNA of SEQ ID NO: 12 is formulated as a vesicle.

8. The method of claim 7, wherein the vesicle is a liposome.

* * * * *